(12) United States Patent
Douma et al.

(10) Patent No.: US 6,660,915 B2
(45) Date of Patent: Dec. 9, 2003

(54) LOW LIPOXYGENASE 1 BARLEY

(76) Inventors: Anna Christina Douma, Eikenlaan 11B, 3707 SB, Zeist (NL); Albert Doderer, Albast 47, 2719TV, Zoetermeer (NL); Verena Cameron-Mills, Kirkevaenget 20, DK-2500, Valby (DK); Birgitte Skadhauge, Lindehoejvej 31B, DK-360, Birkeroed (DK); Lene Moelskov Bech, Roerkaer 6, DK-2765, Smoerum (DK); Natalie Schmitt, Cornelis Jolstraat 56, 2584 ET, Den Haag (NL); Jolanda Carolina Heistek, Van Blankenfeimstraat 15, 3132 VA, Vlaardingen (NL); Johannes Reinier van Mechelen, Brouwersgracht 214, 1013HD, Amsterdam (NL)

( * ) Notice: Subject to any disclaimer, the term of this patent is extended or adjusted under 35 U.S.C. 154(b) by 66 days.

(21) Appl. No.: 09/751,687

(22) Filed: Dec. 29, 2000

(65) Prior Publication Data

US 2003/0167544 A1 Sep. 4, 2003

(51) Int. Cl.[7] ............... C12N 15/82; C12C 1/00; C12C 11/00; A01H 5/00; A01H 5/10
(52) U.S. Cl. ............ 800/320; 800/278; 800/298; 435/183; 435/185; 426/7; 426/11; 426/64
(58) Field of Search ............... 800/298, 278, 800/320; 435/185, 7, 6, 183; 426/392, 7, 11, 64

(56) References Cited

U.S. PATENT DOCUMENTS 5,510,474 A 4/1996 Quail et al.

FOREIGN PATENT DOCUMENTS

| WO | WO 97/13851 | 4/1997 |
| WO | WO 97/26364 | 7/1997 |

OTHER PUBLICATIONS

Hornung et al. Coversion of cucumber linoleate 13–lipoxygenase to a 9–lipoxygenating species by site–directed mutagenesis. Proc. Natl. Acad. Sci. (Plant Biology), Mar. 1999. vol. 96, pp. 4192–4197.*
Olsen et al. Sodium azide mutagenesis: Preferential generation of A T—G C transitions in the barley Ant18 gene. Proc. Natl. Acad. Sci. USA (Genetics). Sep. 1993, vol. 90, pp. 8043–8047.*
Schwarz et al. Rapid Separationo and Genotypic Variablilty of Barley (*Hordeum vulgare L*) Lipoxygenase Isoenzymes. Journal of Cereal Science (1997) 25 49–56.*
Shen et al. Alteration of spinach ribulose–1, 5–bisphosphate carboxylase/oxygenase activase activities by site–directed mutagenesis. Plant physiology, Jul. 1992. vol. 99, No. 3. p. 1201–1207.*

Kowaka, M., "Malting barley improvement for brewing", *Chemical Abstracts*, vol. 119, No. 23, p. 828 (Jun. 12, 1993).
Wang et al., "Molecular basis of a null mutation in soybean lipoxygenase 2: Substitution of glutamine for an iron–ligand histidine", *Proc. Natl. Acad. Sci*, vol. 91, pp. 5828–5832 (Jun. 1994).
Hildebrand, D. et al., "Lipoxygenase 3 Reduces Hexanal Production from Soybean See Homogenates", *J. Agric. Food Chem.*, vol. 38, pp. 1934–1936 (1990).
Holtman, W. et al., "Differential Expression of Lipoxygenase Isoenzymes in Embryos of Germinating Barley", *Plant Physiol.*, vol. 111, pp. 569–576 (1996).
Ibrahim, M. et al., "Real–Time Microchip PCR for Detecting Single–Base Differences in Viral and Human DNA", *Anal. Chem.*, vol. 70, pp. 2013–2017 (1998).
Jensen, L. et al., "Inheritance of a Codon–Optimized Transgene Expressing Heat Stable (1,3–1,4)–β–glucanase in Scutellum and Aleurone of Germinating Barley", *Hereditas*, vol. 129, pp. 215–225 (1998).
Johannesen, P. et al., "Construction of *S. carlsbergensis* Brewer's Yeast Without Production of Sulfite", *EBC Congress*, pp. 655–662 (1999).
Kjaerulff, S. et al., "Antisense Repression of PsaE mRNA in Transgenic Barley", *Photosynthesis: from Light to Biosphere*, vol. II, pp. 151–154 (1995).
Kleinhofs, A. et al., "Inductiona and Selection of Specific Gene Mutations in Hordeum and Pisum", *Mutation Research*, vol. 51, pp. 29–35 (1978).
Laemmli, V. "Cleavage of Structural Proteins During the Assembly of the Head of Bacteriophage T4", *Nature*, vol. 227, pp. 680–685 (Aug. 15, 1970).
Lee, B. et al., "Transient Gene Expression in Aleurone Protoplasts Isolated from Developing Caryopses of Barley and Wheat", *Plant Molecular Biology*, vol. 13, pp. 21–29 (1989).
McElroy, D. et al., "What's Brewing in Barley Biotechnology?", *Bio/Technology*, vol. 13, pp. 245–248 (Mar. 13, 1995).
Meilgaard, M. "Flavor Chemistry of Beer: Part II: Flavor and Threshold of 239 Aroma Volatiles", *MBAA Technical Quarterly*, vol. 12, No. 3, pp. 151–168 (1975).
Minor, W. et al., "Crystal Structure of Soybean Lipoxygenase L–1 at 1.4 Å Resolution", *Biochemistry*, vol. 35, pp. 10687–10701 (1996).
Narvel, J. et al., "Agronomic and Seed Traits of Soybean Lines Lacking Seed Lipoxygenases", *Crop Science*, vol. 38, pp. 926–928 (1998).

(List continued on next page.)

Primary Examiner—David T. Fox
Assistant Examiner—Russell Kallis
(74) Attorney, Agent, or Firm—Merchant & Gould P.C.

(57) ABSTRACT

Barley plants having reduced lipoxygenase-1 enzyme activity are provided, for example, barley plants expressing mutant LOX-1 protein. The barley plants of the invention are useful in the production of plant products such as malt and brewed beverages, particularly beer, having increased stability and reduced T2N potential.

11 Claims, 29 Drawing Sheets

OTHER PUBLICATIONS

Noel, S. et al., "Release of Deuterated Nonenal During Beer Aging from Labeled Precursors Synthesized in the Boiling Kettle", *J. Agric. Food Chem.*, vol. 47, pp. 4323–4326 (1999).

Olsen, O. et al., "Sodium Azide Mutagenesis: Preferential Generation of A•T→G•C Transitions in the Barley Ant18 Gene", *Proc. Natl. Acad. Sci.*, vol. 90, pp. 8043–8047 (Sep., 1993).

Parker, M. et al., "A Consensus Residue Analysis of Loop and Helix–Capping Residues in Four–α–Helical–Bundle Proteins", *Protein Engineering*, vol. 10, No. 5, pp. 487–496 (1997).

Pich, J. et al., "Midiprep Method for Isolation of DNA from Plants with a High Content of Polyphenolics", *Nucleic Acids Reseach*, vol. 21, No. 14, 1 page (1993).

Rank, J. et al., "Allium cepa Anaphase–Telophase Root Tip Chromosome Aberration Assay on N–methyl–N–nitrosourea, Maleic Hydrazide, Sodium Azide, and Ethyl Methanesulfonate", *Mutation Research*, vol. 390, pp. 121–127 (1997).

Robinson, D. et al., "Lipoxygenases and the Quality of Foods", *Food Chemistry*, vol. 54, pp. 33–43 (1995).

Aarle, P. et al., "Purification of a Lipoxygenase from Ungerminated Barley Characterization and Product Formation", *FEBS Letters*, vol. 280, No. 1, pp. 159–162 (Mar., 1991).

Aastrup, S. et al., "Malt Specifications and Analyses (Sense and Nonsense)", *Louvain Brewing Letters*, vol. 4, No. 1, pp. 16–20 (1991).

Beetham, P. et al., "A Tool for Functional Plant Genomics: RNA/DNA Oligonucleotides Cause in vivo Gene–Specific Mutations", *Proc. Natl. Acad. Sci.*, vol. 96, pp. 8774–8778 (Jul., 1999).

Bevan, M. et al., "Structure and Transcription of the Nopaline Synthase Gene Region of T–DNA", *Nucleic Acids Research*, vol. 11, No. 2, pp. 369–385 (1983).

Bradford, M. "A Rapid and Sensitive Method for the Quantitation of Microgram Quantities of Protein Utilizing the Principle of Protein–Dye Binding", *Analytical Biochemistry*, vol. 72, pp. 248–254 (1976).

Broun, P. et al., "Genetic Engineering of Plant Lipids", *Annu. Rev. Nutr.*, vol. 19, pp. 197–213 (1999).

Drost, B. et al., "Flavor Stability", *ASBC Journal*, vol. 48, No. 4, pp. 124–131 (1990).

Dufour, J. "Influence of Industrial Brewing and Fermentation Working Conditions on Beer S02 level and Flavour Stability", *EBC Congress*, pp. 209–216 (1991).

Eskin, N. et al., "Biochemistry of Lipoxygenase in Relation to Food Quality", *CRC Critical Reviews in Food Science and Nutrition*, vol. 9, pp. 1–40 (1977).

Funatsuki, H. et al., "Fertile Transgenic Barley Generated by Direct DNA Transfer to Protoplasts", *Theor. Appl. Genetics*, vol. 91, pp. 707–712 (1995).

Gardner, H. "Lipoxygenase Pathway in Cereals", *Advances in Cereal Science and Technology*, vol. IX, Chapter 6, pp. 161–215 (1988).

Gebhardt, C. et al., Restriction Fragment Length Polymorphism Analysis of Plant Genomes and its Application to Plant Breeding, *Int'l Review of Cytology*, vol. 135, pp. 201–237 (1992).

Getranke–Fachverlag, V. "Analytica–EBC", *European Brewery Convention*, 15 pgs. (1998).

Gilpin, M. et al., "The Effect of Reduced PSI–K Protein Levels on Photosynthesis in Transgenic Barley", *Photosynthesis: Mechanisms and Effects*, vol. IV, pp. 2983–2986 (1998).

Gronqvist, A. et al., "Carbonyl Compounds During Beer Production and in Beer", *EBC Congress*, pp. 421–428 (1993).

Hensgens, L. et al., "Isolation of RNA ana DNA from Different Rice Tissues", *Rice Genetics Newsletter*, vol. 6, pp. 163–168 (1989).

Rouster, J. et al., "Indentification of a Methyl Jasmonate–Responsive Region in the Promoter of a Lipoxygenase 1 Gene Expressed in Barley Grain", *The Plant Journal*, vol. 11, No. 3, pp. 513–523 (1997).

Rouster, J. et al., "The Untranslated Leader Sequence of the Barley Lipoxygenase 1 (Lox1) Gene Confers Embryo–Specific Expression", *The Plant Journal*, vol. 15, No. 3, pp. 435–440 (1998).

Sambrook, J. et al., "Extraction, Purification, and Analysis of Messenger RNA from Eukaryotic Cells", *Molecular Cloning*, 8 pgs (1989), A Laboratory Manual Second Edition.

Schmitt, N. et al., "Expression of Lipoxygenase Isoenzymes in Developing Barley Grains", *Plant Science*, vol. 128, pp. 141–150 (1997).

Skriver, K. et al., "Cis–Acting DNA Elements Responsive to Gibberellin and its Antagonist Abscisic Acid", *Proc. Natl. Acad. Sci.*, vol. 88, pp. 7266–7270 (Aug., 1991).

Skrzypczak–Jankun, E. et al., "Structure of Soybean Lipoxygenase L3 and a Comparison with its Isoenzyme", *Proteins: Structure, Function, and Genetics*, vol. 29, pp. 15–31 (1997).

Suzuki, Y. et al., "Volatile Components in Stored Rice [*Oryza sativa* (L.)] of Varieties with and without Lipoxygenase–3 in Seeds", *J. Agric. Food Chem.*, vol. 47, pp. 1119–1124 (1999).

Tingay, S. et al., "Agrobacterium Tumefaciens–Mediated Barley Transformation", *The Plant Journal*, vol. 11, No. 6, pp. 1369–1376 (1997).

Towbin, H. et al., "Electrophoretic Transfer of Proteins from Polyacrylamide Gels to Nitrocellulose Sheets: Procedure and Some Applications", *Proc. Natl. Acad. Sci.*, vol. 76, No. 9, pp. 4350–4354 (Sep., 1979).

van den Berg, B. et al., "Equipment for Rapid Homogenization of High Numbers of Plant Tissue for Electrophoretic Analysis of Proteins", *Electrophoresis*, vol. 13, pp. 76–81 (1992).

van Mechelen, J. et al., "Primary Structure of a Lipoxygenase from Barley Grain as Deduced from its cDNA Sequence", *Biochimica et Biophysica Acta*, vol. 1254, pp. 221–225 (1995).

van Mechelen, J. et al., "Molecular Characterization of Two Lipoxygenases from Barley", *Plant Molecular Biology*, vol. 39, pp. 1283–1298 (1999).

Wan, Y. et al., "Generation of Large Numbers of Independently Transformed Fertile Barley Plants", *Plant Physiol.*, vol. 104, pp. 37–48 (1994).

Yoon, K. et al., "Targeted Gene Correction of Episomal DNA in Mammalian Cells Mediated by a Chimeric RNA DNA Oligonucleotide", *Proc. Natl. Acad. Sci.*, vol. 93, pp. 2071–2076 (Mar., 1996).

Zhu, T. et al., "Targeted Manipulation of Maize Genes in vivo Using Chimeric RNA/DNA Oligonucleotides", *Proc. Natl. Acad. Sci.*, vol. 96, pp. 8768–8773 (Jul., 1999).

\* cited by examiner

FIGURE 12A (-288) Promoter

```
LG  CAGCCCCATGCATGCACATGCACATGCAGTGCAGCCAAGCACCGTCGTCGATGGGCGATCACCCGTCACG  -208
WT  CAGCCCCATGCATGCACATGCACATGCAGTGCAGCCAAGCACCGTCGTCGATGGGCGATCACCCGTCACG

LG  GGACCGGAGCGCGCCATGCGAAGCACGAGGAGGGCACGTCACCGTCCGCGCGCAGCACGTGGAGAGCACGTCGCCGTCCG  -128
WT  GGACCGGAGCGCGCCATGCGAAGCACGAGGAGGGCACGTCACCGTCCGCGCGCAGCACGTGGAGAGCACGTCGCCGTCCG

LG  ATCCATCTCTCCAAAGCCGAGCCGCCACACCCACCGGGACCCGGACCCGGACCCGGCCTATAAATTGCCCGGACCGAGCTGCAA  -48
WT  ATCCATCTCTCCAAAGCCGAGCCGCCACACCCACCGGGACCCGGACCCGGACCCGGCCTATAAATTGCCCGGACCGAGCTGCAA
                                                            Transcription start site (+1)

LG  GCAGCTCCTCACACACTCACGCAACACACATCCATCTTCACTGAAAAACAGTGTGCTGGTGCCATTGGTTG  32
WT  GCAGCTCCTCACACACTCACGCAACACACATCCATCTTCACTGAAAAACAGTGTGCTGGTGCCATTGGTTG

LG  GAGCAGTGAAAGCGAGGAGAGGCCAAGAACAAGATGCTGCTGGGAGGCTGATGACACCCTCACGGGGCGAACAA  112
WT  GAGCAGTGAAAGCGAGGAGAGGCCAAGAACAAGATGCTGCTGGGAGGCTGATGACACCCTCACGGGGCGAACAA
                                Translation start site (+69) →

LG  GAGCGCCCGGCTCAAGGGCACGGTGGTGCTCATGCGCAAGAACGTGCTGGACCTCAACGACTTCGGCGCCACCATCATCG  192
WT  GAGCGCCCGGCTCAAGGGCACGGTGGTGCTCATGCGCAAGAACGTGCTGGACCTCAACGACTTCGGCGCCACCATCATCG

LG  ACGGCCATCGGCGAGTTCCTCGGCAAGGGTGTCACCTGCCAGCTTATCAGTCCACCGCCGTCGACCAAGGTAATCACTAC  272
WT  ACGGCCATCGGCGAGTTCCTCGGCAAGGGGCGTCACCTGCCAGCTTATCAGTCCACCGCCGTCGACCAAGGTAATCACTAC
                        (Silent mutation)*

LG  CCTCCTCCGGCCTTCCTCCTCCTCTGTTTACAAGATATAGTATTTCTTTCGTGTGGGCCGGCCATGGATGGATGTGT  352
WT  CCTCCTCCGGCCTTCCTCCTCCTCTGTTTACAAGATATAGTATTTCTTTCGTGTGGGCCGGCCATGGATGGATGTGT

LG  CTGGATCGGCTAAAGAAGAATAGGATAGCCCTGGCCGTCGTCTTTACCTGAGCATGGCCATATGCCATCGAAAAAA  432
WT  CTGGATCGGCTAAAGAAGAATAGGATAGCCCTGGCCGTCGTCTTTACCTGAGCATGGCCATATGCCATCGAAAAAA
```

FIGURE 12B

```
LG  GAGACAACAGCATGCATGGTGCGCGCACCAGAGACCACCGCAGAGCAAAGCAACACAACAAGC  512
WT  GAGACAACAGCATGCATGGTGCGCGCACCAGAGACCACCGCAGAGCAAAGCAACACAACAAGC

LG  AAGGACGACACGTCAAAAGCAACACAACAAGACAAGGACGGCACGTCAAAAGCAACACAACAAACCTAAACTAAAGCACAAAGA  592
WT  AAGGACGACACGTCAAAAGCAACACAACAAGACAAGGACGGCACGTCAAAAGCAACACAACAAACCTAAACTAAAGCACAAAGA

LG  CGTAAGAGCAAGCACACAATCAGCAGGCTATAAACAGTTGTCATCAAAAACAACGCTGGAAGAGAGAAGGAAGGAA  672
WT  CGTAAGAGCAAGCACACAATCAGCAGGCTATAAACAGTTGTCATCAAAAACAACGCTGGAAGAGAGAAGGAAGGAA

LG  GTAGTAGCCATGAAAAATTAAATCACCGGGCGTTGCTCTTTGCCCAACAATTAATCAAGCAGGGTACGTGGCATGTATAG  752
WT  GTAGTAGCCATGAAAAATTAAATCACCGGGCGTTGCTCTTTGCCCAACAATTAATCAAGCAGGGTACGTGGCATGTATAG

LG  TTCTTGTAAGTAAACTAAGCATGTGATATGAGAAGGTACGTGGTGTGCAGACAACGCGGTCGCGGGAAGGTGGGCGCG  832
WT  TTCTTGTAAGTAAACTAAGCATGTGATATGAGAAGGTACGTGGTGTGCAGACAACGCGGTCGCGGGAAGGTGGGCGCG

LG  GAGGCGGAGCTGGAGCAGTGGGTGACGAGCCTGCCGTCGCTGCTGACGACGGGGGAGTCCAAGTTCGGCCTCACCTTCGACTG  912
WT  GAGGCGGAGCTGGAGCAGTGGGTGACGAGCCTGCCGTCGCTGCTGACGACGGGGGAGTCCAAGTTCGGCCTCACCTTCGACTG

LG  GGAGGTGGAGAAGCTCGGGGTGCCGGGCGCCATCGTCGTCAACAACTACCACCAGCTCCGAGTTCCTGCTTAAAACCATCA  992
WT  GGAGGTGGAGAAGCTCGGGGTGCCGGGCGCCATCGTCGTCAACAACTACCACCAGCTCCGAGTTCCTGCTTAAAACCATCA

LG  CCCTCCACGACGTCCCCGGCCGCCAGCGGCAACCTCGTCGCCAACTCATGGATCTACCCGCCAACTACCGA  1072
WT  CCCTCCACGACGTCCCCGGCCGCCAGCGGCAACCTCGTCGCCAACTCATGGATCTACCCGCCAACTACCGA

LG  TACAGCCGCGTCTTCTTCGCCAACGACGTGCGTGGATTTTCCCTCTACTTTCCTCCTTTCATTTTCACCGCCTTCGTCA  1152
WT  TACAGCCGCGTCTTCTTCGCCAACGACGTGCGTGGATTTTCCCTCTACTTTCCTCCTTTCATTTTCACCGCCTTCGTCA
```

FIGURE 12C

```
LG  TTCATGGTCGATCATTAAGTCTTGCCAGGACAATAGATGATGAGCTAGGAGTGGTTACCACTTAGCAGTACGTACATTAT  1232
WT  TTCATGGTCGATCATTAAGTCTTGCCAGGACAATAGATGATGAGCTAGGAGTGGTTACCACTTAGCAGTACGTACATTAT

LG  TTATTCCGTGTTGGTAGAAAAGGATATGGTTTGGTGCAGATCGACACAAGATTGAATGAAAGTTGCACCGTGGCACCGTG  1312
WT  TTATTCCGTGTTGGTAGAAAAGGATATGGTTTGGTGCAGATCGACACAAGATTGAATGAAAGTTGCACCGTGGCACCGTG

LG  GCAGCGTGGTAGTGAAAATAACTGTTGCACGGATCCACCCACATGATTGTTTCATGAATAAACTTTTTAAGGATGTGT   1392
WT  GCAGCGTGGTAGTGAAAATAACTGTTGCACGGATCCACCCACATGATTGTTTCATGAATAAACTTTTTAAGGATGTGT

LG  CTAGCCACACATCTAGATGCATGTCACATAATTATTGCATACCAAAACGATTAAATTAAGCATAAAAAGAAAAGGAAAAA  1472
WT  CTAGCCACACATCTAGATGCATGTCACATAATTATTGCATACCAAAACGATTAAATTAAGCATAAAAAGAAAAGGAAAAAA

LG  TACTCACATATCTCGACGTAAGATCAATGATATAGTATTTAGATATGCAATATTTATCTTACATCTAAACCTTTCTTCAT  1552
WT  TACTCACATATCTCGACGTAAGATCAATGATATAGTATTTAGATATGCAATATTTATCTTACATCTAAACCTTTCTTCAT

LG  TCTTAAATATAAGACATTTGTAAGATTTCACTATGGACAACATACGAAACAAAATCAGTGGATCTCTCTATGCATTCATT  1632
WT  TCTTAAATATAAGACATTTGTAAGATTTCACTATGGACAACATACGAAACAAAATCAGTGGATCTCTCTATGCATTCATT

LG  ATGTAGTCTATAATAAATCTTTAAAAGATCGTATATTTTGCAACGGAGGGAGTAAAACATAACTTTTTAATAGTAATGT  1712
WT  ATGTAGTCTATAATAAATCTTTAAAAGATCGTATATTTTGCAACGGAGGGAGTAAAACATAACTTTTTAATAGTAATGT

LG  TGCACGGCTCCACACTCGCAGACGTACCTGCCGAGCCAGATGCCGGCGCTGAAGCCGTACCGCGACGACGAGCTCCG    1792
WT  TGCACGGCTCCACACTCGCAGACGTACCTGCCGAGCCAGATGCCGGCGCTGAAGCCGTACCGCGACGACGAGCTCCG

LG  GAACCTGCGTGGCGACGACCAGCAGGGCCCGTACCAGGAGCACGACCGCATCTACCGCTACGACGTCTACAACGACCTCG  1872
WT  GAACCTGCGTGGCGACGACCAGCAGGGCCCGTACCAGGAGCACGACCGCATCTACCGCTACGACGTCTACAACGACCTCG
```

FIGURE 12D

```
LG  GCGAGGGCCGCCCCATCCTCGGCGGCAACTCCGACCACCCTTACCCGCGCGGCGAGGCGCAAGCCCAACGCC  1952
WT  GCGAGGGCCGCCCCATCCTCGGCGGCAACTCCGACCACCCTTACCCGCGCGGCGAGGCGCAAGCCCAACGCC

LG  AGCGACCCGAGCCTGGAGAGCCGGCTGTCGCTGCTGGAGCAGATCTACGTGCCGCGGACGAGAAGTTCGGCCACCTCAA  2032
WT  AGCGACCCGAGCCTGGAGAGCCGGCTGTCGCTGCTGGAGCAGATCTACGTGCCGCGGACGAGAAGTTCGGCCACCTCAA

LG  GACGTCCGACTTCCTGGGCTACTCCATCAAGGCCATCACGCAGGGCATCCTGCCGTGCCACCTACGTGGACACCA  2112
WT  GACGTCCGACTTCCTGGGCTACTCCATCAAGGCCATCACGCAGGGCATCCTGCCGTGCCACCTACGTGGACACCA

LG  CCCCCGGCGAGTTCGACTCCTTCCAGGACACATCATCAACCTCTATGAGGGCGCATCAAGCTGCCCAAGGTGGCCGCCCCTG  2192
WT  CCCCCGGCGAGTTCGACTCCTTCCAGGACACATCATCAACCTCTATGAGGGCGCATCAAGCTGCCCAAGGTGGCCGCCCCTG

LG  GAGGAGCTCCGTAAGCAGTTCCCGCTCATCAAGGACCTCCCCGTCGGCGGCGACTCCCTGCTTAAGCTCCC  2272
WT  GAGGAGCTCCGTAAGCAGTTCCCGCTCATCAAGGACCTCCCCGTCGGCGGCGACTCCCTGCTTAAGCTCCC (Mutant site)*
LG  CGTGCCCCACATCATCCAGGAGAACAAGCAGGCGTGGAGGACCGACGAGGAGTTCGACGGGAGGTGCTCGCCGACGTCA  2352
WT  CGTGCCCCACATCATCCAGGAGAACAAGCAGGCGTGGAGGACCGACGAGGAGTTCGACGGGAGGTGCTCGCCGGCGTCA LG  ACCCGGTCATGATCACGCGTCTCACGGTGAGTCAGCGATTATTGTTCATTGTGTGTATGGTGTCCATGGTGAGAAAG  2432
WT  ACCCGGTCATGATCACGCGTCTCACGGTGAGTCAGCGATTATTGTTCATTGTGTGTATGGTGTCCATGGTGAGAAAG LG  TGCAGATCTTGATTTGCGTTGGGTCGCATGCATGCACGCATGCTGCAGGAGTTCCCGCCAAAAAGTAGTCTGACC  2512
WT  TGCAGATCTTGATTTGCGTTGGGTCGCATGCATGCACGCATGCTGCAGGAGTTCCCGCCAAAAAGTAGTCTGACC
```

FIGURE 12E

```
LG  CTAGCAAGTTTGGTGACCACCACCAGCACCATCACGGCGGAGCACATAGAGAAGAACCTCGAGGGCCTCACGGTGCAGCAG  2592
WT  CTAGCAAGTTTGGTGACCACCACCAGCACCATCACGGCGGAGCACATAGAGAAGAACCTCGAGGGCCTCACGGTGCAGCAG

LG  GTAATTGGTCCAAGCCATCGACATCAACTATGATTTACCTAGAGAGTAATTGGTAGCTGTAGATAATTTGGCTTCGTTGCA  2672
WT  GTAATTGGTCCAAGCCATCGACATCAACTATGATTTACCTAGAGAGTAATTGGTAGCTGTAGATAATTTGGCTTCGTTGCA

LG  ATTAATTTGATGCTGCCGATCAAGTGATCGTATTGGGTTTGAAATTTGCAGGCGCTGGAAAGCAACAGGCTGTACATCC    2752
WT  ATTAATTTGATGCTGCCGATCAAGTGATCGTATTGGGTTTGAAATTTGCAGGCGCTGGAAAGCAACAGGCTGTACATCC

LG  TTGATCACCATGACCGGTTCATGCCGTTCCTGATCGACGTCAACAACCTGCCCGGCAACTTCATCTACGCCACGAGGACC  2832
WT  TTGATCACCATGACCGGTTCATGCCGTTCCTGATCGACGTCAACAACCTGCCCGGCAACTTCATCTACGCCACGAGGACC

LG  CTCTTCTTCCTGCGCGGCGACGGCCAGGCTCACGCGCCGCTCGCCGCTCGAGCTGAGCCCATCATCCAGGGCGGCCTTAC  2912
WT  CTCTTCTTCCTGCGCGGCGACGGCCAGGCTCACGCGCCGCTCGCCGCTCGAGCTGAGCCCATCATCCAGGGCGGCCTTAC

LG  CACGGCCAAGAGCAAGGTTTACACGCCGGTGCCCAGCGGCTCCGTCGAAGGCTGGGTGTGGGAGCTCGCCAAGGCCTACG  2992
WT  CACGGCCAAGAGCAAGGTTTACACGCCGGTGCCCAGCGGCTCCGTCGAAGGCTGGGTGTGGGAGCTCGCCAAGGCCTACG

LG  TCGCCGTCAATGACTCCGGGTGGCACCAGCTCGTCGTTCAGCCACTGGTACGTTCTCCACGGTCGATGTGATTCAGTCGA  3072
WT  TCGCCGTCAATGACTCCGGGTGGCACCAGCTCGTCGTTCAGCCACTGGTACGTTCTCCACGGTCGATGTGATTCAGTCGA

LG  TGCACAACAACTGATCGAAATATGATTGAATGAAACGCGAGGCTGAACACTCACGCGGTGATGGAGCCGTTCGTGATCT   3152
WT  TGCACAACAACTGATCGAAATATGATTGAATGAAACGCGAGGCTGAACACTCACGCGGTGATGGAGCCGTTCGTGATCT

LG  CGACGAACCGGCACCTTAGCGTGACGCACCCGGTGCACAAGTCGCTGAGCCCGACTACCGCGACACCATGACCATCAAC   3232
WT  CGACGAACCGGCACCTTAGCGTGACGCACCCGGTGCACAAGTCGCTGAGCCCGACTACCGCGACACCATGACCATCAAC
```

FIGURE 12F

```
LG  GCGCTGGCGCGGCAGACGCTCATCAACGCCGGCGCGGCATCTTCGAGATGACGGTGTTCCCGGGCAAGTTCGCGTTGGGGAT 3312
WT  GCGCTGGCGCGGCAGACGCTCATCAACGCCGGCGCGGCATCTTCGAGATGACGGTGTTCCCGGGCAAGTTCGCGTTGGGGAT

LG  GTCGGCCGTGGTGTACAAGGACTGGAAGTTCACCGAGCAGGACTGCCGGACGATCTCATCAAGAGTACGTACCTGGTA 3392
WT  GTCGGCCGTGGTGTACAAGGACTGGAAGTTCACCGAGCAGGACTGCCGGACGATCTCATCAAGAGTACGTACCTGGTA

LG  AATGTTATGAATGTGTAAAACAAATTGGGCGTCTCGCTCACTGACAGGAACGTGTAAAAAAATGCAGGGCATGGCGG 3472
WT  AATGTTATGAATGTGTAAAACAAATTGGGCGTCTCGCTCACTGACAGGAACGTGTAAAAAAATGCAGGGCATGGCGG

LG  TGGAGGACCCCGTCGAGCCCGTACAAGGTGCGGTTGCGGTTGCTGGTGTCGGACTACCCGTACGCGGCGGACGGGCTGGCGATCTGG 3552
WT  TGGAGGACCCCGTCGAGCCCGTACAAGGTGCGGTTGCGGTTGCTGGTGTCGGACTACCCGTACGCGGCGGACGGGCTGGCGATCTGG

LG  CACGCCATTGAGCAGTACGTGAGCGAGTACCTGGCCATCTACTACCCGGAACGACGGCGTGCTGCAGGGCGATACGGAGGT 3632
WT  CACGCCATTGAGCAGTACGTGAGCGAGTACCTGGCCATCTACTACCCGGAACGACGGCGTGCTGCAGGGCGATACGGAGGT

LG  GCAGGCGTGGTGGTGAAGGAGACGCGCGAGGTCGGGCACGGCGACCTCAAGGACGCCCCATGGTGGCCCAAGATGCAAAGTG 3712
WT  GCAGGCGTGGTGGTGAAGGAGACGCGCGAGGTCGGGCACGGCGACCTCAAGGACGCCCCATGGTGGCCCAAGATGCAAAGTG

LG  TGCCCGGAGCTGGCCAAGGCGTGCACCACCATCATCTGGATCGGTCGGCGCTGCATGCGGCAGTCAACTTCGGGCAGTAC 3792
WT  TGCCCGGAGCTGGCCAAGGCGTGCACCACCATCATCTGGATCGGTCGGCGCTGCATGCGGCAGTCAACTTCGGGCAGTAC

LG  CCCTACGCGGGGTTCCTCCCGAACCGGCCGGCCGGCGTGAGCGGCGGCGACGGAGGAGTACGCGGA 3872
WT  CCCTACGCGGGGTTCCTCCCGAACCGGCCGGCCGGCGTGAGCGGCGGCGACGGAGGAGTACGCGGA

LG  GCTGGAGCGCGACCCGGAGCGGGCCTTCATCCACACCATCACGAGCCAGATCCAGACCATTCGGCGTGTCGCTGCTGG 3952
WT  GCTGGAGCGCGACCCGGAGCGGGCCTTCATCCACACCATCACGAGCCAGATCCAGACCATTCGGCGTGTCGCTGCTGG
```

FIGURE 12G

```
LG  AGGTGCTGTCGAAGCACTCCTCCGACGAGCTGTACCTCGGGCAGCGGGACACGCCGGAGTGGACCTCGGACCCAAAGGCC 4032
WT  AGGTGCTGTCGAAGCACTCCTCCGACGAGCTGTACCTCGGGCAGCGGGACACGCCGGAGTGGACCTCGGACCCAAAGGCC

LG  CTGGAGGTGTTCAAGCGGTTCAGCGACGGCTGGTGGAGATCGAGAGCAAGGTGGTGGGCATGAACCATGACCCGGAGCT 4112
WT  CTGGAGGTGTTCAAGCGGTTCAGCGACGGCTGGTGGAGATCGAGAGCAAGGTGGTGGGCATGAACCATGACCCGGAGCT

LG  CAAGAACCGCAACGGCCCGGCTAAGTTCCCTACATGCTGCTCTACCCCAACACCCTCCGACCACCAAGGGCGCCGCTGCCG 4192
WT  CAAGAACCGCAACGGCCCGGCTAAGTTCCCTACATGCTGCTCTACCCCAACACCCTCCGACCACCAAGGGCGCCGCTGCCG

LG  GGCTTACCGCCAAGGGCATCCCCAACAGCAGCATCCATCTAAGCCATGGATGAATAAAGGGCGTTC 4272
WT  GGCTTACCGCCAAGGGCATCCCCAACAGCAGCATCCATCTAAGCCATGGATGAATAAAGGGCGTTC
                      translation stop (4229)

LG  GCCACGTACGAAACTTGTCGAGAGATTGGTGTGTAGTGTGTGTCTGTGACAGTACTATGTCAGCAGTTGCTCTTTAAGCCCGA 4352
WT  GCCACGTACGAAACTTGTCGAGAGATTGGTGTGTAGTGTGTGTCTGTGACAGTACTATGTCAGCAGTTGCTCTTTAAGCCCGA

LG  ATAAATAAAGCAGATTTGCTTCC 4375
WT  ATAAATAAAGCAGATTTGCTTCC
```

FIGURE 13
Wild-type LOX-1 gene structure:
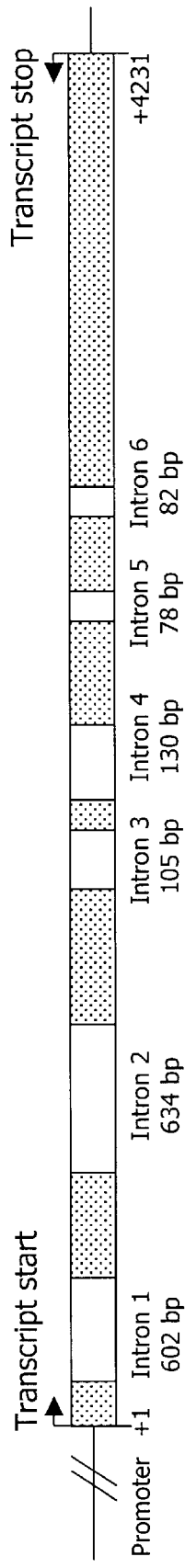
Line G lox-1 gene structure:
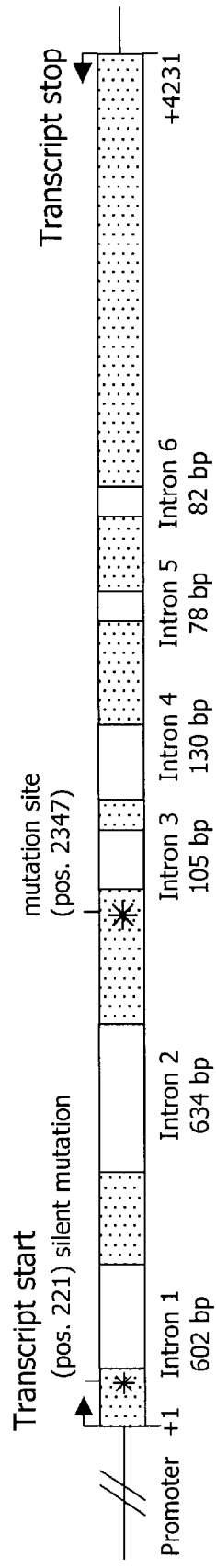

Backcrossing program for Line G to cv Alexis

FIGURE 22 A
LIPOXYGENASE AMINO ACID SEQUENCE ALIGNMENT

```
      1             E1    H                                           60
Gm1  MFS..........A.GHKIKGTVVLMPKNELE...................VNPDGSAV
Gm2  MFSVPGVSGILNRGG.GHKIKGTVVLMRKNVLDFNSVADLTKGNVGGLIGTGLNVVGSTL
Gm3  M.....LGGLLHRG...HKIKGTVVLMRKNVLDVNSVT.....SVGGIIGQGLDLVGSTL
Hv2  MLGVGGIVSDLTGGIRGAHLKGSVVLMRKNALDFN................DFGAHVM
Hv1  ML.LGGLIDTLTGANKSARLKGTVVLMRKNVLDLN................DFGATII
      61      +    E2       ++ +  E3           +    +  E4   120
Gm1  DNLNAFLGRSVSLQLISATKADAH..GKGKVGKDTFLEG..INTSLPTLGAGESAFNIHF
Gm2  DNLTAFLGRSVALQLISATKPLAN..GKGKVGKDTFLEG..IIVSLPTLGAGESAFNIQF
Gm3  DTLTAFLGRSVSLQLISATKADAN..GKGKLGKATFLEG..IITSLPTLGAGQSAFKINF
Hv2  DGVTELLGRGVTCQLISSTNVDHNNGGRGKVGAEANLEQWLLPTNLPFITTGENKFAVTF
Hv1  DGIGEFLGKGVTCQLISSTAVDQDNGGRGKVGAEAELEQWV..TSLPSLTTGESKFGLTF
      121     + + E5         E6          +     E7       E8  180
Gm1  EWD.GSMGIPGAFYIKNYMQVEFFLKSLTLEAISNQ.GTIRFVCNSWVYNTKLYKSVRIF
Gm2  EWD.ESMGIPGAFYIKNYMQVEFYLKSLTLEDVPNQ.GTIRFVCNSWVYNTKLYKSVRIF
Gm3  EWD.DGSGIPGAFYIKNFMQTEFFLVSLTLEDIPNH.GSIHFVCNSWIYNAKLFKSDRIF
Hv2  DWSVDKLGVPGAIIVKNNHASEFFLKTITLDNVPGR.GTIVFVANSWVYPQAKYRYNRVF
Hv1  DWEVEKLGVPGAIVVNNYHSSEFLLKTITLHDVPGRSGNLTFVANSWIYPAANYRYSRVF
      181     +   + H1         +     +       E         +    240
Gm1  FANHTYVPSETPAPLVSYREEELKSLRGNGT.GERKEYDRIYDYDVYNDLGNPDKSEKLA
Gm2  FANHTYVPSETPAALVGYREEELKNLRGDGK.GERKEHDRIYDYDVYNDLGNPDHGENFA
Gm3  FANQTYLPSETPAPLVKYREEELHNLRGDGT.GERKEWERIYDYDVYNDLGDPDKGENHA
Hv2  FANDTYLPHQMPAALKPYRDDELRNLRGDDQQGPYLDHDRVYRYDVYNDLGD.......S
Hv1  FANDTYLPSQMPAALKPYRDDELRNLRGDDQQGPYQEHDRIYRYDVYNDLGE.......G
      241 ++      +             +                     ●+●   ●  300
Gm1  RPVLGGSSTFPYPRRGRTGRGPTVTDPNTEKQ....GEVFYVPRDENLGHLKSKDALEIG
Gm2  RPILGGSSTHPYPRRGRTGRYPTRKDQNSEKP....GEV.YVPRDENFGHLKSSDFLAYG
Gm3  RPVLGGNDTFPYPRRGRTGRKPTRKDPNSESR....SNDVYLPRDEAFGHLKSSDFLTYG
Hv2  RDVLGGSKDLPYPRRCRTGRKPSDSKPDHESRLLLLVQNVYVLRDELFGHLKQSDLLGYT
Hv1  RPILGGNSDHPYPRRGRTERKPNASDPSLESRLSLL.EQIYVPRDEKFGHLKTSDFLGYS
       ●   H2       +     H3       ++  +  H4      + 360
Gm1  TKSLSQIVQPAFESAFDLKSTPIEFHSFQDVHDLYEGGIKLPR....DVISTIIPLPVIK
Gm2  IKSLSQYVLPAFESVFDLNFTPNEFDSFQDVRDLHEGGIKLPT....EVISTIMPLPVVK
Gm3  LKSVSQNVLPLLQSAFDLNFTPREFDSFDEVHGLYSGGIKLPT....DIISKISPLPVLK
Hv2  LKGWLDGIILAIRTYVDL..SPGEFDSFADILKLYEGGIKLPNIPALEEVRKRFPLQLVK
Hv1  IKAITQGILPAVRTYVDT..TPGEFDSFQDIINLYEGGIKLPKVAALEELRKQFPLQLIK
      E10  +E11   + +                H6      ♦   +  E12     ++ 420
Gm1  ELYRTDGQHILKFPQPHVVQVSQSAWMTDEEFAREMIAGVNPCVIRGLEEFPPKSNLDPA
Gm2  ELFRTDGEQVLKFPPPHVIQVSKSAWMTDEEFAREMVAGVNPCVIRGLQEFPPKSNLDPT
Gm3  EIFRTDGEQALKFPPPKVIQVSKSAWMTDEEFAREMLAGVNPNLIRCLKDFPPRSKLDSQ
Hv2  DLIPKGGDFLLKLPKPEIIKVDQKAWMTDEEFAREMLAGVNPMMIKRLTEFPPKSTLDPS
Hv1  DLLPVGGDSLLKLPVPHIIQENKQAWRTDEEFAREVLAGVNPVMITRLTEFPPKSSLDPS
            +            H7      E13         H8      480
Gm1  IYGDQSSKITADSLD..LDGYTMDEALGSRRLFMLDYHDIFMPYVRQINQLNSAKTYATR
Gm2  IYGEQTSKITADALD..LDGYTVDEALASRRLFMLDYHDVFMPYIRRINQ.TYAKAYATR
Gm3  VYGDHTSQITKEHLEPNLEGLTVDEAIQNKRLFLLDHHDPIMPYLRRINA.TSTKAYATR
Hv2  KYGDHTSTMTEEHVAKSLEGLTVQQALAGNRLYIVDQHDNLMPFLIDINNLDASFVYATR
Hv1  KFGDHTSTITAEHIEKNLEGLTVQQALESNRLYILDHHDRFMPFLIDVNNLPGNFIYATR
```

FIGURE 22 B

```
        E14       +      E15       +      E16    +       +         H9          540
Gm1  TILFLREDGTLKPVAIELSLPHSAGDLSAAVSQVVLPAKEG.VESTIWLLAKAYVIVNDS
Gm2  TILFLRENGTLKPVAIELSLPHPAGDLSGAVSQVILPAKEG.VESTIWLLAKAYVVVNDS
Gm3  TILFLKNDGTLRPLAIELSLPHPQGDQSGAFSQVFLPADEG.VESSIWLLAKAYVVVNDS
Hv2  TLLFLRGDGTLAPVAIELSSPLIQGELTTAKSAVYTPQHAG.VEGWIWQLAKAYASVNDY
Hv1  TLFFLRGDGRLTPLAIELSEPIIQGGLTTAKSKVYTPVPSGSVEGWVWELAKAYVAVNDS
        541●     *●    *   H9                +H10     +   ●        H11       600+
Gm1  CYHQLMSHWLNTHAAMEPFVIATHRHLSVLHPIYKLLTPHYRNNMNINALARQSLINANG
Gm2  CYHQLMSHWLNTHAVIEPFIIATNRHLSALHPIYKLLTPHYRDTMNINALARQSLINADG
Gm3  CYHQLVSHWLNTHAVVEPFIIATNRHLSVVHPIYKLLHPHYRDTMNINGLARLSLVNDGG
Hv2  GWHQLISHWLNTHAVMEPFVIATNRQLSVTHPVYKLLHPHYRDTMNINARARGLLINAGG
Hv1  GWHQLVSHWLNTHAVMEPFVISTNRHLSVTHPVHKLLSPHYRDTMTINALARQTLINAGG
        601  H12           H13              +  H14  +   E     +      E       +660
Gm1  IIETTFLPSKYSVEMSSAVYKNWVFTDQALPADLIKRGVAIKDPSTPHGVRLLIEDYPYA
Gm2  IIEKSFLPSKHSVEMSSAVYKNWVFTDQALPADLIKRGVAIKDPSAPHGLRLLIEDYPYA
Gm3  VIEQTFLWGRYSVEMSAVVYKDWVFTDQALPADLIKRGMAIEDPSCPHGIRLVIEDYPYT
Hv2  VIEMTVFPHKHAMPMSSMVYKHWNFTEQALPADLIKRGMAVEDASSPHKVRLLIKDYPYA
Hv1  IFEMTVFPGKFALGMSAVVYKDWKFTEQGLPDDLIKRGMAVEDPSSPYKVRLLVSDYPYA
        661         H15                H16         H17     +  +         +    720
Gm1  ADGLEIWAAIKTWVQEYVPLYYARDDDVKNDSELQHWWKEAVEKGHGDLKDKPWWPKLQT
Gm2  VDGLEIWAAIKTWVQEYVSLYYARDDDVKPDSELQQWWKEAVEKGHGDLKDKPWWPKLQT
Gm3  VDGLEIWDAIKTWVHEYVFLYYKSDDTLREDPELQACWKELVEVGHGDKKNEPWWPKMQT
Hv2  TDGLAVWDAIEQWVSDYLTIYYPNDGVLQGDVELQAWWKEVREVGHGDLKDAAWWPKMQT
Hv1  ADGLAIWHAIEQYVSEYLAIYYPNDGVLQGDTEVQAWWKETREVGHGDLKDAPWWPKMQS
        721           H18     *     *●        +       ●       +      +  H19   780
Gm1  LEDLVEVCLIIIWIASALHAAVNFGQYPYGGLIMNRPTASRRLLPEKGTPEYEEMINNHE
Gm2  IEELVEICTIIIWTASALHAAVNFGQYPYGGFILNRPTSSRRLLPEKGTPEYEEMVKSHQ
Gm3  REELVEACAIIIWTASALHAAVNFGQYPYGGLILNRPTLSRRFMPEKGSAEYEELRKNPQ
Hv2  VAELIKACATIIWTGSALHAAVNFGQYPYSGYHPNKPSASRRPMPVQGSEEYAELERDPE
Hv1  VPELAKACTTIIWIGSALHAAVNFGQYPYAGFLPNRPTVSRRRMPEPGTEEYAELERDPE
        781         H20     H21●     ● ●        +         +          H22       840
Gm1  KAYLRTITSKLPTLISLSVIEILSTHASDEVYLGQRDNPHWTSDSKALQAFQKFGNKLKE
Gm2  KAYLRTITSKFQTLVDLSVIEILSRHASDEVYLGQRDNPHWTSDSKALQAFQKFGNKLKE
Gm3  KAYLKTITPKFQTLIDLSVIETLSRHASDEVYLGERDNPNWTSDTRALEAFKRFGNKLAQ
Hv2  KAFIRTITSQFHALVGISLMEILSKHSSDEVYLGQHDTPAWTSDAKALEAFKRFGAKLEG
Hv1  RAFIHTITSQIQTIIGVSLLEVLSKHSSDELYLGQRDTPEWTSDPKALEVFKRFSDRLVE
        841                  ++    +        +         +      +  +   895*
Gm1  IEEKLVRRNNDPSLQGNRLGPVQLPYTLLYPSSEE......GLTFRGIPNSISI
Gm2  IEEKLARKNNDQSL.SNRLGPVQLPYTLLHPNSE.......GLTCRGIPNSISI
Gm3  IENKLSERNNDEKLR.NRCGPVQMPYTLLLPSSKE......GLTFRGIPNSISI
Hv2  IEKQVVAMNSDPQLK.NRTGPAKFPYMLLYPNTSDHTGQAEGLTARGIPNSISI
Hv1  IESKVVGMNHDPELK.NRNGPAKFPYMLLYPNTSDHKGAAAGLTAKGIPNSISI

Gm1 SEQ ID NO:15        ¤The numbering system shown above
Gm2 SEQ ID NO:16         the sequence alignment does not
Gm3 SEQ ID NO:17         correspond to the actual amino
Hv2 SEQ ID NO:18         acid number of any lipoxygenase
Hv1 SEQ ID NO:9          sequence in the alignment.
```

LOW LIPOXYGENASE 1 BARLEY

FIELD OF THE INVENTION

This invention is in the field of plant biotechnology. More specifically, the invention relates to a mutant barley lipoxygenase 1 gene (lox-1) that encodes an enzyme with severely reduced 9-hydroperoxy-octadecadienoic acid forming activity. The invention also relates to the use of barley cultivars homozygous for mutated lox-1 in brewing processes to reduce the formation of off-flavors in brewed products, such as beer, during storage.

BACKGROUND OF THE INVENTION

Lipoxygenases are a family of enzymes (EC 1.13.11.12) that catalyze the dioxidation of free and esterified polyunsaturated fatty acids containing a 1(Z), 4(Z)-pentadiene configuration. The products of lipoxygenase-catalyzed reactions have long been suspected as major culprits for the appearance of stale flavors in plant grain/seed and grain/seed derived food products (Robinson et al., 1995, *Food Chem.,* 54: 33–43). Lipoxygenases have been implicated in the production of volatile hexanal aldehydes generated during soybean processing, which have an undesirable aroma, limiting the use of soybean proteins in food products. Three lipoxygenase isozymes expressed in soybean seed are believed to contribute to lipid oxidation and hexanal formation. Soybean mutants lacking one or more of these isozymes have been generated with the aim of reducing hexanal formation and improving their flavor stability. The success of this approach has been evaluated by Hildebrand et al., 1990, *J. Agric. Food Chem.* 38: 1934–1936. Mutants lacking soybean lipoxygenase 3 produced higher hexanal levels, suggesting that this isozyme diverts 13-hydroxyperoxyoctadecanoids, produced by lipid oxidation, towards non-volatile products. The field performance of triple-null soybean lines, lacking all three seed lipoxygenases, has shown that these enzymes are not essential for normal agronomic and seed characteristics (Narvel et al., 1998, *Crop Sci.* 38: 926–928).

Lipoxygenases have also been implicated in the generation of off-flavors in rice, which can occur during grain storage. The release of free fatty acids can be detected in stored grain, which is indicative of the metabolism of the triglyceride reserves. The rice variety Daw Dam was found to accumulate lower levels of pentanals and hexanals giving a better flavor stability on storage (Susuki et al., 1999, *J. Agric. Food Chem.,* 47: 1119–1124). This desirable phenotype was attributed to the absence of rice lipoxygenase-3, which oxidizes unsaturated lipid acyl chains to form 9-hydroperoxyoctadecadienoic positional isomers.

It is recognised that the lipoxygenase pathway is complex with many branches and its role in numerous aspects of plant growth and physiology are not fully understood. Modifications of the lipoxygenase pathway which alter 9-hydroperoxidation activity in seed crops are proposed to regulate their susceptibility to mycotoxin contamination by Aspergillus spp. (WO 9726364), which is consistent with the involvement of this pathway in plant pathogen resistance, but is not related to the aims of the invention herein described.

Among the many aroma volatiles which contribute to the flavor of beer, the higher unsaturated aldehydes with a 6–12 carbon chain have particularly low organoleptic flavor thresholds (Meilgaard 1975, *MBAA Tech. Quart.* 12: 151–168). Trans-2-nonenal, which is a member of this group, has both an extremely low flavor threshold of 0.11 ppb and contributes an unpleasant straw-like, "cardboard" flavor to the beer. The characteristic off-flavor caused by trans-2-nonenal is a common characteristic of beers stored for 1–3 months or more and is particularly detrimental to the flavor of lager beer, which is brewed with light malts and has a delicate flavor.

Sulfite has long been known to improve the flavor stability of beer, not only by binding oxygen and acting as an anti-oxidant, but also by forming volatile bisulfite addition compounds with aldehydes and ketones present in the beer. The two major sources of sulfite in beer are sulfite produced by yeast during fermentation via the sulfur assimilation pathway and sulfite added to the beer prior to packaging. Fermentation conditions that enhance yeast sulfite production and secretion will allow the formation of sulfite-carbonyl adducts from carbonyls present in the wort and prevent their further metabolism by the yeast (Dufour 1991, *Proc.Eur. Brew. Conv. Congr.,* Lisbon, pp. 209–216). In this manner carbonyls such as acetaldehyde and diacetyl may be transferred to the beer. The ability of sulfite to prevent the appearance of the carbonyl compound trans-2-nonenal during beer aging has been demonstrated by brewing beer with a yeast strain blocked in the sulfur assimilation pathway (Johannesen et al., 1999, *Proc.Eur. Brew. Conv. Congr.,* Nice, pp. 655–662). Following bottling, the beer was subjected to forced aging by storing it at 37° C. for 7 days, after which trans-2-nonenal levels were found to be well above the taste-threshold. If 10 ppm sulfite was added to the low-sulfite beer just prior to bottling, the appearance of trans-2-nonenal during forced aging was significantly reduced. The reaction between sulfite and carbonyl compounds is reversible and under thermodynamic and kinetic control. The apparent equilibrium constants for bisulfite compounds ranges from $10^{-6}$ M for carbonyl compounds such as acetaldehyde, hexanal, and decanal, to $10^{-3}$ for diacetyl and pyruvate (Dufour 1991, supra). During beer storage, gas exchange through the packaging will allow oxygen into the beer and sulfite will be lost, such that weaker bisulfite adducts will dissociate, allowing free carbonyls to appear in the beer. While sulfite unquestionably enhances the flavor-stability of beer, particularly in the short-term, its retention in packaged beer is strongly dependent on gas exchange through the packaging and temperature. In a finished beer the natural levels of sulfite produced during fermentation are variable and the addition of sulfite prior to bottling is not a universally accepted practice. For these reasons sulfite alone does not provide a reliable method to enhance the long-term flavor-stability of beer under the different beer storage conditions used around the globe.

It is generally accepted that the trans-2-nonenal found in beer results from the oxidation of polyunsaturated fatty acids derived from barley grain lipids, where the 18-carbon chain fatty acid, linoleic acid [classified as an 18:2,n-6 polyunsaturated fatty acid (Broun, Gettner and Sommerville 1999, *Annu. Rev. Nutr.* 19: 197–216)] is the most abundant. However, there is little agreement in the literature as to the mechanism whereby trans-2-nonenal is formed. The presence of enzymatic pathways leading to trans-2-nonenal formation from poly-unsaturated fatty acids has been proposed, but the individual enzymatic steps have never been demonstrated experimentally in barley grain or during the malting process (Gardner 1988, *Adv. Cereal Sci. Technol.* 9: 161–215). The concept of using anti-sense or co-suppression gene technology to reduce lipoxygenase-1 levels in barley grain, and thereby control 9-hydroperoxidation and reduce aldehyde and alcohol levels in the finished barley grain, has been proposed as a means to control off-flavor formation, but results of such an approach are not reported (McElroy and Jacobsen, 1995, Bio/Technology 13: 245–249).

A forcing test has been developed as a method for assessing the trans-2-nonenal potential of a beer, where trans-2-nonenal formation in wort or beer is induced by subjecting samples to elevated temperatures at reduced pH, (100° C., at pH 4.0 for 2 hours). Attempts to correlate the trans-2-nonenal potential in wort and finished beer with the total level of lipoxygenase activity in the kilned malt have indicated that lipoxygenase may contribute to the appearance of trans-2-nonenal in aged beer (Drost et al., 1990, J. Am. Soc. Brew. Chem. 48: 124–131). The conclusions that can be drawn from this study, however, are severely limited by the fact that the lipoxygenase activity in the barley malt was regulated at the end of the malting process by the degree of enzyme inactivation during kiln drying. Thus, only the effect of the residual malt lipoxygenase activity on the trans-2-nonenal potential in the derived wort and finished beer was examined. The study failed to evaluate the lipoxygenases that catalyse the first step in the lipoxygenase enzymatic pathway in the barley grain during development and malting, and their role as determinants of trans-2-nonenal levels found in beer. Indeed, the absence of barley cultivars deficient in one or more lipoxygenase isoenzyme has made it impossible to provide convincing evidence for the role of the lipoxygenase pathway in barley malt in controlling the formation of trans-2-nonenal. Such experiments are needed to evaluate the contribution of enzymatic, as compared to auto-oxidative/chemical pathways, to the formation of trans-2-nonenal in beer. The brewing process involves a high temperature step of wort boiling where these non-enzymatic reactions are proposed to occur (Noël et al., 1999, J. Agric. Food Chem. 47: 4323–4326).

SUMMARY OF THE INVENTION

This invention provides a barley cultivar having greatly reduced lipoxygenase-1activity. In one embodiment, the barley plants of the invention contain a mutant lox-1 gene expressing greatly reduced levels of the isoenzyme lipoxygenase-1. In an alternative embodiment, the barley plants contain a heterologous nucleic acid sequence expressing an antisense sequence to the wild-type lox-1, thereby reducing the enzyme's activity.

As shown herein, malt and wort produced from the reduced lipoxygenase barley of the invention, for example, from barley cultivars homozygous for a mutant lox-1 gene, are useful to produce beer with significantly enhanced flavor stability and reduced trans-2-nonenal levels, particularly under conditions known to promote the appearance of T2N. The invention demonstrates a correlation between the activity of barley malt lipoxygenase-1 to produce 9-hydroxyperoxy-octadecadienoic acids (9-HPOD), and the presence of trans-2-nonenal in beer. The invention further demonstrates that the use of barley homozygous for the mutant lox-1 gene in the brewing process improves the flavor stability of the beer, both during storage and on exposure to elevated storage temperatures. These properties enhance the quality of the beer, and are useful to extend its shelf-life and reduce the need to cool beer during transport and storage.

The invention provides barley plants and portions thereof having reduced lipoxygenase-1 activity, including barley plants expressing mutant LOX-1 protein as described herein, as well as methods for producing such barley plants, plant portions, products of the plants, and particularly malt and beer products produced from the barley plants of the invention.

BRIEF DESCRIPTION OF THE DRAWINGS

FIGS. 12A–12G are a nucleotide sequence alignment of the promoter and transcribed region of the lox-1 wild-type cv Vintage allele (WT) and the Line G allele (LG). The transcription start site (+1), ATG start codon (+69) and translation stop codon (+4231) in the gene sequences are underlined. Nucleotide mutations identified in the Line G allele are shown in bold italics and indicated by an asterisk.

FIG. 13 is a schematic presentation of the lox-1 gene of cv Vintage (wild-type) and the mutant lox-1 gene of Line G. The transcript from +1 to +4375 is composed of 7 exons (stippled boxes) and 6 introns (white boxes). Two mutations in the lox-1 gene are indicated.

FIGS. 22A–22B are a comparative alignment of amino acid sequences of soybean lipoxygenases LOX-1 (Gm1), LOX-2 (Gm2), LOX-3 (Gm3), and barley lipoxygenases LOX-1 (Hv1) and LOX-2 (Hv2).

DETAILED DESCRIPTION OF THE INVENTION

Figure 1:
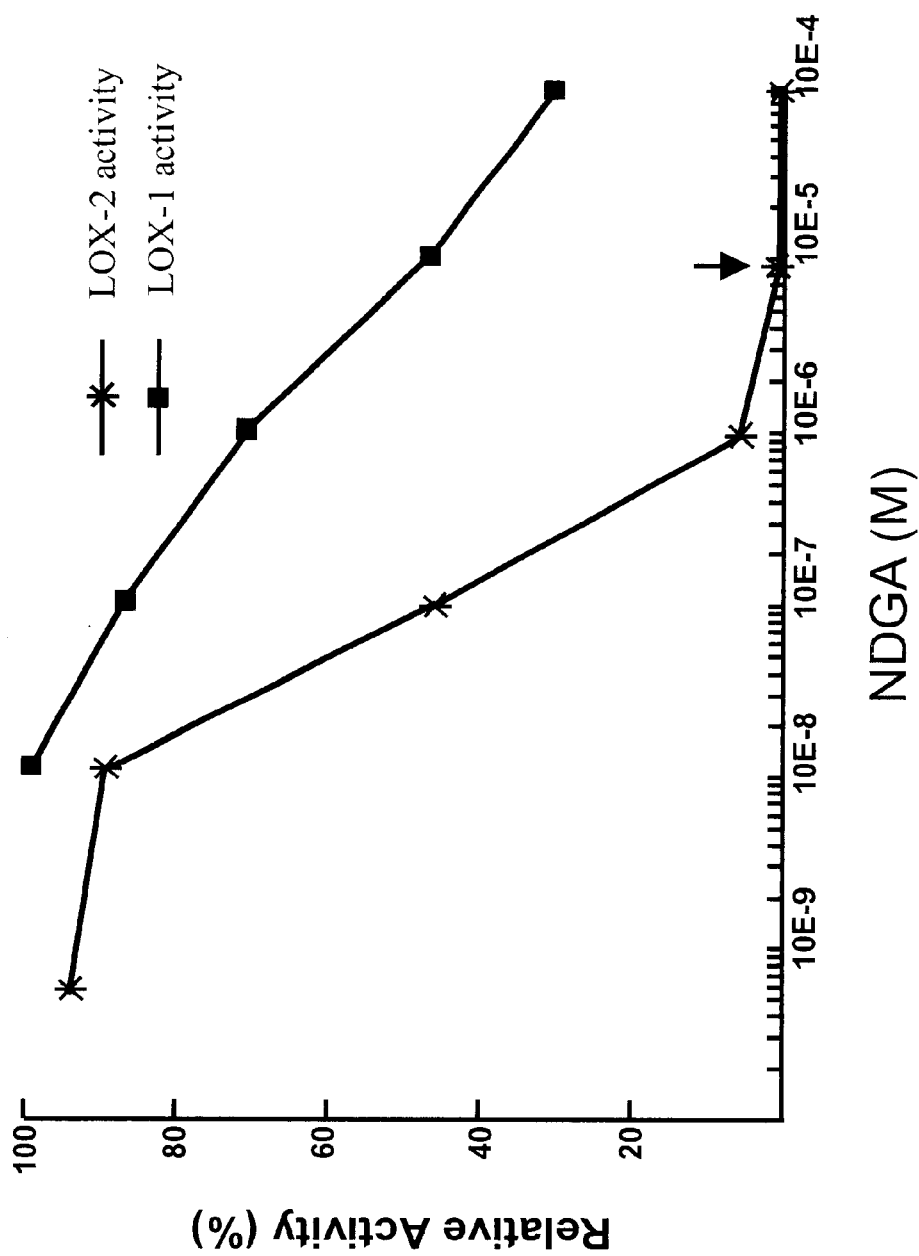
FIG. 1 is a graph showing the effect of the inhibitor nordihydroguaiaretic acid (NDGA) on immuno-affinity purified lipoxygenase 1 and 2 activity from embryos of 3 day germinated barley grain.

In accordance with the subject invention, plant materials, plant products, and methods are provided for producing a beverage, such as beer, the beverage having a reduced content of the off-flavor compound trans-2-nonenal, such that the flavor stability of the beverage, e.g., beer, during storage and on exposure to elevated temperatures is improved, relative to a control beverage. More particularly, the invention provides barley varieties whose developing and germinating grain produce greatly reduced activity levels of the enzyme lipoxygenase-1, denoted LOX-1, which, for example, when used in a beer brewing process, results in a beer having reduced trans-2-nonenal levels, as compared with a control barley variety.

The methods used to generate, characterize, and validate a barley variety having greatly reduced LOX-1 activity, and use of this type of barley for the production of flavor-stable beer are described below.

1. Definitions

As used herein, the following terms have the indicated definitions:

"Plant portion" means a plant or specific part of a plant, such as the stem, leaves, roots, flowers, seeds, grains, fruits, or buds.

"LOX-1" means lipoxygenase-1 protein; "lox-1" means the gene encoding LOX-1.

"Mutant barley lox-1" means a mutagenized barley gene encoding a mutant lipoxygenase 1 polypeptide.

"Non-mutated control" means a plant, nucleic acid, gene, polypeptide, plant portion, or plant product containing wild type gene or protein.

"Heterologous" means a non-native sequence, e.g., a sequence derived from another species, or a recombinantly engineered or synthetic sequence that differs from the native sequence.

"Plant product" means a product resulting from the processing of a plant or plant portion, and includes, for example, malt and wort.

"Acidic amino acid" means aspartic or glutamic acid.

"Basic amino acid" means histidine, lysine, or arginine.

"Polar amino acid" means threonine, serine, tyrosine, tryptophan, asparagine, or glutamine.

"Organoleptic properties" means properties appealing to the olfactory and taste senses that are analysed, for example, by a trained taste panel.

"Brewed product" means a product prepared by mashing, boiling, and fermenting, e.g., beer.

"Reduced trans-2-nonenal" means less than about 50%, as compared with wild-type (control) conditions.

2. Lipoxygenase Activity

Lipoxygenase enzymes catalyze the oxidation of polyunsaturated fatty acids. In barley, the isoenzymes LOX-1 and LOX-2 are known. LOX-1 primarily catalyzes 9-hydroperoxidation, whereas LOX-2 primarily catalyzes 13-hydroperoxidation of polyunsaturated octadecanoic fatty acids. The data shown in the Examples below demonstrates a correlation between barley LOX-1 9-hydroperoxidation activity and the presence of trans-2-nonenal in beer. Accordingly, barley having reduced LOX-1 activity is useful to produce beer having a reduced trans-2-nonenal level and/or potential as compared with a control.

3. Production of Low Lipoxygenase Barley

A variety of known genetic approaches can be used to produce the plants of the invention, that is, to reduce the level of lipoxygenase 1 enzyme activity expressed in a barley plant in a stable, inheritable manner. These approaches include, but are not restricted to antisense technology and mutagenesis, such as chemical and radiation induced mutagenesis, as well as site-directed mutagenesis.

Barley Transformation

Barley can be transformed with various nucleic acid molecules designed to manipulate lox-1 gene expression or alter the architecture of the lox-1 gene. Various methods, for example, *Agrobacterium tumofaciens*-mediated transfer (Tingay et al, 1997, *Plant J.*, 11: 1369–1376), particle bombardment (Wan and Lemaux, 1994, *Plant Physiol.*, 104: 37–48, or polyethylene glycol (PEG)-mediated DNA uptake (Funatsuki and Kihara, 1995, *Theor. Appl. Genet.*, 91:707–712), can be used to successfully introduce nucleic acids into a barley cell, for example into a protoplast, callus, or an embryo.

Various promoters can be used to drive expression of the gene of interest. For expression of lox-1-containing vectors, including antisense sequences, the native lox-1 promoter region can be used. The promoter sequence of lox-1 is contained in nucleotides 2602–3511, which includes the 5' UTR of EMBL accession no. U83904. Alternatively, promoters that drive expression of the gene of interest constitutively, for example the Ubi.1 maize ubiquitin promoter, can be used (Wan and Lemaux, Supra; Kjæwrulff et al., in P. Mathis, Ed., 1995, *Photosynthesis: from Light to Biosphere*, Vol. II, 151–154). Expression vectors can also contain a transcription termination region, for example, the 3' terminator of the nopaline synthase gene (3'-nos) (Bevan, et al, 1983, *Nucl. Acids Res.*, 11: 369–385) has been fused to genes expressed in transgenic barley (Wan and Lemaux, Supra; Funatsuki and Kihara, Supra).

Expression vectors can also contain a gene that allows for selection of transformed cells when the vector has been successfully integrated in the cell. These genes can encode antibiotic or herbicide resistance genes, for example the neomycin phosphotransferase (npt) or the phosphinothricin acetyl transferase (bar) gene. When expressed, such resistance genes allow for growth of the transformed cell in neomycin-or bialaphos-containing media, respectively (See, for example, Wan and Lemaux, Supra; Funatsuki and Kihara, Supra; Kjærulff et al., in P. Mathis, Supra).

Following transformation, cells can be grown in selective media for a period of time and then cultured to allow for the formation of shoots, followed by root systems, and then plantlets. A successful barley transformation procedure was developed by Funatsuki and Kihara, (Supra), where transformation of barley protoplasts by PEG with neomycin phosphotransferase-containing expression vectors and subsequent selection in neomycin yielded fertile plants containing the transgene. The transgene was shown to integrate into the genome and most of the transgenic plants expressed the protein encoded by the transgene. These transgenic plants also were able to transmit and express the transgene following crosses.

It is understood that a variety of transformation methods, expression vectors, promoters, selectable markers, and the like are known and useful for transformation of barley.

Barley Mutagenesis

The lox-1 gene can be targeted for site-specific mutagenesis using chimeric RNA/DNA oligonucleotides. These chimeric RNA/DNA oligonucleotides have been shown to successfully introduce mutations in plant cells (Zhu et al., 1999, *Proc. Natl. Acad. Sci.* 96: 8768–8773; and Beetham et al., 1999, *Proc. Natl. Acad. Sci.* 96: 8774–8778) and mammalian cells (Yoon et al., 1999, *Proc. Natl. Acad. Sci.* 93:2071–2076) at desired locations. The chimeric RNA/DNA oligonucleotides can be transformed into the barley protoplasts or cells of interest in a variety of ways, for example using the PEG-mediated or particle bombardment-mediated transformation methods described above. The individual protoplasts or cells can then regenerated by tissue culture to whole fertile plants, and the mutational event can be confirmed and followed, for example using a PCR-based approach as detailed in the Examples below.

This site-directed mutagenesis method can be applied to mutate specific residues in the lox-1 gene. The lox-1 gene can be mutated at one or more nucleotide position in the promoter region to downregulate or abolish lox-1 transcription. Specific mutagenesis can also be applied to introduce changes in the lox-1 coding region that, for example, reduce the enzyme's activity. Such mutations include, but are not limited to, insertions, deletions, and substitutions resulting in a frameshift, truncation of the LOX-1 protein, and/or alteration of the neutral and hydrophobic nature of the enzyme's substrate cavity.

Antisense Expression

Reduction in lox-1 expression can also be accomplished by expression of a lox-1 antisense construct in the barley cells. Methods for the expression of antisense constructs in barley to reduce the expression of a targeted protein have been reported, for example, in Gilpin, M. J. et al., 1998, In: *Photosynthesis: Mechanisms and Effects*, G. Garab, ed., Vol. IV, 2983–2986; Kjærulffet al., 1995, In: *Photosynthesis: from Light to Biosphere*, P. Mathis, Ed., Vol. 11, 151–154.

Barley cells can be transformed with an expression construct containing an antisense nucleic acid sequence. The expression construct produces an antisense RNA molecule capable of specifically binding to at least a portion of the mRNA produced from the wild type lox-1 gene, through complimentary base pairing, and capable of disrupting the splicing of the pre-mRNA or translation of this mRNA. A constitutive or tissue/temporal specific promoter, for example, the barley lox-1 promoter described above, can drive expression of the antisense nucleic acid sequence.

Chemical Mutagenesis

The chemical mutagen sodium azide ($NaN_3$) has commonly been used for barley mutagenesis and is known to induce stable mutations in the DNA (deoxyribonucleic acid) sequence of the barley genome (Olsen et al., 1993, *Proc. Natl. Acad. Sci. USA*, 90: 8043–8047). Other chemical mutagens, for example, ethyl methanesulfonate (EMS), azidoglycerol (AG, 3-azido-1,2-propanediol), methyl nitrosourea (MNU), and maleic hydrazide (MH) can also be used to induce DNA mutations (Rank, J. et al., 1997, *Mutat. Res.* 390:121–7), as can UV irradiation.

As shown in the Examples below, the grain of the barley cultivars (cv) Vintage and Caruso were treated with sodium azide and propagated by self-fertilization through to the $3^{rd}$ generation (M3).

4. Identification and Selection of Low Lipoxygenase Barley

Identification and selection of barley plants having reduced lipoxygenase isoenzyme activity in the grain can be achieved, for example, by analysis of lipoxygenase activity. Enzymatic assays can be used to determine the activity of the two major lipoxygenases known to be present in either mature or germinating grain, LOX-1 and LOX-2. Such assays should distinguish LOX-1 activity from that of LOX-2.

One selective assay of LOX-1 and LOX-2 is based on the oxidation of a poly-unsaturated fatty acid by lipoxygenase and the spectrophotometric detection of the hydroperoxide product of such oxidation. The specificity of this assay for LOX-1 takes advantage of the comparative insensitivity of LOX-1 to an inhibitor, for example, NDGA, relative to LOX-2.

Selective assay can also be achieved using immunoprecipitation to selectively remove LOX-1 or LOX-2 from the assay. Specific anti-LOX-1 and anti-LOX-2 antibodies, for example, monoclonal antibodies, can be prepared from purified LOX-1 or LOX-2 as described in Holtman et. al, 1996, Supra.

These assay methods can be adapted for microtiter plate assay procedures, or other known repetitive, high throughput assay formats, allowing the rapid screening of many samples. These assays can be validated for screening leaf tips of germinating grain in a non-destructive manner, such that seedlings selected in the screen can be further propagated.

The loss of LOX-1 activity in putative mutants can be confirmed by assay of enzymatic activity. For example, grain extracts can be incubated with linoleic acid and the oxidation products of linoleic acid analyzed, for example, by reverse phase HPLC. The relative amounts of 9-HPOD and 13-HPOD formed from linoleic acid provides a measure of LOX-1 activity, whose major product is 9-HPOD.

As shown in the Examples below, approximately 20,000 grain of the M3 generation of mutagenized cv Vintage and cv Caruso were screened for LOX-1 and LOX-2 activity by oxidation assay in the presence of inhibitor and also by immunoprecipitation assays. Using these screening methods, a mutant in cv Vintage was found having a major reduction in LOX-1 activity, and was denoted Line G. The mutant phenotype was inherited in the M4 and M5 generations.

Seed produced from the Line G barley was deposited on Jan. 4, 2001 with the National Collections of Industrial, Food and Marine Bacteria (NCIMB), 23 St. Machar Drive, Aberdeen, AB243RY, Scotland, UK, under the terms of the Budapest Treaty, as Accession Number: NCIMB 41078.

5. Genetic Sequences

A precise description of the genotypic alteration that accounts for the low-lipoxygenase phenotype in barley plants of the invention is useful for identifying plants having this genetic alteration and for crossing this genetic character into other barley cultivars in a breeding program. A variety of known molecular and biochemical methods can be used to determine the genetic basis for the low lipoxygenase phenotype.

It is generally recognized that both cis-acting and trans-acting genetic sequences can determine the expression of a given gene in the genome and the activity of the gene product. Control points in gene expression include the regulation of the timing, tissue-specificity and rate of gene transcription, the stability of the transcript and the rate of transcript translation. Both the level of gene expression and the stability and specific activity of the encoded enzyme will determine the level of enzyme activity detected in a tissue.

Alterations in a plant gene sequence can be determined by DNA sequencing of known relevant parts of the genome, while Northern analysis provides a tool to monitor stable transcript levels in a given plant tissue. Enzyme expressed in plant tissue can be evaluated by extracting the enzyme from the tissue and measuring the enzymatic activity.

As shown in the Examples below, the identity of the genetic changes that determine the low-lipoxygenase phenotype of the Line G mutant induced in cv Vintage were determined in the following manner. The structural gene encoding the LOX-1 protein, both in the parent cv Vintage and in the Line G, was amplified by the polymerase chain reaction (PCR), and the upstream promoter sequences, which regulate expression of the gene, as well as the entire coding sequence, comprising intron and exon sequences, were sequenced.

Comparison of the nucleotide sequences of the lox-1 gene from Line G and from wild-type cv Vintage revealed 2 nucleotide substitutions in 2 exons, of which one (at position +2347) led to a non-conservative amino acid substitution (Glycine$^{368}\rightarrow$ Aspartate) in the expressed protein.

FIG. 22 shows an alignment of soybean (Gm: *Glycine max L*) lipoxygenases LOX1 (Acc. No. P08170), LOX2 (Acc. No. P08170), LOX3 (Acc. No. AAB41272) and barley (hv: *Hordeum vulgare*) lipoxygenases LOX1 (Acc.No. P29114) and LOX2 (Acc. No. AAB70865.1). Conserved amino acid residues and conservative substitutions of charged residues are shown in bold. Secondary structure assignments for LOX3 of soybean *Glycine max*, where H=alpha helices and E=Beta strands, are shown above the alignment, and residues relevant to enzyme function (identified by an asterix or filled circle) are shown, as described in Skrzypczak-Jankun et.al., 1997, *Proteins* 29:15–31.

Amino acid residues that participate in non-heme iron binding or essential for catalysis (*) in soybean LOX3 include: $H_{518}$, $H_{523}$, $H_{709}$ [3 N atoms]; $N_{713}$, $I_{857}$. The equivalent residues in barley LOX 1 are H517, $H_{522}$, $H_{708}$, $N_{712}$, and $_{1862}$. Residues in soybean LOX3 with a predicted role in catalysis(•) are: $H_{266}$, $H_{513}$, $H_{776}$, $F_{264}$, $F_{272}$, $F_{714}$, $W_{519}$, $R_{552}$, $R_{726}$, $D_{766}$, $D_{779}$, $K_{278}$. The equivalent residues in barley LOX1 are: $H_{261}$, $H_{512}$, $H_{775}$, $F_{259}$, $F_{267}$, $F_{713}$, $W_{518}$, $R_{551}$, $R_{725}$, $D_{778}$, and $K_{273}$.

Proline ($P_{86, 109, 167, 171, 223, 234, 291, 311, 324, 343, 345, 371, 381, 382, 486, 541, 548, 600, 616, 627, 685, 726, 734, 788, 829, 833, 839, 857}$) and glycine ($G_{49, 67, 68, 70, 91, 107, 137, 187, 192, 210, 217, 218, 260, 306, 307, 336, 392, 409, 458, 474, 490, 569, 607, 674, 676, 720, 736, 783, 828, 850, 855}$) residues (+) located in loops and helix-capping positions in protein secondary structures, may facilitate sharp turns and folding of the peptide backbone.

Alignment of related plant lipoxygenases indicated that the Glycine-368 in barley LOX-1 is strongly conserved. Furthermore, this residue, which corresponds to Glycine-353 in soybean LOX-1, is one of 35 highly-conserved residues out a total of 58 residues that line the substrate cavity II of the enzyme, as seen from its crystal structure. These conserved residues are highlighted (boxes) in the alignment of plant lipoxygenase sequences shown in FIG. 22 (Minor et.al., 1996, *Biochemistry* 35:10687–10701), and include the following barley LOX-1 residues: $Y_{224}$, $L_{268}$, $W_{355}$, $E_{364}$, $G_{368}$, $V_{369}$, $N_{370}$, $I_{374}$, $L_{424}$, $L_{499}$, $K_{501}$, $A_{502}$, $V_{504}$, $D_{508}$, $S_{509}$, $H_{512}$, $Q_{513}$, $L_{514}$, H517, W518, $H_{522}$, $I_{556}$, $L_{559}$, $A_{560}$, $L_{564}$, $I_{565}$, $I_{570}$, $T_{574}$, $S_{585}$, $Q_{715}$, $Y_{718}$, $N_{724}$, $R_{725}$, $P_{726}$, $T_{727}$, $L_{772}$, and $I_{862}$. All but 7 of the 35 conserved residues are neutral or hydrophobic residues. The substitution of a charged residue at position Glycine-368 in barley or at another conserved neutral or hydrophobic residue lining the substrate cavity II, is likely is likely to disturb the structural and functional properties of the enzyme. The G$\rightarrow$$D_{368}$ mutation in barley Line G LOX1(♦)is located between alpha-helix H6 and beta-strand E12.

As shown in FIG. 22, the lipoxygenase family of enzymes shares a high degree of sequence conservation, which is reflected in their conserved secondary structure, determined for several members of the plant lipoxygenase family including soybean LOX1 and LOX3 (Skrzypczak-Jaikun et al., 1997, supra). Barley LOX1 shares 56.9% sequence identity and 67.8% sequence similarity with soybean LOX3. Several amino acid residues in the soybean LOX3 isoenzyme have been identified as ligands for the non-heme iron, or are suggested to be essential for its activity (denoted by * ●). In view of the high sequence conservation between the barley LOX1 and the soybean LOX3, it is reasonable to predict that residues in the barley LOX1 sequence that are homologous to those identified as important for the function of LOX3 may also be essential for enzymatic activity. Thus, non-conservative amino acid substitutions at any of these positions, including substitutions of those residues in barley LOX1 corresponding to the 35 highly conserved residues of soybean LOX3 that line the substrate cavity and in other positions essential for enzyme activity, are likely to reduce lipoxygenase activity.

The amino acid residues proline and glycine are known to facilitate turns in a peptide backbone when they are located between secondary structural elements, which allow a protein to assume a folded tertiary structure. Proline and glycine residues are also common in helix capping motifs (Parker and Hefford, 1997, *Protein Eng.*, 10: 487–496, http://www.expasy.ch). The single non-conservative substitution in Line G LOX1, where a glycine located between two predicted structural elements was replaced by aspartate, led to a significant loss of enzyme activity. It is thus predicted that mutation in the LOX-1 gene causing a non-conservative amino acid substitutions at one or more of the proline or glycine residues in the barley LOX1, located in regions outside the structural elements, may similarly prevent folding of the native protein and consequently reduce the activity of the encoded enzyme.

Thus, in one embodiment, a useful mutant barley plant of the invention having reduced lipoxygenase 1 activity contains a mutated nucleic acid sequence that alters the neutral or hydrophobic nature of the substrate cavity of the enzyme by insertion of one or more acidic, basic, or polar amino acids. For example, a useful nucleic acid sequence [SEQ ID NO: 11 encodes a barley LOX-1 protein [SEQ ID NO: 12] having a substitution at amino acid 368 from Glycine to Xaa, where Xaa is an acidic, basic, or polar amino acid. One specific amino acid sequence of the barley mutant LOX-1 of the invention is that where Xaa is aspartic acid, e.g., Line G.

As shown in the Examples below, the genotypic changes in Line G had no detectable influence on lox-1 gene expression, but the LOX-1 activity detected in mature and germinating grain of Line G were approximately 9% of that detected in grain of the parent line, cv Vintage. In order to provide direct evidence that the amino acid mutation in LOX-1 of Line G was responsible for the low-LOX-1 phenotype, the coding sequence of Line G lox-1 and cv Vintage lox-1 were expressed transiently in protoplasts from barley aleurone, and the activity of the mutant LOX-1 enzyme was shown to be strongly reduced in comparison to the wild-type LOX-1 enzyme.

6. Transfer Between Breeding Lines

The detection of alterations in genetic character of the barley plants of the invention genotype is useful to identify the presence of a specific genetic character in a barley line, and to facilitate the transfer of this character between breeding lines in a breeding program. A variety of molecular tools are available for the detection of alterations in genomic sequence. Such methods include, but are not restricted to, detection of restriction fragment length polymorphisms (Gebhardt and Salamini 1992, *Int. Rev. Cytology.*, 135: 201–237) and quantitative PCR based detection methods such as amplification using fluorescent primers, e.g. the TaqMan primer probe systems (Ibraham et al., 1998, *Anal. Chem* 70, 2013–2017). The choice of detection method will depend on the specific genetic character but should preferably be rapid and provide clearly interpretable data.

As shown in the Examples below, a PCR-Cleavage Amplified Polymorphic Site assay (PCR-CAPS) was provided for the detection of the mutant lipoxygenase-1 gene of Line G. The nucleotide substitution in the lox-1 gene in Line G at position +2347 introduced an additional site of recognition by the AatII restriction endonuclease that can be detected by the PCR-CAPS assay. Suitable detection methods for lox-1 are not restricted to this assay, but can equally well be based on TaqMan technology, and other known detection methods.

Also shown in the Examples below, the PCR-CAPS assay was applied to 4 generations of breeding material from a back-cross program, where the low-lipoxygenase phenotype in Line G was systematically back-crossed into cv Alexis. Inheritance of the low-lipoxygenase phentoype was shown to follow the inheritance of the lox-1 gene, and the phenotype was identified as recessive and only seen in lines homozygous for the lox-1 gene.

Accordingly, plant progeny of the invention includes breeding lines, for example, derived in a back-crossing program, that contain mutant lox-1 and express a low lipoxygenase phenotype.

7. Brewing

The barley plants of the invention, including plant parts, plant progeny, grain, and plant products such as malt and wort, having low lipoxygenase 1 activity, are demonstrated herein to be useful for the manufacture of a beverage having reduced levels of free trans-2-nonenal over a measured period of time, or under conditions of elevated storage temperature, as compared to a beverage produced from a wild-type control barley variety. For the purpose of these comparisons the sulfite content of the beer is controlled to 5 ppm or below, since it is recognised that higher sulfite levels at the time of bottling will temporarily delay the appearance of free trans-2-nonenal. For example, beer brewed from malt derived from the mutated barley Line G described herein, possessed stabilized organoleptic properties over a measured period of time as compared with beer brewed from malt derived from a control, non-mutated barley.

Brewing trials and evaluation of bottled beer provide the best method for evaluating the influence of different ingredients on the quality and stability of the finished beer. In order to test the influence of different barley malts, sufficient barley grain is needed to perform the malting and brewing trials on a pilot scale and semi-industrial scale. During the period of barley propagation, the field performance of the barley line can be evaluated. The malting properties of a barley line can be evaluated during pilot or industrial scale malting, and should preferably lie within national malting quality recommendations eg. the European Brewing Convention recommendations for malting quality (Analytica-EBC/European Brewing Convention, 1998, Publ. Hans Carl Geträdnke-Fachverlag, Nürnberg, Germany). Following pilot or semi-industrial scale brewing, the beer is packaged in brown bottles and cooled to 5° C. for optimal storage. At this stage the fresh beer can be analysed by trained taste panels able to detect specific beer flavors, including the off-flavor compound trans-2-nonenal. Additionally, the beer is chemically analysed for major flavor components including trans-2-nonenal. These methods of beer quality analysis are then repeated on the beer following various storage conditions known to reveal the long-term storage stability of the beer, for example, forced aging treatments.

As shown in the Examples below, Line G barley was propagated in the field over several seasons in order to malt 10 tons of this line in an industrial malthouse. The control barley varieties cv Vintage and cv Nevada, both having the wild-type LOX-1 phenotype, were malted under similar conditions. The kilned malt from Line G and the control barley cultivars lay within the specifications required for the semi-industrial brewing trials.

Brewing trials were performed on a 30-hl scale and evaluation of the freshly bottled beers revealed that beers brewed from malt of both Line G and the control cultivars had a trans-2-nonenal content below the taste-threshold and were deemed satisfactory by a taste-panel. Two forced-aging treatments, either storage at 37° C. for 7 days or storage for 6 to 12 weeks at 30° C., were used to evaluate the flavor-stability of the beer. The flavor-stability of beer brewed from Line G malt were found to be superior to that of control malt, both with respect to taste panel evaluation as well as the level of free trans-2-nonenal, and the improvement was found to be statistically significant.

EXAMPLES

The present invention is further defined in the Examples below. It should be understood that the Examples, while indicating preferred embodiments, are given by way of illustration only.

Example 1

Screening and Selection of Lipoxygenase Isoenzyme Mutants from Mutagenised Barley 1. Barley Mutagenesis Grains of barley, Hordeum vulgare cv Vintage and cv Caruso, were mutagenised with sodium azide according to a published procedure (Kleinhofs et al., 1978 Mutation Research 51: 29–35). The mutagenesis introduces point mutations in the genomic DNA that, for example, may result in amino acid changes in encoded proteins. The mutated M1 grains were propagated in the greenhouse through two generations, and the M3 grain collected for screening. The observed frequency of single gene trait mutants in the M2 generation, according to Kleinhofs et al., 1978, supra, are 1.0–2.7 mutants per 10,000 grain from the M2 generation. Since most gene mutations are recessive and only detectable in the homozygous state, the mutagenized population was screened at the M3 generation where the expected proportion of homozygous mutant grain would be higher. A mutation frequency of 0.9–2.3 per 10,000 grain was expected in the mutagenized material at M3.

2. A Non-destructive Assay of Lipoxygenase 1 (LOX-1) and Lipoxygenase-2 (LOX-2) Activity in M3 Mutagenized Grain A rapid screening procedure for detection of mutant barley grain with reduced LOX-1 activity was developed with the following criteria: The screening procedure should not prevent propagation of the grain/seedling; the selected grain/seedling tissue should express quantifiable levels of lipoxygenase activity; the assay should distinguish LOX-1 activity from that of LOX-2; and the assay procedure should encompass multiple samples.

The levels of total lipoxygenase activity in different tissues of the germinating grain, namely the shoot, root, and scutellum tissue of embryo and the endosperm were assayed as follows: Extracts of barley seedling tissue were prepared by homogenising the tissue in ice-cold 20 mM Tris-HCl, pH7.5, containing 2 mM $NaN_3$ and 0.5 mM phenylmethylsulfonyl fluoride (PMSF), followed by removal of insoluble material by centrifugation at 1000 g for 10 minutes. Lipoxygenase activity in 100 µl extract was assayed at 25° C., by addition of 2.9 ml of 20 mM linoleic acid substrate, prepared by dispersing 35 µl linoleic acid (free acid, L-1376, Sigma, USA) in 5 ml $H_2O$ containing 1% Tween 20. The reaction was followed spectrophotometrically, where the rate of increase in absorbance at 234 nm ($A_{234}$ nM), due to the formation of conjugated diene in the hydroperoxide product, is proportional to the enzyme activity present. One unit of lipoxygenase activity is defined as $\Delta A_{234}$=0.001 per minute in a 3-ml reaction, equivalent to the oxidation of 0.12 µmole linoleic acid.

The leaf tissue of grain germinated for 4 days in the dark had the highest detected levels of lipoxygenase activity (Holtman et al., 1996, Plant Physiology 111: 569–576). Leaf tips from 4-day seedlings were thus selected for the non-destructive lipoxygenase screening assay. The pH optimum of total barley lipoxygenase activity was tested between pH 4.5 and pH 9.0 and found to be pH 6.5. Hence a 25 mM HEPES buffer (pH 6.5) containing 0.2 M boric acid was selected for the screening assay.

Since both LOX-1 and LOX-2 enzymes were immuno-detected in shoots of 4-day seedlings (Holtman et al., 1996, supra), a LOX-1 and LOX-2 specific assay was used. The lipoxygenase inhibitor nordihydroguaiaretic acid (NDGA), identified by Eskin et al., 1977, Crit. Rev. Food, Science and Nutrition 9: 1–40, was found to be a selective inhibitor of barley lipoxygenases. NDGA at $1\times10^{-5}$ M strongly inhibited purified barley LOX-2, while LOX-1 retained 47% activity (FIG. 1). The selectivity of this inhibitor was tested in the leaf tip assay, by determining the ratio of 9-hydroperoxyoctadecadienoid (9-HPOD) to 13-hydroperoxyoctadecadienoid (13-HPOD), which result from linoleic acid oxidation by LOX-1 and LOX-2, respectively. In the lipoxygenase assay of cv Vintage leaf tips, the proportion of 13-HPOD formed fell from 24.5% to 9.5% on addition of $1\times10^{-5}$ M NDGA.

A selective assay for LOX-2 activity in leaf tip extracts was based on the use of LOX-1-specific monoclonal antibody (5D2) (Holtman et al., 1996, supra) to immunoprecipitate LOX-1 present in the extracts. The residual lipoxygenase activity detected in the extracts after LOX-1 precipitation provided a measure of LOX-2 activity. The efficiency of this immunoprecipitation (described below) was evaluated by quantifying the residual LOX-1 and LOX-2 in the extract supernatant by ELISA assay, using specific monoclonal antibodies against LOX-1 (denoted 5D2) and LOX-2 (denoted 5.8) (Holtman et al., 1996, supra). LOX-1 immunoprecipitation from extracts of cv Vintage leaf tips removed 85% of (LOX-1) protein and 15% of LOX-2 protein.

Immunoprecipitation was performed in a V-bottom 96-well plate by adding 5 µl 5D2-coated Dynabeads (Dynal) and 75 µl buffer [20 mM Tris-HCl pH 7.5, 1% v/v Bovine Calf Serum (HyClone)] to 20 µl of each leaf tip extract. The plate was incubated on a titerplate shaker (MTS4, IKA, Labor Technik) for 1 hour at 4° C. The immunoprecipitate was pelleted by centrifugation at 4° C. in a Sigma 302-K centrifuge for 10 minutes at 2000 rpm. The supernatant (70 µl) from each sample was assayed for lipoxygenase activity in a flat bottom 96 well plate, as described below, but with addition of 100 µl assay buffer (25 mM HEPES, 0.2 M boric acid, pH 6.5).

The LOX-1 and LOX-2 assays were adapted for a high-throughput screening method. Leaf tips (1 cm) from eight 4 day-germinated grains were individually homogenised in 150 µl ice-cold buffer (20 mM Tris-HCl, pH 7.5) for 2×30 seconds in a multi-well homogeniser (Berg et al., 1992, Electrophoresis 13: 76–81). After centrifugation for 15 minutes at 3000 rpm, 40 µl of the supernatant of each extract was transferred to a flat bottom 96 well plate. To each well, 170 µl buffer (25 mM HEPES, 0.2 M boric acid pH 6.5, $1\cdot10^{-5}$ M NDGA) and 10 µl substrate (20 mM linoleic acid) were added and then incubated for 20 minutes at 25° C. The reaction was terminated by the addition of 20 µl saturated potassium iodide solution (KI) and incubated for a further 8 minutes at 25° C. The redox reaction between hydroperoxydienes and KI yields $I_2$, which was monitored by its extinction maximum at 350 nm in a microplate reader (Multiskan MCC/340).

3. Identification of Potential Lipoxygenase 1 Mutants in the M3 and M4 Grain of Mutagenised Barley Grain of the M3 generation of cv Vintage and cv Caruso was stored at 45° C. for 6.5 days to break dormancy, ensuring a 95% germination frequency. M3 grain of cv Vintage (9318) and cv Caruso (9633) was germinated and screened for lines whose LOX-1 activity was 15% or less of wild-type grain. The putative mutant lines (50 cv Vintage and 42 cv Caruso lines) were propagated to the M4 generation, harvested, and the germinated grain re-screened. The mutant LOX-1 phenotype was confirmed in one cv Vintage line and six cv Caruso lines, after measuring the lipoxygenase activity in extracts of 5 leaf-tips from each line. When the LOX-1 and LOX-2 activities in germinating embryos of these 7 putative mutants were examined, only the cv Vintage mutant (denoted Line G) showed a major reduction in LOX-1. In mature quiescent grain, lipoxygenase activity present in the embryo is almost exclusively LOX-1 activity, due to the differential expression pattern of the two isoenzymes (Schmitt and van Mechelen, 1997, *Plant Sci.* 128: 141–150). The total lipoxygenase activity in extracts of embryos from Line G mature dry grain (M5 generation) was 0.06±0.04 U/mg protein in comparison to 0.74±0.44 U/mg protein in cv Vintage embryo extracts, as determined by the spectrophotometric lipoxygenase assay described in section 2 of Example 1. The residual lipoxygenase activity in mature embryos of Line G in both the M4 and M5 generations was found to be approximately 9% of the parental line.

Example 2

Line G Is a cv Vintage Mutant with a Low-Lipoxygenase Phenotype

The agronomic properties and mutant phenotype of Line G were analysed in material of the M5 generation. Initial analyses were conducted to confirm that the analysed M5 material was homozygous for the mutant phenotype. The low LOX-1 phenotype in Line G, detected in the M3 generation, could result from a dominant or a recessive mutation. If the Line G selected at the M3 generation was heterozygous for a dominant mutation, then subsequent generations would show segregation for the phenotype. The lipoxygenase activity in 26 individual Line G embryos from quiescent grain of the M5 generation was measured and compared to cv Vintage wild type embryos. The lipoxygenase activity in all Line G embryos was very low, with an average of 0.06±0.04 U lipoxygenase per mg protein, compared to 0.74±0.44 U lipoxygenase per mg protein in wild type cv Vintage embryos. These data confirmed that Line G in the M5 generation was homozygous for the low lipoxygenase trait.

1. Line G Has a Wild Type Plant Growth Physiology and Grain Development.

Figure 2:
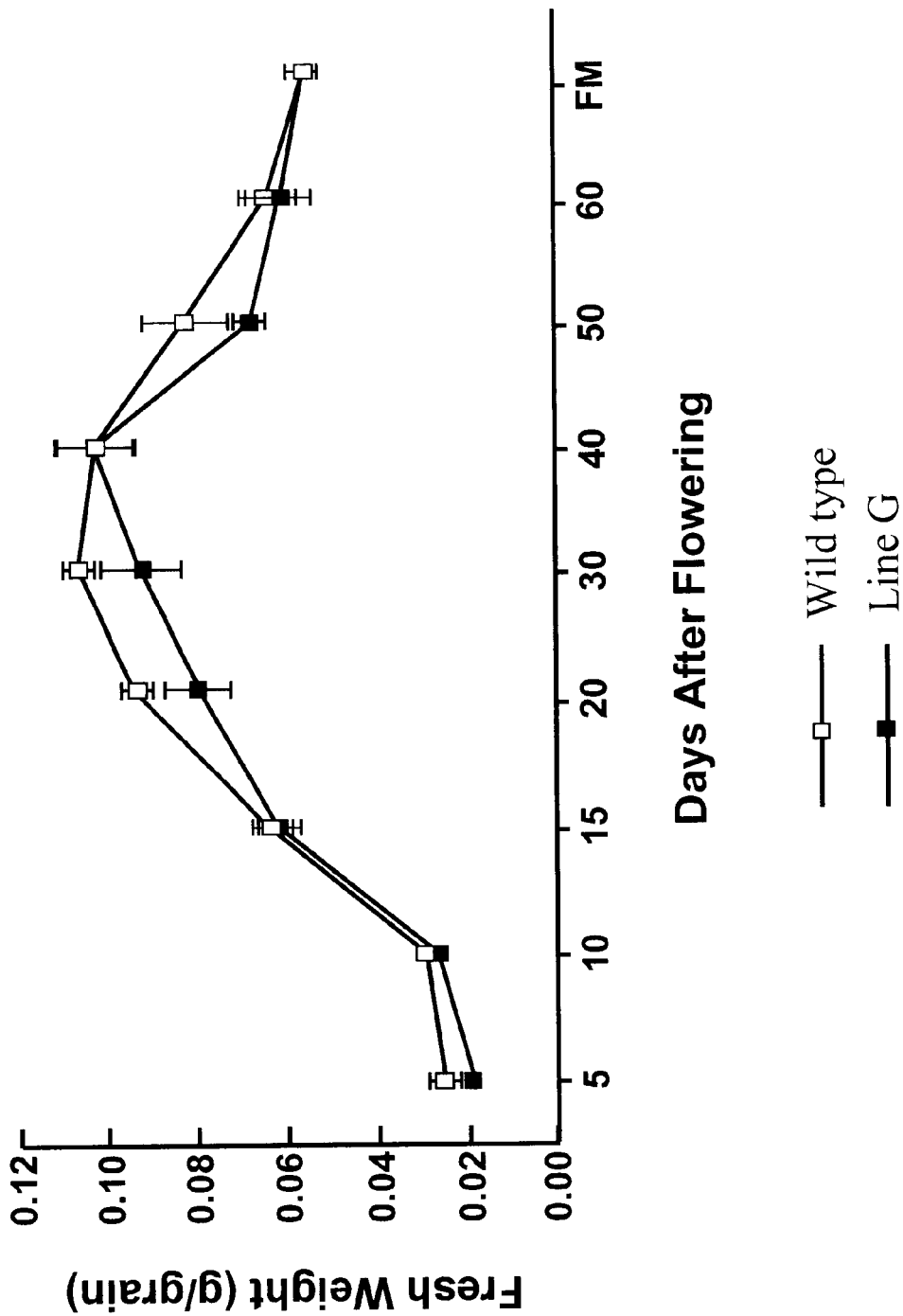
FIG. 2 is a graph showing the fresh weight of developing grain of Line G and cv Vintage from 5 days after flowering to full-maturity (FM). Each determination is the mean single grain weight from 6 spikes.
Figure 3:
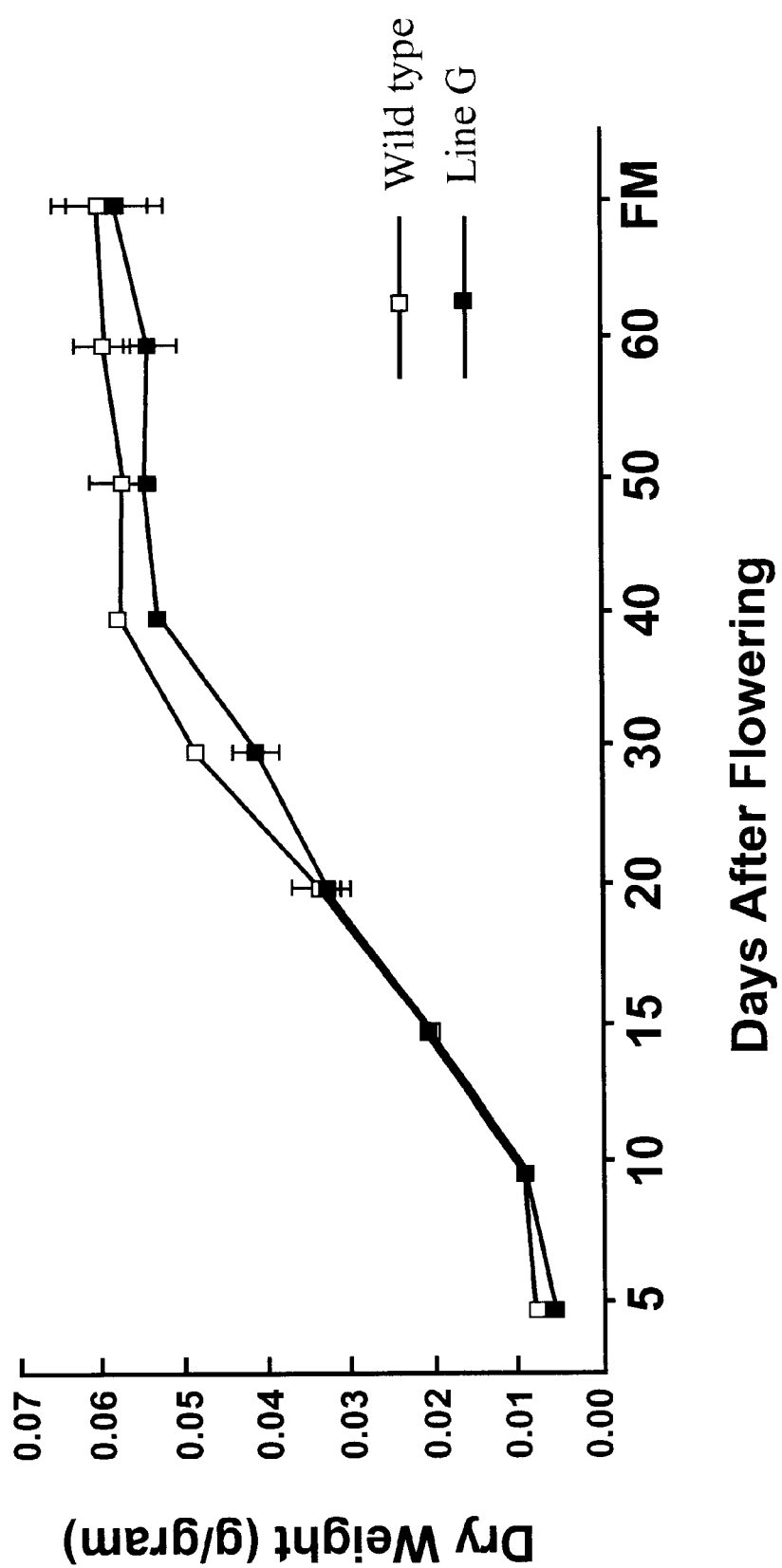
FIG. 3 is a graph showing the dry weight of developing grain of Line G and cv Vintage from 5 days after flowering to full-maturity (FM). Each determination is the mean single grain weight from 3 samples of 5 grain.

Line G and cv Vintage grain were germinated and grown in a climate chamber under 16 hours light at 15° C. and 8 hours dark at 12° C. at a relative humidity of 80%. The growth characteristics of Line G and cv Vintage plants were similar with regard to plant height, number of tillers per plant, the onset of flowering and number of grains per spike. The fresh weight (FIG. 2) and dry weight (FIG. 3) of grain of Line G and wild type cv Vintage during development from 5 days after flowering (DAF) until full maturity, approximately 90 DAF, were very similar.

2. Line G Grain Have a Low-lipoxygenase 1 Phenotype throughout Development

Figure 4:
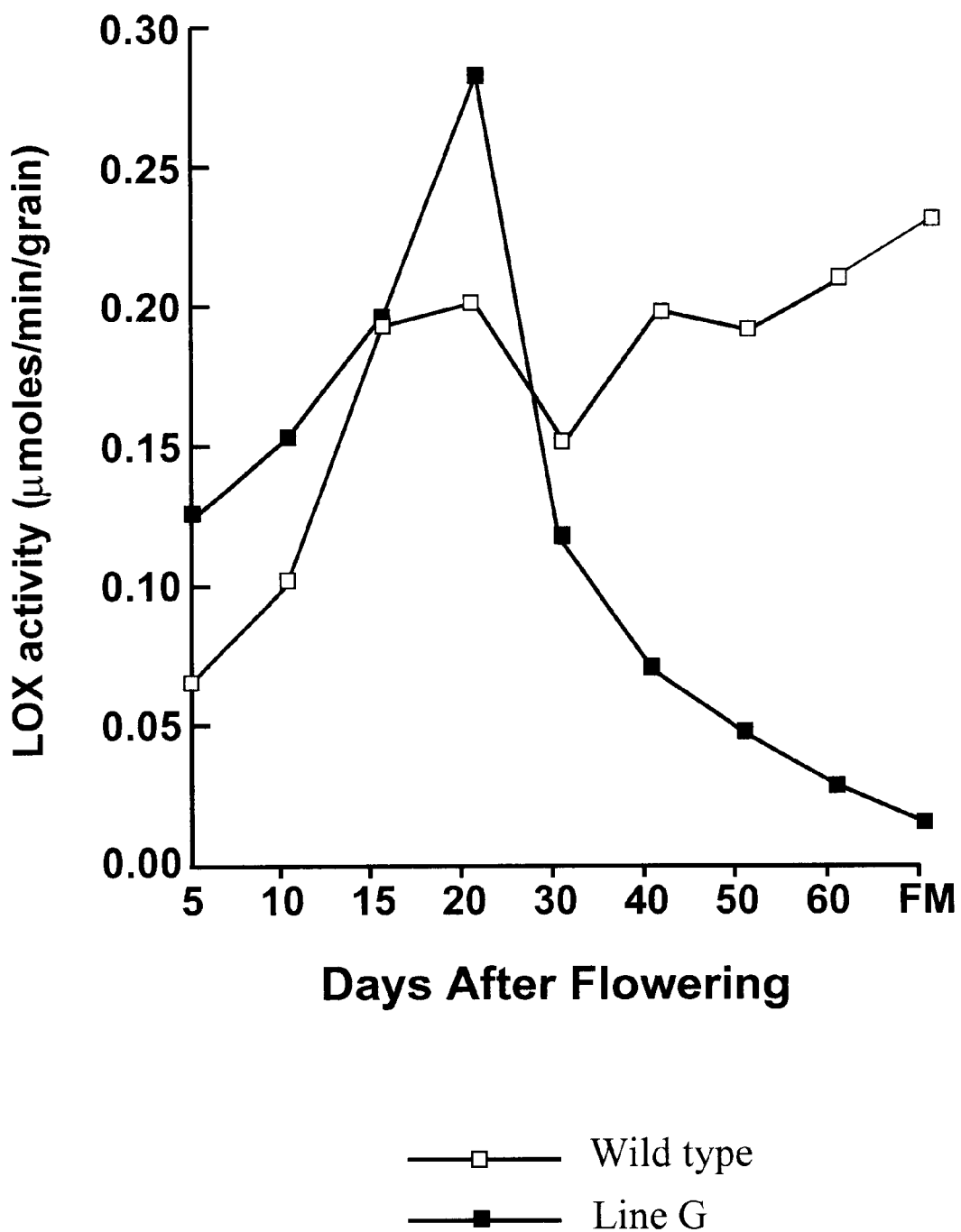
FIG. 4 is a graph showing total lipoxygenase activity in developing grain of Line G and cv Vintage from 5 days after flowering to full-maturity (FM).

Lipoxygenase activity was measured in extracts of developing barley grain of Line G (M5 generation) and wild type cv Vintage. Grain was homogenised in ice-cold 20 mM Tris-HCl buffer pH 7.5 containing 0% (v/v) Nonidet P-40, a non-ionic detergent that enhances lipoxygenase extraction, and centrifuged at 15,000 g for 20 minutes to remove insoluble material. Lipoxygenase activity in the extracts was measured polarographically in 200 µl oxygen-saturated buffer (0.2 M boric acid, 25 mM HEPES, pH 6.5) containing 1.2 mM linoleic acid at 25° C., using a Clark-type electrode to measure oxygen consumption. Lipoxygenase activity increased during the first 20 days of grain development in both Line G and wild-type grain, but only in Line G did the activity level fall during grain maturation (FIG. 4).

The relative amounts of 9-HPOD and 13-HPOD formed during linoleic acid oxidation provides a measure of the levels of LOX-1 and LOX-2 activity in the grain extracts. In this case Nonidet P-40 was omitted from the grain extraction buffer to avoid the co-extraction of hydroperoxide-consuming enzymes. The extracts (100 µl), mixed with 10 ml 50 mM phosphate buffer pH 6.5 containing 200 µM linoleic acid, were incubated for 20 minutes. The reaction was terminated by adjusting the pH to 3.5, and an internal standard was added. The hydroperoxides formed in the assay were bound on an octadecyl solid phase column (Bakerbond, Baker) and eluted with methanol. The 9-HPOD and 13-HPOD were then separated by reverse phase HPLC on a C-18 column with an isocratic elution solvent (tetrahydrofuran:Methanol:$H_2O$:acetic acid; 25:30:44.9:0.1 (v/v) adjusted to pH 5.5 with concentrated ammonia) at a flow rate of 0.5 ml/minute as described by Aarle et al., 1991, *FEBS Letters* 280: 159–162. Hydroperoxides were detected at 234 nm and the HPOD peaks were corrected against the internal standard, prostaglandin B2.

Figure 5:
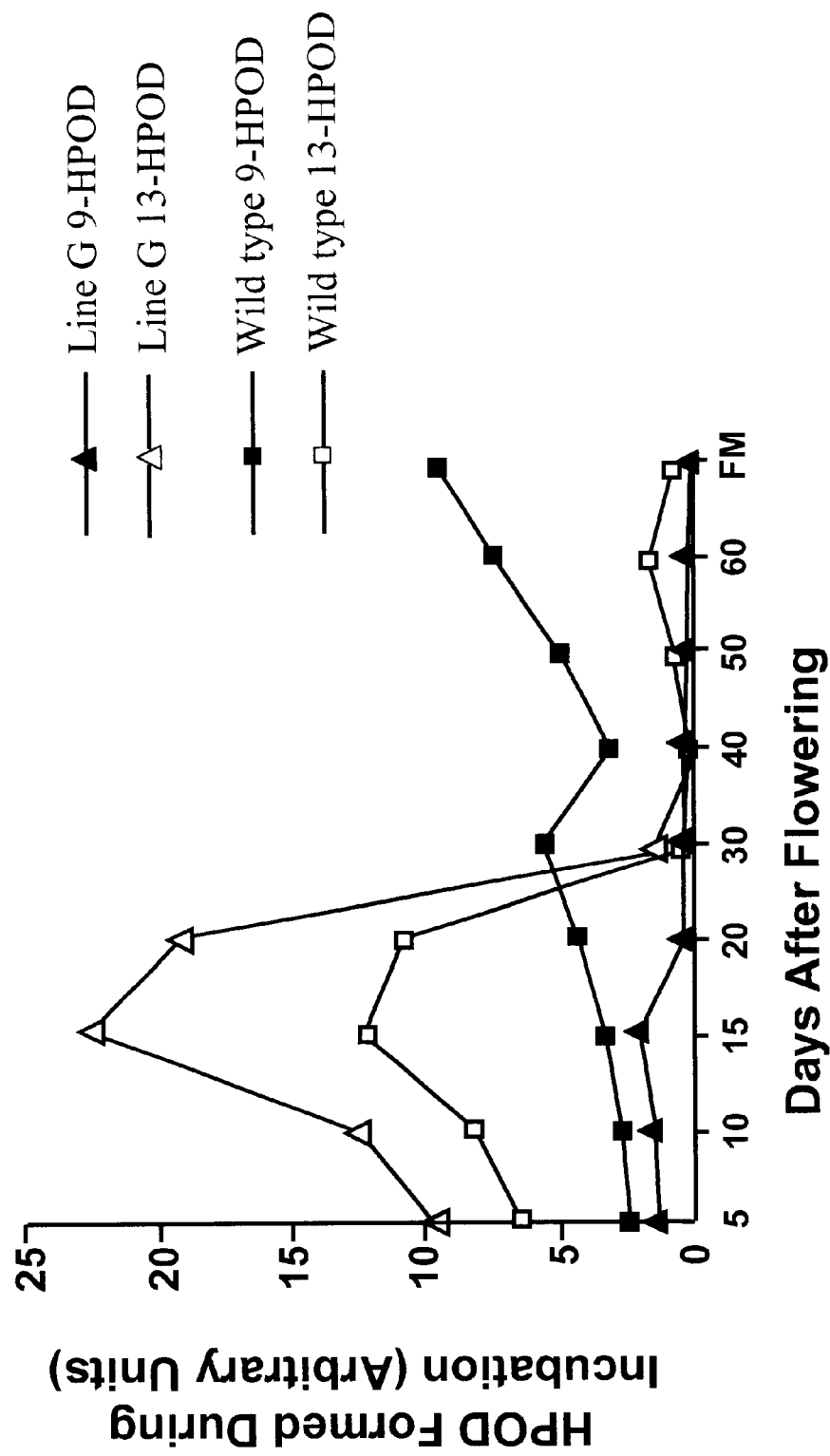
FIG. 5 is a graph showing 9- and 13-HPOD products of linoleic acid oxidation by lipoxygenase activity in developing grain of Line G.

FIG. 5 shows that 13-HPOD was the major product of lipoxygenase activity present in grain during the first 20 DAF, while 9-HPOD was formed by lipoxygenases active during grain maturation. While both Line G and wild-type grain extracts shared a similar profile of 13-HPOD synthesising activity, Line G did not show the wild-type rise in 9-HPOD synthesising activity. These data are consistent with a loss of LOX-1 activity in maturing Line G barley grain.

3. Line G Grain Have a Low-lipoxygenase 1 Phenotype on Germination

Figure 6:
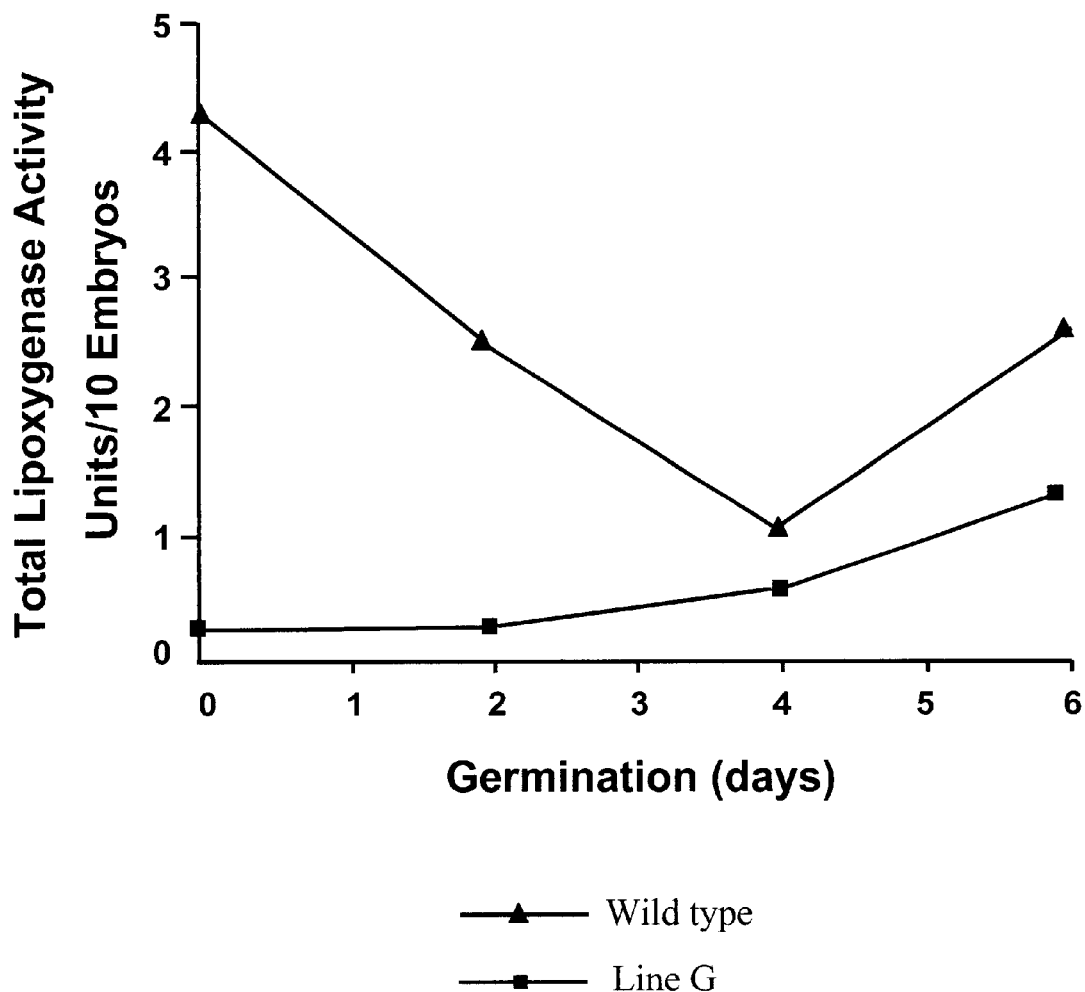
FIG. 6 is a graph showing total lipoxygenase activity in embryos of germinating grain of Line G and cv Vintage expressed as $\mu$mol/min/10 embryos (U/10 embryos).

Total lipoxygenase activity in extracts of embryos of grain germinated at 15° C. was assayed as described in Example 1. The lipoxygenase activity present in quiescent wild-type grain declined during the first 4 days of germination and then increased (FIG. 6). In Line G, lipoxygenase activity in quiescent grain was very low but increased after 4 days.

Figure 7:
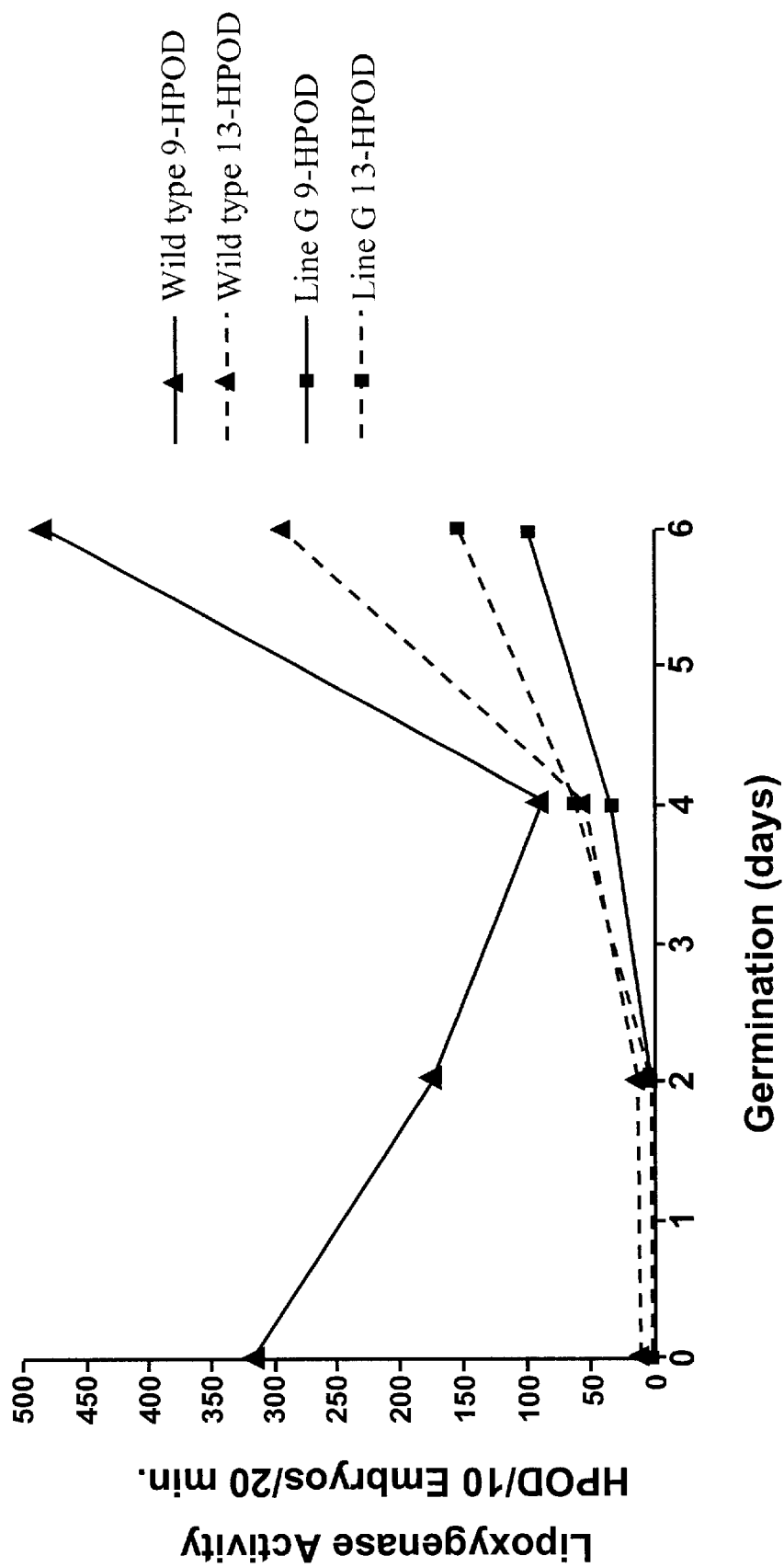
FIG. 7 is a graph showing 9-HPOD and 13-HPOD products of linoleic acid oxidation by lipoxygenase activity in embryos of germinating grain of Line G and cv Vintage, showing levels of 9-HPOD and 13-HPOD.

Analysis of the HPODs formed by the lipoxygenase activity in germinating embryos showed that 9-HPOD was the major product of lipoxygenases present in quiescent wild-type grain (FIG. 7). The level of 9-HPOD formation fell with the decline in lipoxygenase activity in the extracts. The rise in lipoxygenase activity after 4 days was accompanied by the formation of both 9-HPOD and 13-HPOD. The low lipoxygenase activity in Line G quiescent grain was associated with an absence of HPOD formation, while the rise in activity after 4 days mainly produced 13-HPOD. These data provide evidence that LOX-1 activity leading to the formation of 9-HPOD is greatly reduced in the embryos of both developing, quiescent and germinating barley grain of Line G, while LOX-2 activity leading to formation of 13-HPOD is unchanged in Line G.

Example 3

Figure 8:
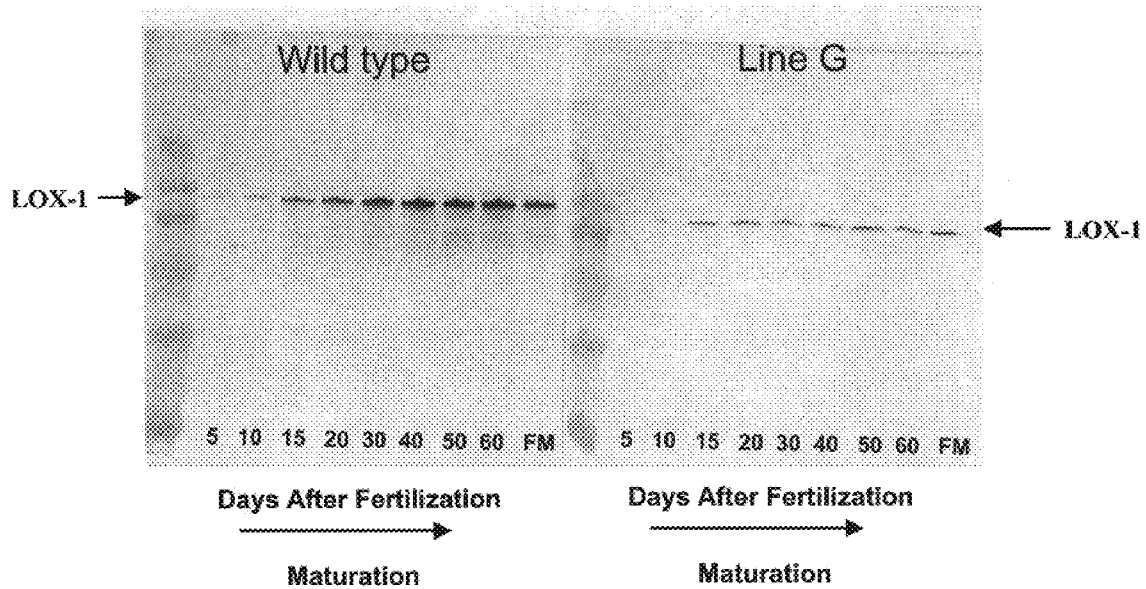
FIG. 8 is a Western blot showing immunodetection of lipoxygenase 1 in embryos of developing grain of Line G and cv Vintage [wt] from 5 days after flowering to full-maturity (FM).
Figure 9:
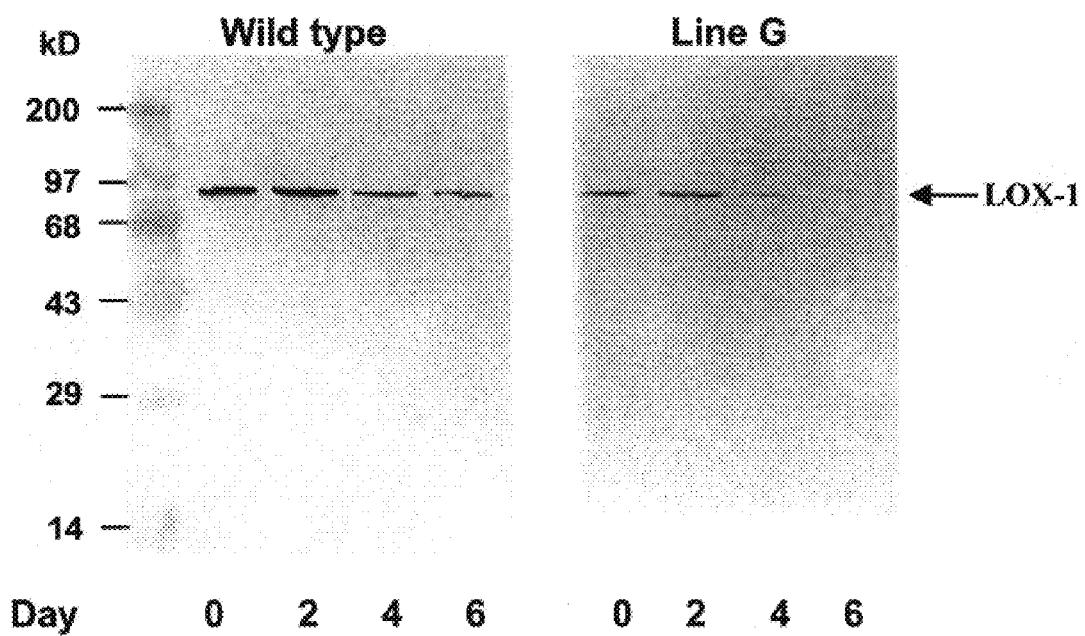
FIG. 9 is a Western blot showing immunodetection of lipoxygenase 1 in embryos of grain of Line G and cv Vintage [wild-type] germinated for 0–6 days.

Line G Has a Mutant Lipoxygenase 1 Gene (lox-1) Causing a Low Lipoxygenase Phenotype The molecular basis for the low-LOX-1 phenotype of Line G was investigated in order to provide a complete description of the mutant. The following analyses were performed to provide a complete characterization of the phenotype:

1. Lipoxygenase-1 is Synthesised in the Developing and Germinating Grain of Line G Western blot analysis of extracts of embryos from developing and germinating barley grain were performed in parallel with the measurement of lipoxygenase activity, as described in Example 2. The crude extracts were separated by sodium dodecyl sulphate-polyacrylamide gel electrophoresis (SDS-PAGE) according to Laemmli, 1970, *Nature* 227: 680–685. The separated proteins were transferred to nitrocellulose by semi-dry blotting, according to Towbin et al., (1979) *Proc. Natl. Acad. Sci.* USA 76: 4350–4354. The blot was probed with the LOX-1 specific monoclonal antibody, 5D2, as described Holtman et al., 1996, *Plant Physiology* 111: 569–576, at 500× dilution, followed by incubation with goat anti-mouse antibody coupled to alkaline phosphatase, and detected with the alkaline phosphatase substrates nitro blue tetrazolium and 5-bromo-4-chloro-3-indolyl-phosphate as described by Holtman et al., 1996, *Plant Physiol.* 111: 569–576. The Western analyses revealed that LOX-1 protein was detected in developing grain from 10 DAF in cv Vintage embryos and the level increased during grain maturation (FIG. 8). The protein was also present in the embryo of cv Vintage quiescent grain but declined slowly during germination (FIG. 9). Although LOX-1 is recognised in extracts of Line G embryos and migrates in SDS-PAGE as a protein of similar size to cv Vintage LOX-1, the immunodetectable levels of the protein in Line G were slightly lower than in cv Vintage.

2. The lox-1 Gene is Expressed in the Developing and Germinating Grain of Line G Total RNA was isolated from embryos of developing and germinating barley grain, according to the procedure of Hensgens and van Os-Ruygrok, 1989, *Rice Genet. Newslett.* 6: 163–168, in parallel with the measurement of lipoxygenase activity, described in Example 2. The RNA samples (7.5 μg) were separated on denaturing agarose gels and Northern blotted as described by Sambrook et al., 1989 in Molecular Cloning, a Laboratory Manual, Cold Spring Harbour Laboratory Press, N.Y. The blots were hybridised with a $^{32}$P-labelled probe generated from the barley 3' untranslated region, nucleotides 2659–2801 [SEQ ID NO:1], of the lox 1 cDNA (EMBL Accession no. L35931) as described by Holtman et al., 1996 *Plant Physiol.* 111: 569–576, using the Amersham Random Prime Kit.

Figure 10:
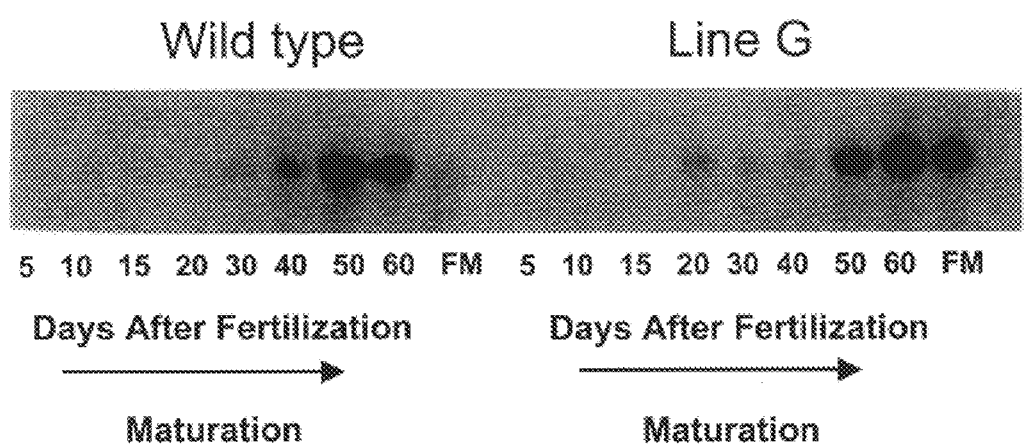
FIG. 10 is a Northern blot probed with the 3' non-transcribed region of the lox-1 cDNA and showing lipoxygenase 1 transcripts detected in developing grain of Line G and cv Vintage [wild-type] from 5 days after flowering to full-maturity (FM).
Figure 11:
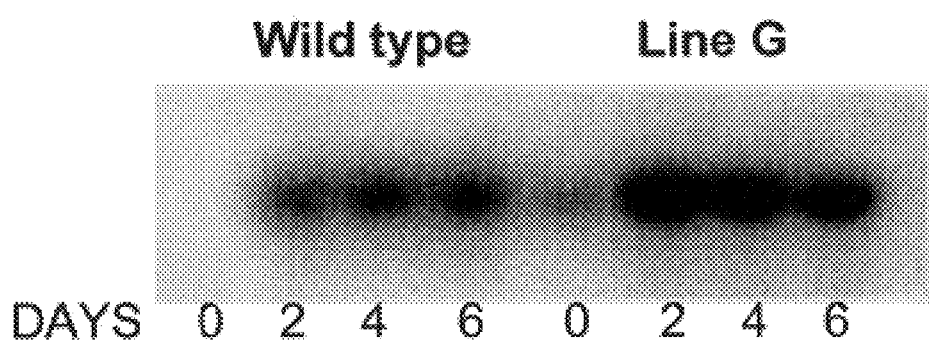
FIG. 11 is a Northern blot probed with the 3' non-transcribed region of the lox-1 cDNA and showing lipoxygenase 1 transcripts detected in embryos of grain of Line G and cv Vintage [wt] germinated for 0–6 days.

Lox-1 transcripts encoding LOX-1 were detected in embryos of developing and mature cv Vintage and Line G grain from 30 DAF (FIG. 10). The level of lox-1 trancripts increased during germination in both cv Vintage and Line G embryos, indicating de novo expression of the lox-1 gene (FIG. 11). Since the detectable levels of lox-1 transcripts were similar in Line G and cv Vintage embryos, neither reduced lox-1 transcription or transcript stability can account for the low-lipoxygenase phenotype of Line G.

3. The lox-1 Gene of Line G Encodes a Mutant Form of Lipoxygenase-1

The nucleotide sequence of the lox-1 gene of Line G and cv Vintage were analysed and compared in order to determine the molecular basis for the low-LOX-1 phenotype of Line G, which is characterised by normal transcription of the lox-1 gene, but reduced accumulation and activity in the expressed lipoxygenase enzyme in grain.

Genomic DNA from Line G and wild-type cv Vintage was isolated from seedling leaf tissue according to a method described by Pich and Schubert 1993, *Nucleic Acids Res.* 21:3328. The lox-1 gene in the genomic DNA preparations was amplified by polymerase chain reaction (PCR) using primers based on the sequence of the barley lox-1 gene (van Mechelen et al. 1995, *BBA* 1254: 221–225; Rouster et al., 1997, *Plant J.* 11: 513–523). The position and sequence of the oligonucleotide primers used to amplify the lox-1 promoter and coding regions, indicated in FIG. 12 were as follows:

Forward primer 5'-GAA AAG CTT GGA GGT AGA CGC TGC-3' [SEQ ID NO:2] and reverse primer 5'-TAT AGG ATC CTT GTT CTT GGC CTC CTC TCC TCG-3' [SEQ ID NO:3] were used to PCR amplify the lox-1 promoter domain (−361 to +68) of Line G and cv Vintage lox-1.

Forward primer 5'-AGT GAA AAA CAG TGT GCT GGT G-3' [SEQ ID NO:4] and reverse primer 5'-GGC TTA AAG AGC AAC TGC TGA-3' [SEQ ID NO:5] were used to PCR amplify the Line G lox-1 coding region.

Forward primer 5'-CAA GAT GCA TAT GCT GCT GGG AG-3' [SEQ ID NO:6] and reverse primer 5'-CGA TGG TTT AAA TTA GAT GGA GAT GCT GT-3' [SEQ ID NO:7] PCR amplified the cv Vintage lox-1 coding region.

The PCR reactions consisted of 250 ng genomic DNA in a 50 μl volume containing 50 pmol primer and 2 U Pfu DNA polymerase (Promega) according to the enzyme suppliers instructions. The PCR amplifications were carried out in a Stratagene Robocycler: 1 minute at 94° C., 1 cycle; 1 minute at 94° C., 2 minutes at 62° C., and 5 minutes at 72° C., 30 cycles; 10 minutes at 72° C., 1 cycle. The PCR products were separated on 1.2% agarose gels. DNA fragments, corresponding in length to the amplified region, were purified using Qiax II Gel extraction kit (Qiagen) and cloned into the plasmid pcDNA2.1 (Invitrogen). The nucleotide sequence of both strands of the cloned lox-1 promoter and coding regions was determined using the dideoxynucleotide chain termination reaction with specific oligonucleotide primers and analysed on an ABI PRISMS® 310 Genetic Analyzer (PE Biosystems). Sequence comparisons were performed using the DNA STAR sequence analysis software package (DNA STAR Inc., USA).

The promoter region and intron-exon structure of the barley lox-1 coding region are shown in FIG. 13, and were deduced from a comparison of the nucleotide sequence of the wild-type lox-1 genomic and cDNA sequences (FIG. 12). The sequenced region of the lox-1 promoter region from −363 to +68, (numbered relative to the determined transcription start site; van Mechelen et al., 1995, *BBA* 1254: 221–225), is sufficient to direct embryo-specific and temporally-regulated gene expression characteristic of the native gene (Rouster et al, 1998, *Plant J* 15: 435–440). The promoter and transcribed region of the wild-type lox-1 gene [SEQ ID NO:8] is 4663 nt in length and contains 6 introns of between 82 nt and 634 nt in length, which are absent from the respective cDNA [SEQ ID NO:10] and must therefore be removed during RNA transcript splicing.

Comparison of the nucleotide sequence of lox-1 of Line G with that of wild-type (FIG. 12) showed that the Line G lox-1 allele has two point mutations. One is a silent C→T substitution at position 221 in exon 1, and the second is a G→A substitution at position 2347 in exon 3 (FIG. 13). The wild-type barley lox-1 gene encodes a protein of 862 amino acid residues [SEQ ID NO:9], while the mutation at position 2347 in Line G lox-1 allele causes an amino acid substitution of glycine to aspartic acid at residue 368 in the encoded protein.

Alignment of related plant lipoxygenases indicated that the glycine-368 in barley LOX-1, is strongly conserved.

Furthermore this residue, which corresponds to glycine-353 in soybean LOX-1, is one of 51 neutral or hydrophobic residues which line the substrate cavity of the enzyme, as seen from its crystal structure (Minor et al., 1996, *Biochemistry* 35: 10687–10701) and is shown in (FIG. 22). The insertion of a charged amino acid residue at this position is thus likely to disturb the structural and functional properties of the enzyme.

4. The Mutated LOX-1 Protein Encoded by the Line G lox-1 Allele has Low Enzymic Activity and is Responsible for the Low Lipoxygenase Phenotype of Line G.

The sodium azide mutagenesis of cv Vintage grain, which induced the mutated lox-1 allele in Line G, may have induced additional mutations in the Line G genome. Two experimental approaches have been taken to demonstrate that the mutant lox-1 allele in Line G is responsible for its low lipoxygenase phenotype, rather than other mutations in the genome. The enzymatic activity of the LOX-1 encoded by the mutant and wild-type lox-1 allele have been determined in order to prove that the glycine→aspartic acid substitution in the mutant enzyme causes reduced stability and activity. The two lox-1 genes were transiently expressed in aleurone protoplasts isolated from imbibed mature grain, since the level of endogenous lipoxygenase expression in these cells was expected to be below detection limits. None of the identified barley lipoxygenase genes, which are expressed in germinating barley, are detected in the aleurone tissue (van Mechelen et al., 1999 supra). In order to direct transient expression of the lox-1 gene in aleurone protoplasts, their coding regions were translationally fused to a constitutive promoter known to be active in these protoplasts.

Figure 14:
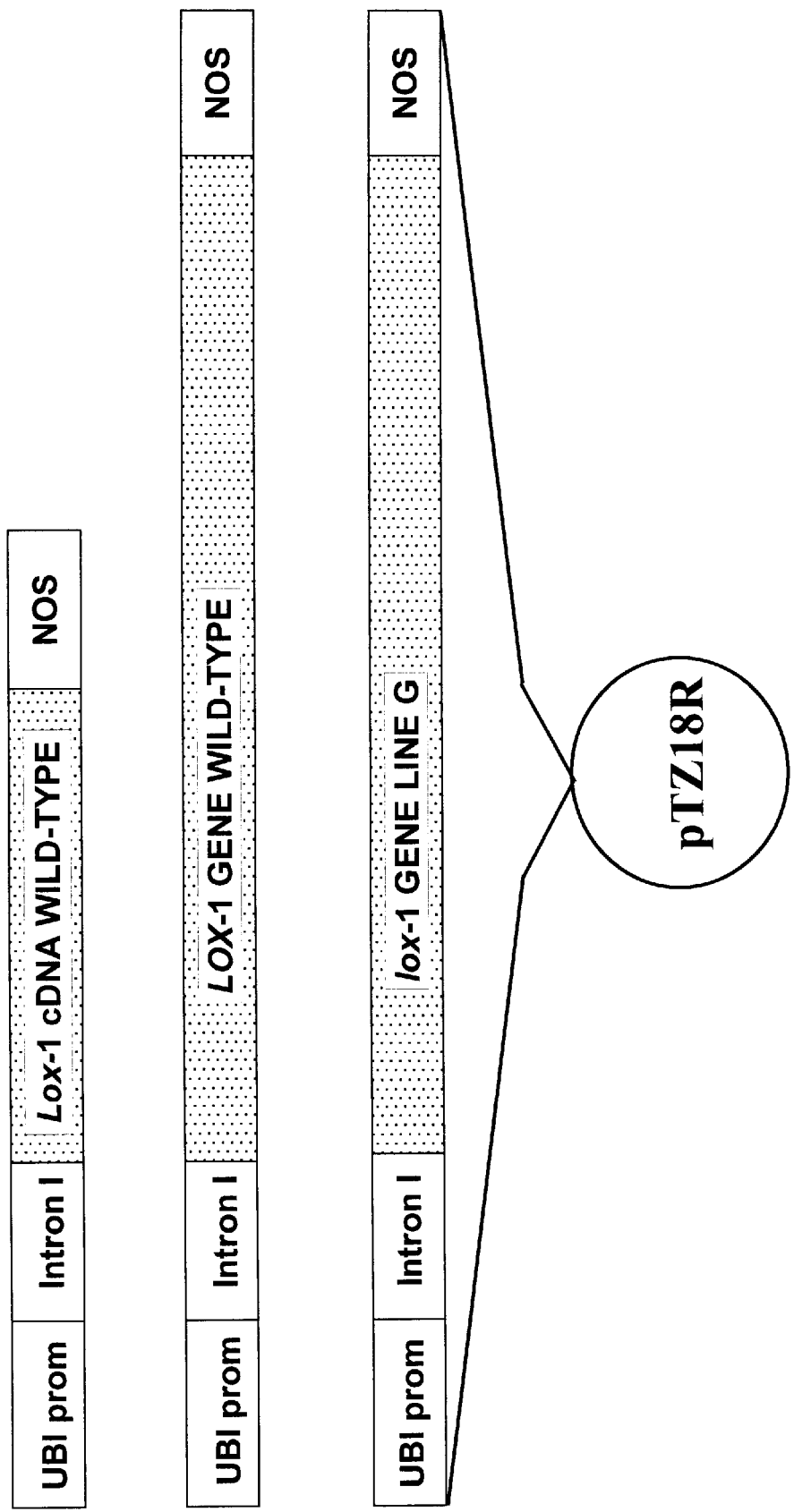
FIG. 14 is a schematic drawing of gene cassettes for transient expression of the wild-type lox-1 cDNA and lox-1 gene and the mutant lox-1 gene from Line G. The lipoxygenase coding sequences were cloned between the constitutive maize ubiquitin promoter with intron 1 (Ubi-1) and the nos terminator.

The coding regions of the mutant (sequence positions +1 to +4350) and the wild-type lox-1 gene (sequence positions +69 to +4230) and the wild-type lox-1 cDNA (sequence positions +69 to +2654) each cloned in plasmid pcDNA2.1 (see section 3), were excised by digestion of the KpnI and EcoRV sites in vector polylinker. The coding regions were cloned in the pUBARN plasmid (Jensen et al., 1998, *Hereditas* 129: 215–225) between the constitutively active maize ubiquitin Ubi promoter (as described in U.S. Pat. No. 5,510,474A) and the Nos terminator, in place of the bar gene which encodes phosphinotricin acetyl transferase (FIG. 14).

Protoplasts were isolated from aleurone tissue of imbibed *Hordeum vulgare* cv Himalaya according to the protocol of Skriver et al. 1991, *Proc. Natl. Acad. Sci.* USA 88: 7266–7270. Aliquots of $2 \cdot 10^5$ protoplasts were transfected at 0° C. with ~100 μg plasmid DNA (equimolar amounts of each plasmid) by polyethylene glycol (PEG) mediated DNA uptake (Lee et al., 1997, *Plant Mol. Biol.* 13: 21–29), and then incubated in aleurone protoplast culture media at 25° C. as described previously (Skriver et al., 1991 supra). After 48 hours incubation, the culture medium was carefully removed and the protoplasts were re-suspended and homogenised in 300 μl lipoxygenase assay buffer (0.2 mM boric acid, 25 mM HEPES, pH 6.5). The homogenates were centrifuged at 15,000 g for 5 minutes to pellet insoluble material, and the supernatants (10 μl) were subsequently assayed for total lipoxygenase activity using the rapid screening assay described in Example 1, section 1, but with omission of the NDGA inhibitor. The protein content of the protoplast extracts was measured by a Bradford dye-binding assay (Bradford 1976, *Anal. Biochem.,* 72: 248) supplied by Bio-Rad Laboratories, Hercules, Calif., USA, and lipoxygenase activity was expressed per mg protein in the extract.

Figure 15:
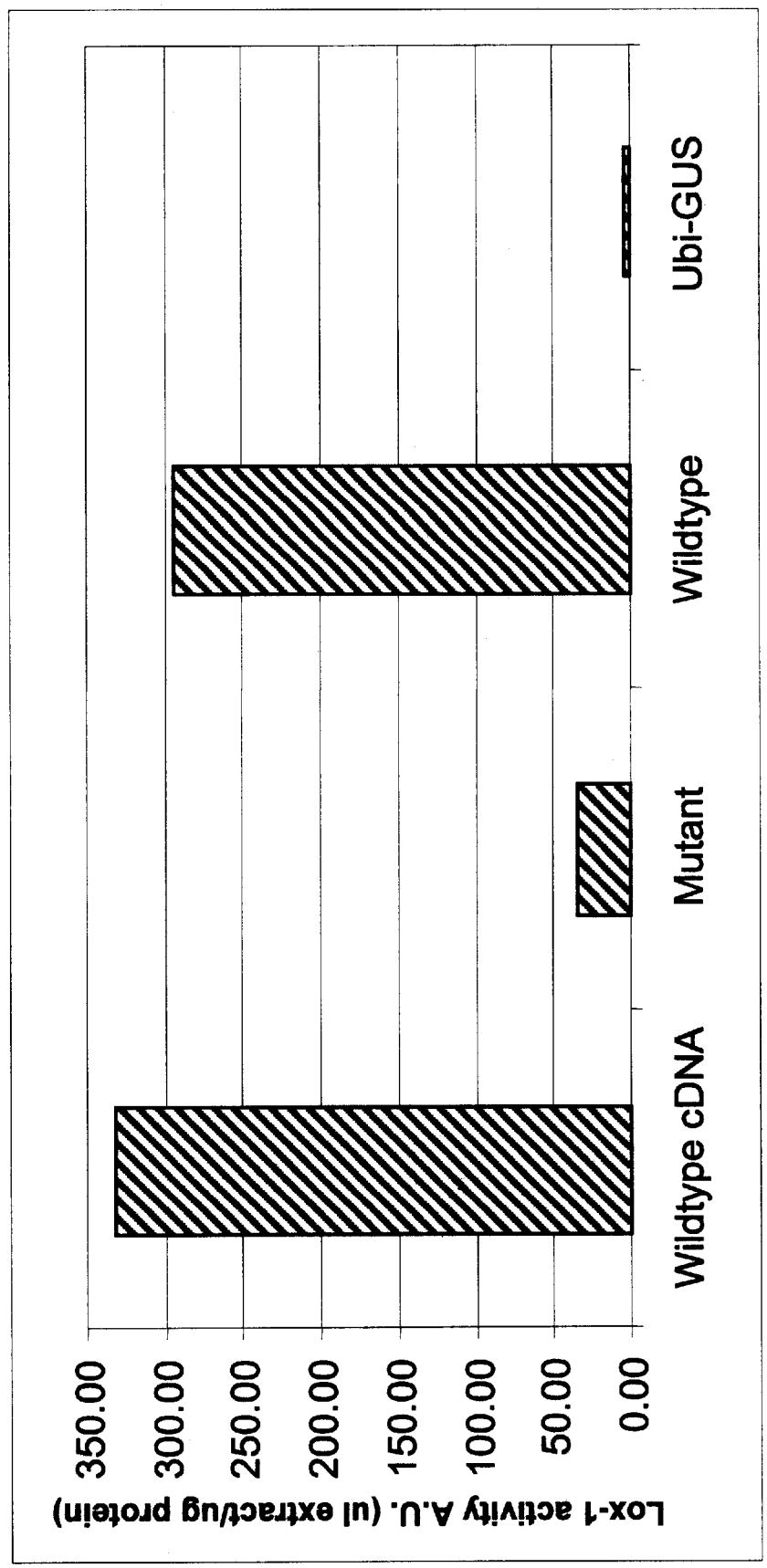
FIG. 15 is a bar graph showing Lipoxygenase 1 activity in barley aleurone protoplasts transfected with gene cassettes containing the wild-type lox-1 cDNA; the mutant lox-1 gene from Line G; WT lox-1 gene; and a control GUS reporter gene. Lipoxygenase activity in extracts of transfected protoplasts was assayed in microtiter plates by the oxidation of KI and quantitated spectrophotometrically. Lipoxygenase 1 activity was expressed as units per fg protein in the extract and is shown as the mean of 3 measurements from 2 replicate assays.

Protoplasts transfected with the control plasmid, pUBI-GUS, where the maize ubiquitin-1 promoter directs expression of the β-glucuronidase reporter gene, gave no detectable lipoxygenase activity. Transient expression of the wildtype lox-1 gene and cDNA in protoplasts both gave high levels of lipoxygenase activity in the protoplast extracts (FIG. 15). The higher expression of the wild-type lox-1 cDNA in comparison to the genomic sequence may be due to a higher transfection frequency for the smaller lox-1 cDNA expression plasmid (4929 bp versus the 6505 bp lox-1 gene construct). Transient expression of the mutant lox-1 gene gave low levels of lipoxygenase activity, ~10% of wild-type lipoxygenase activity. These data clearly demonstrate that the mutant lox-1 gene in Line G encodes a lipoxygenase with greatly reduced activity, which accounts for the low lipoxygenase phenotype.

Example 4

PCR-Cleavage Amplified Polymorphic Site (PCR-CAPS) Assay: A Method Used for Identification of the Mutant lox-1 Gene An analytical method allowing the identification of the Line G mutant lox-1 gene in any genetic background was developed based on the PCR-CAPS assay. The assay involves PCR amplification of genomic DNA fragments, followed by digestion of the amplified sequences with a specific restriction endonuclease to display a restriction fragment length polymorphism (RFLP).

Figure 16:
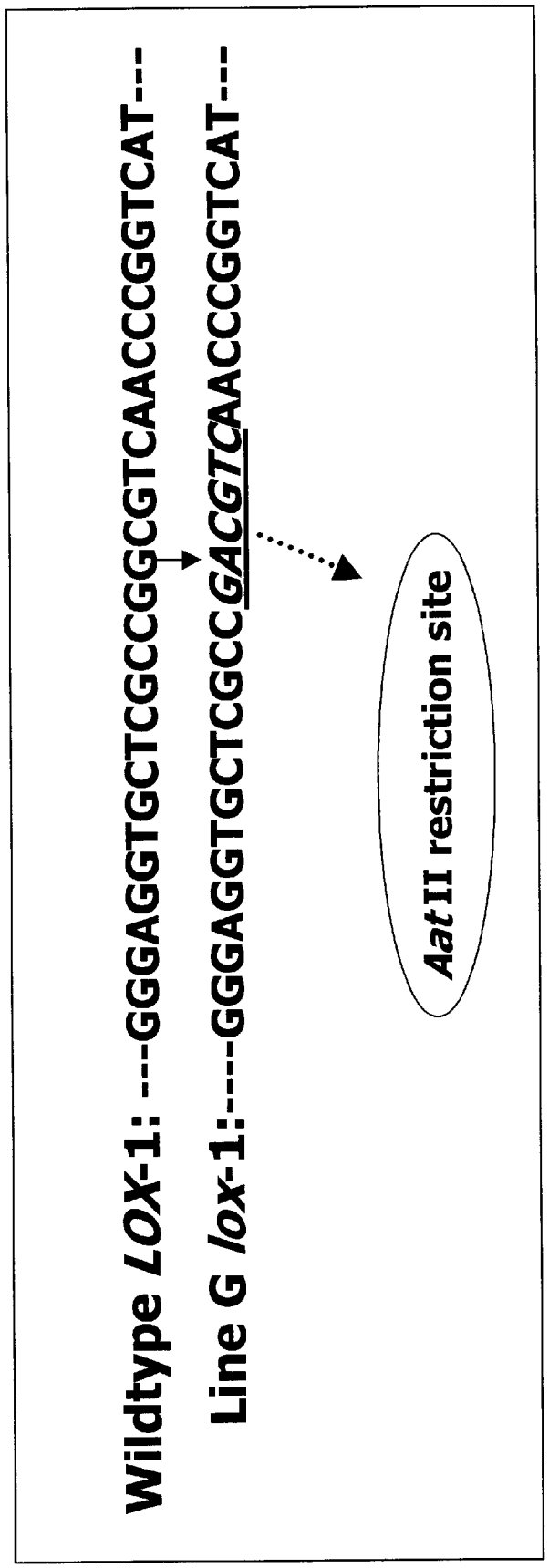
FIG. 16 is a sequence alignment demonstrating that a RFLP between the wild-type and mutant lox-1 gene is due to a point mutation at nucleotide 2347, creating an additional AatII restriction site.

The coding sequence of the mutant lox-1 gene harbours two point mutations (see Example 3), where the mutation at position 2347 (FIG. 12) introduces an additional Aat II restriction endonuclease cleavage site, not found in the wild-type lox-1 gene (FIG. 16). The following PCR-CAPS assay, based on the polymorphism created by the presence of this restriction site in the lox-1 gene, is shown to descriminate between a wild-type lox-1 gene and a mutated lox-1 gene.

Figure 17:
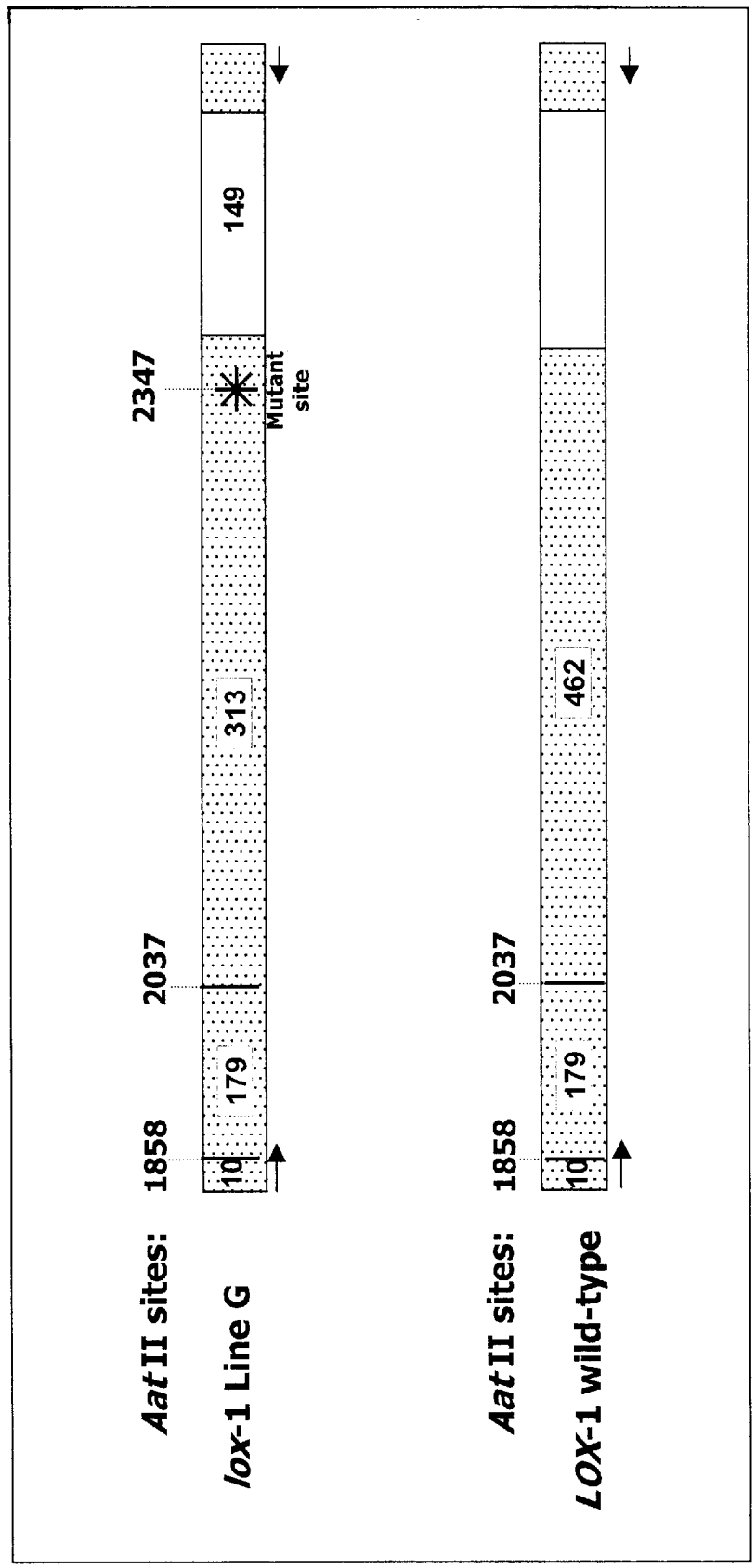
FIG. 17 is a schematic presentation of the lox-1 PCR fragments amplified and cleaved in the polymerase chain reaction—cleavage amplified polymorphic site (PCR-CAPS) assay. The positions of PCR primers are indicated by arrows and the AatII sites are shown above the gene (sequence position). The exon and intron regions within the PCR product are distinguished by stippled and white boxes respectively, and the sizes of the AatII digestion fragments are given.
Figure 18:
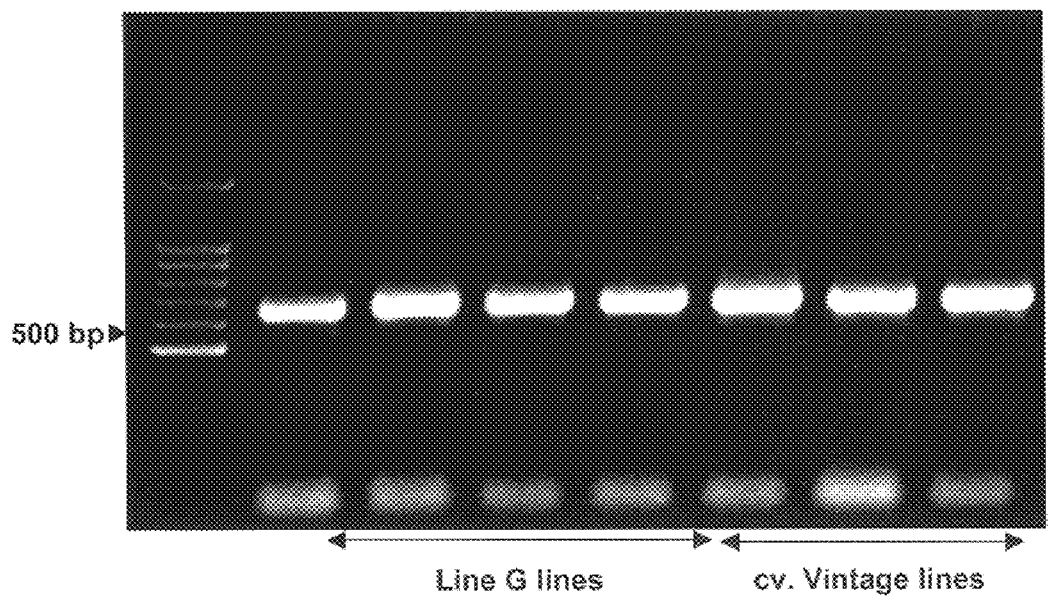
FIG. 18 is an electrophoretic agarose gel showing lox-1 PCR fragments (652 bp) amplified in the first step of the PCR-CAPS assay from Line G and cv Vintage genomic DNA.

Genomic DNA was isolated from young leaves of M6 seedlings of *Hordeum vulgare*, L. cv Vintage and Line G according to the procedure of Pich and Schubert (1993, supra). The DNA sequence encompassing position 2347 (Line G lox-1 gene mutation site) was amplified by PCR, using primers specific for the lox-1 gene [SEQ ID NO:8]. The DNA fragments amplified by the selected forward primer 5'-CGCTACGACGTCTACAACGA-3' [SEQ ID NO:13] and reverse primer 5'-CAGACTACTTTTT-GGCGGGA-3' [SEQ ID NO:14] are shown in FIG. 17. PCR reactions were carried out with 250 ng genomic DNA in a 50-μl volume containing 50 pmol of each primer and 1 unit Taq DNA polymerase (Promega) according to the suppliers instructions. PCR amplifications were carried out on a Stratagene Robocycler as follows: 1 minute at 94° C., 1 cycle; 1 minute at 94° C., 1.5 minutes at 60° C., and 2 minutes at 72° C., 30 cycles; 10 minutes at 72° C., 1 cycle. The amplified fragments of the mutant and wild-type lox-1 gene were ~650 bp (FIG. 18), corresponding to the expected size (FIG. 17). The PCR products, purified on a spin column (Qiagen), were digested with 25 unit Aat II restriction endonuclease for 24 hours at 37° C. and analyzed on a 1.2% agarose gel.

Figure 19:
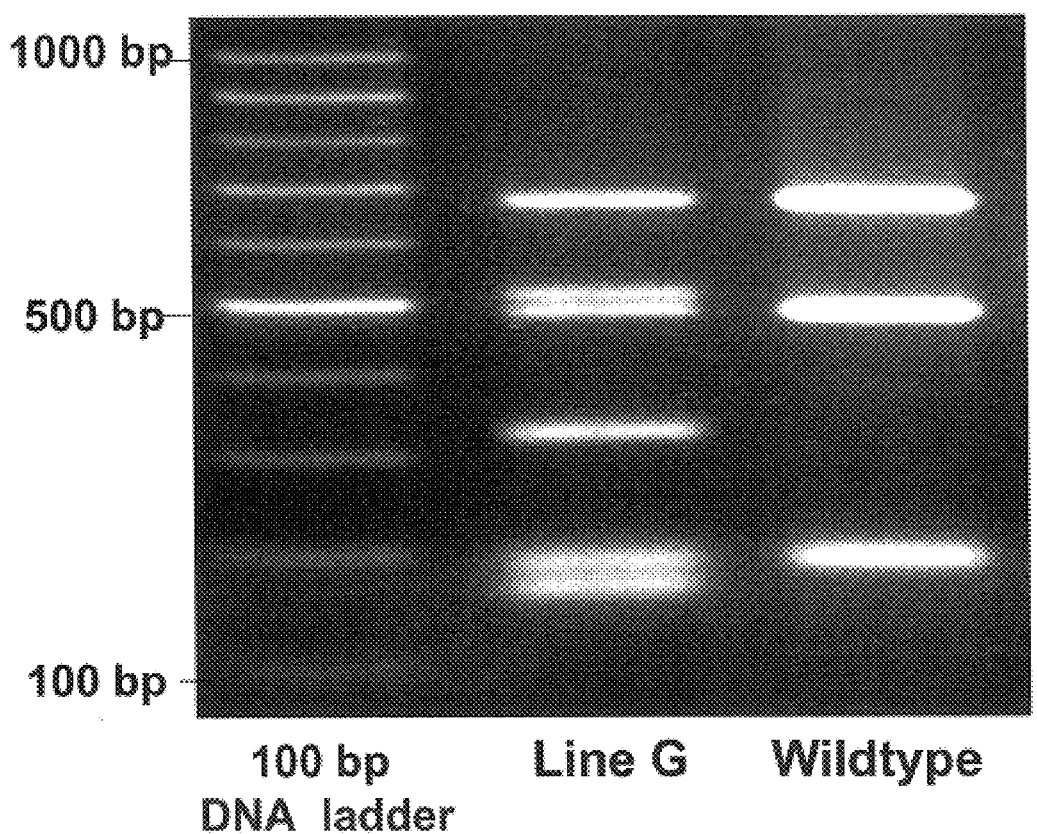
FIG. 19 is an electrophoretic agarose gel showing RFLP detected by PCR-CAPS in the wild-type and mutant lox-1 gene. The AatII digestion fragments of the mutant gene include a unique 313 bp restriction fragment, indicated by an asterisk.

Digestion of the wild-type lox-1 PCR product yielded DNA fragments of 10, 179, and 462 bp, and the fragments from the mutant lox-1 PCR product were 10, 149, 179, and 313 bp, where additional DNA fragments were due to partial digestion of the lox-1 PCR product (FIG. 19). The fragment pattern corresponds to the expected RFLP resulting from this mutation, where the 313 bp fragment is unique to the mutant lox-1. This PCR-CAPS assay provides a reproducible and specific tool for identification of the lox-1 allele in barley and can thus be exploited in barley breeding programs aimed at introducing this gene in new barley varieties.

Example 5

Back-Crossing the Low Lipoxygenase Phenotype of Line G to cv Alexis Demonstrates a Genetic Linkage to the Mutant lox-1 Gene Repeated back-crossing was used to transfer the low-lipoxygenase phenotype from line G into a recurrent parent (in this case the cv. Alexis). The back-crossing program shown in FIG. 20, combined with selection for the low-lipoxygenase phenotype, progressively substitutes the Line G genome by the recurrent parent genome. Furthermore, other mutations introduced into the Line G genome during the sodium azide mutagenesis treatment will be eliminated. In the first back-cross of the homozygous low-lipoxygenase Line G (denoted genotype ll) to cv Alexis (denoted genotype LL) the progeny lines will be heterozygous (denoted genotype Ll). A low-lipoxygenase phenotype due to a recessive mutation will not be detectable in lines heterozygous for the mutation. The progeny are self-pollinated and will give a normal Mendelian segregating population, namely 1LL: 2Ll: 1 ll . The low lox homozygous ll genotype resulting from the first back-cross will have 50% cv Alexis genetic background. After ten rounds of back-crossing, the recurrent parent background will be approximately 99.9%.

*Hordeum vulgare*, L. cv Alexis and Line G were propagated in a greenhouse throughout the back-crossing program. Back-crossed progeny grains were germinated in petri dishes on filterpaper, soaked with 4 ml $H_2O$, for 3 days at 22° C. in the dark. The low-lipoxygenase lines were screened by measuring total lipoxygenase activity in extracts of the coleoptile (top 7 mm) from the germinating seedlings, as described in Example 1. Progeny of the $3^{rd}$ and $4^{th}$ back-cross were also analysed for inheritance of the mutant lox-1 gene using the PCR-CAPS assay described in Example 4.

Figure 20:
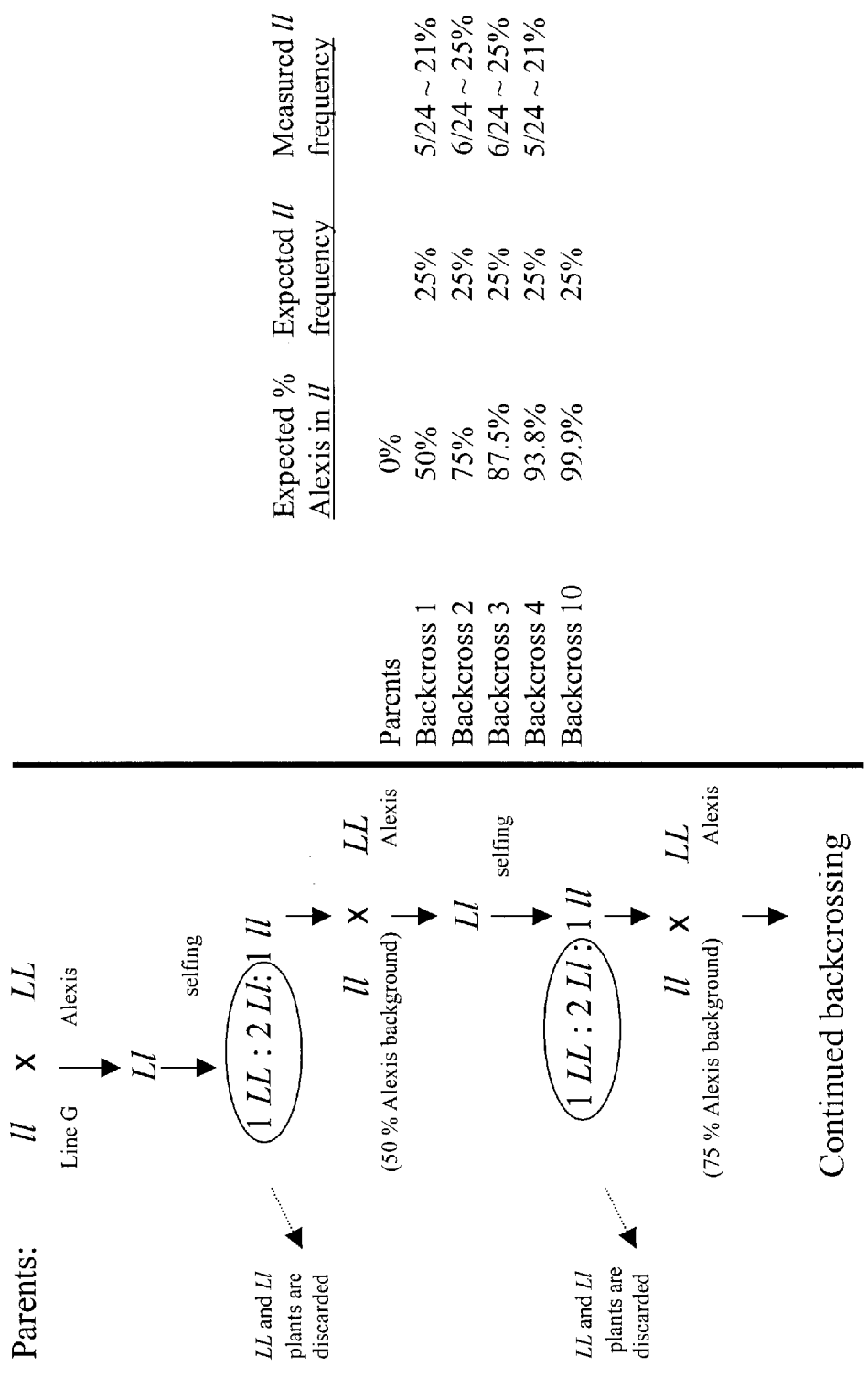
FIG. 20 is a table showing a back-crossing program for the single recessive gene pair ll (low lipoxygenase trait) of Line G to cv Alexis. The LL genotype are plants expressing wild-type lipoxygenase activity (dominant allele), the ll genotype are plants expressing the low-lipoxygenase (recessive allele). Ll are heterozygous plants containing both the wild-type and the low-lipoxygenase allele. Since the low-lipoxygenase trait is a recessive trait, Ll plants show wild-type lipoxygenase activity. After each round of back-crossing (including self-pollination), the ll progeny is expected to represent 25% of the progeny. The observed frequencies of low-lipoxygenase activity are indicated. The calculated percentage of the cv Alexis genetic background having the homozygous low-lipoxygenase allele is indicated as % Alexis.
Figure 21:
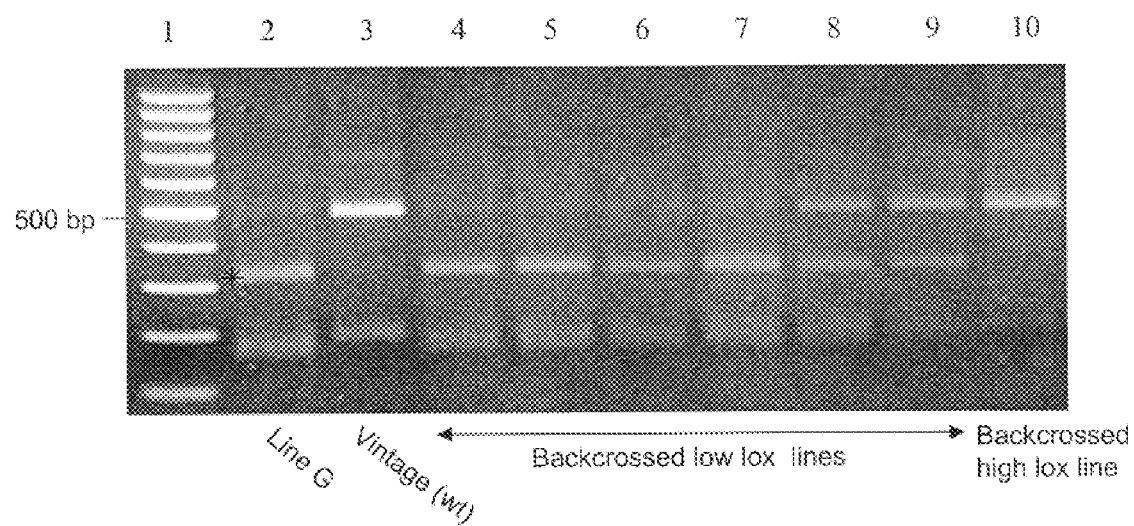
FIG. 21 is an electrophoretic agarose gel showing PCR-CAPS detection of the mutant lox-1 gene in ll progeny of the Line G-Alexis back-cross program. PCR-CAPS assay on genomic DNA of Line G (Lane 2), cv Vintage (Lane 3), ll progeny of $3^{rd}$ (Lane 4) and $4^{th}$ back-cross (Lanes 5–9). DNA ladder (Lane 1). Control, backcrossed high lox line (lane 10).

The expected frequency of the low-lipoxygenase phenotype in the segregating progeny of the four back-cross generations was 25% for a recessive mutation. The observed frequency of low-lipoxygenase activity in the progeny (24 grains) of the four back-cross generations is in agreement with the expected frequency (FIG. 20). When the $3^{rd}$ and $4^{th}$ back-cross progeny having the low lox homozygous ll genotype were analysed with the PCR-CAPS assay, they were all found to have the diagnostic 313 bp fragment, while progeny having wild-type lipoxygenase activity lacked this fragment (FIG. 21).

The back-crossing program demonstrates that the mutant lox-1 allele can be transferred to a new genetic background and is inherited in a recessive monofactorial manner following Mendelian segregation. Since the recurrent parent background is 93.8% in the $4^{th}$ back-cross progeny, the co-inheritance of the mutant lox-1 gene and the low-lipoxygenase phenotype provides confirmation of their genetic linkage.

Example 6

Beer Brewed From Line G Barley Malt Accumulates Less trans-2-nonenal During Storage, Giving an Improved Flavour Stability

*Hordeum vulgare* L cv Vintage and Line G were propagated in the field over several seasons in order to provide sufficient grain for industrial malting. The following industrial scale malting and brewing trials as well as analyses of the finished beer were performed to demonstrate the value of the Line G low-lipoxygenase barley for improved flavour stability.

1. Industrial Malting and Kilning of Line G and cv Vintage

Malting was performed on a 10-ton scale in an industrial malthouse in two trials as follows:

Trial 1: Line G Barley Grain (1996 Harvest)

Steeping conditions: 8 hours wet; 14 hours dry; 8 hours wet; 10 hours dry; 4 hours wet in 16° C. steeping water. Malting conditions: 12 hours at 18° C.; 24 hours at 16° C.; 24 hours at 14° C.; 60 hours at 12° C. Kilning conditions: 12 hours at 60° C.; 3 hours at 68° C.; 4 hours at 74° C.; 3 hours at 80° C.

Trial 2: cv Vintage and Line G (1996/1997 Harvest)

Steeping conditions: 8 hours wet; 10 hours dry; 6 hours wet; 15 hours dry; 4 hours wet in 15° C. steeping water. Malting conditions: 5 days with inlet air at 15° C. and spraying to maintain moisture level. Kilning conditions: 10 hours at 50° C.; 2 hours at 60° C.; 2.5 hours at 80° C.

Malting analyses of 2 samples of the Line G malt from Trial 1 compared to the control malt, cv Nevada (Table 1) and from Trial 2 compared to cv Vintage (Table 2) confirmed that Line G malt was suitable for brewing trials.

TABLE 1

MALTING TRIAL 1

| Malt analyses | | Barley variety | | |
|---|---|---|---|---|
| | | cv Nevada | Line G | Line G |
| | | Crop year | | |
| | | 1996 | 1996 | 1996 |
| Moisture content | % | 4.7 | 4.3 | 4.4 |
| Extract fine as is. | % ai. | 76.9 | 76.1 | 75.3 |
| Extract fine d.m. | % dm. | 81.4 | 79.5 | 78.7 |
| Saccharification time | Min | <10 | <10 | <10 |
| Diastatic power | % WK | 252 | 373 | 365 |
| Color | EBC | 2.8 | 4.4 | 3.8 |
| pH | | 6.16 | 5.97 | 5.99 |
| Turbidity | EBC | 9.0 | 2.5 | 2.4 |
| Total protein d.m. | % | 10.35 | 10.74 | 12.03 |
| Soluble nitrogen | mg/l | 647 | 787 | 765 |
| Sol. Protein % malt d.m. | % dm. | 3.7 | 4.4 | 4.3 |
| Kolbach | | 35.3 | 40.8 | 35.4 |
| Free Amino Nitrogen | mg/l | 97 | 125 | 118 |
| Friability | % | 89.5 | 85.6 | 89.5 |
| Whole unmodified grains | % | 1.1 | 0.6 | 0.5 |
| Partly unmodified grains | % | 2.3 | 1.0 | 0.6 |
| β-glucan in wort | mg/l | 114 | 66 | 36 |
| β-glucan in malt | % w/w | 0.24 | 0.11 | 0.05 |
| S-methylmethionine/DMS eq. | μg/g | 2.4 | 6.4 | 8.4 |
| Free DMS | μg/g | 1.0 | 6.6 | 4.7 |
| NDMA | μg/kg | n.d. | 0.3/0.6 | 0.3/0.3 |

TABLE 2

MALTING TRIAL 2

| | | Barley variety | | |
|---|---|---|---|---|
| | | Vintage | Line G | Line G |
| | | Crop year | | |
| | | 1996 | 1996 | 1997 |
| Moisture content | % | 4.1 | 4.1 | 4.3 |
| Extract fine as is. | % ai. | 77.0 | 75.6 | 77.5 |
| Extract fine d.m. | % dm. | 80.3 | 78.8 | 80.9 |

TABLE 2-continued

MALTING TRIAL 2

| | | Barley variety | | |
|---|---|---|---|---|
| | | Vintage | Line G | Line G |
| | | | Crop year | |
| | | 1996 | 1996 | 1997 |
| Fine/coarse difference | % dm. | 0.7 | 1.6 | 1.7 |
| Saccharification time | min | — | — | <10 |
| Diastatic power | % WK | 343 | 342 | 268 |
| Color | EBC | 2.5 | 2.8 | 3.4 |
| PH | | 6.05 | 6.01 | 6.12 |
| Turbidity | EBC | 1.5 | 1.3 | 2.5 |
| Total protein d.m. | % | 10.98 | 12.22 | 9.82 |
| Soluble nitrogen | mg/l | 696 | 741 | 610 |
| Sol. Protein % malt d.m. | % dm. | 3.9 | 4.1 | 3.4 |
| Kolbach | | 35.2 | 33.7 | 34.6 |
| Free Amino Nitrogen | mg/l | 110 | 117 | 100 |
| Friability | % | 91.3 | 81.8 | 89.5 |
| Whole unmodified grains | % | 0.7 | 1.1 | 1.3 |
| Partly unmodified grains | % | 1.0 | 2.7 | 2.7 |
| β-glucan in wort | mg/l | 97 | 172 | 117 |
| Beta-glucan in malt | % w/w | — | — | 0.3 |
| S-methylmethionine/DMS eq. | µg/g | — | — | — |
| Free DMS | µg/g | — | — | — |

2. Industrial Brewing with Line G, cv Vintage Malt, and Control Malt cv Nevada

Two brewing trials were performed, using wort prepared from Line G and control malt cv Nevada malt in Trial 1 and from Line G and control malt cv Vintage in Trial 2.

Beer was brewed on a 30-hl industrial scale with 475 kg malt according to the following scheme: Mashing in at 50° C.; 30 minutes at 50° C.; 30 minutes heating from 50–70° C.; 15 minutes at 70° C. A portion of the wort was heated for 20 minutes from 70–100° C. and 5 minutes at 100° C., while the main mash was kept at 70° C. for another 25 minutes and then the two mashes was combined and kept for 10 minutes at 76° C. The brewing steps of wort boiling, whirlpool separation of spent grain, cooling, fermentation, lagering and packaging in brown glass bottles were according to standard brewing practise.

3. Flavor Stability and T2N Content of Beer Brewed from Line G, cv Vintage Malt and Control Malt cv Nevada The freshly bottled beer was stored at 5° C. and analysed within 2 months of production. The flavor-stability of the fresh and stored beer was evaluated in two independent laboratories following two different types of beer storage conditions. In laboratory A the beer was subjected to a forced aging process, where the beer was stored at 37° C. for a period of 7 days, while in laboratory B the beer was stored at 30° C. for 6 and 12 weeks. Trans-2-nonenal levels in beer were determined by gas chromatography and mass spectrometric detection following derivatisation of carbonyls with O-(2,3,4,5,6-pentafluorobenzyl)-hydroxylamine, essentially as described by Grönqvist et al. 1993 *Proceedings of the 24th EBC Congress*, Oslo, 421–428. A trained beer taste panel evaluated the overall flavor score of the beer, which includes detection of a cardboard flavor, indicative of free trans-2-nonenal in the beer.

Laboratory A: Forced-Aging Tolerance

Comparison of beer, brewed from Line G and the control malt, cv Nevada, in the first brewing trial (Table 3) demonstrated that beer from Line G had a greater flavor stability and a lower trans-2-nonenal content following forced-aging as compared to the controls. The second trial, comparing beer brewed from Line G malt with beer brewed from cv Vintage malt, the parental cultivar, confirmed the initial data (Table 4).

TABLE 3

BREWING TRIAL 1

| Barley Malt | cv Nevada | Line G |
|---|---|---|
| SO$_2$ Content (mg/ml) | 1 | 1 |
| T2N**(ppb) - Fresh Beer | 0.009 | 0.005 |
| T2N**(ppb) - Aged Beer (37° C./7 DAY) | 0.117 | 0.025 |
| Flavor* - Fresh Beer | 5.9 | 5.3 |
| Flavor* - Aged Beer (37° C./7 DAY) | 1.3 | 5.1 |

*Flavor evaluation scale 1–10 of increasing quality;
**trans-2-nonenal.

TABLE 4

BREWING TRIAL 2

| Barley Malt | cv Vintage | Line G |
|---|---|---|
| SO$_2$ Content (mg/ml) | 2 | 2.5 |
| T2N**(ppb) - Fresh Beer | 0.023 | 0.019 |
| T2N**(ppb) - Aged Beer (37° C./7 Day) | 0.078 | 0.035 |
| FLAVOR* - Fresh Beer | 5.5 | 6.1 |
| FLAVOR* - Aged Beer (37° C./7 Day) | 2.9 | 5.9 |

*Flavor evaluation scale 1–10 of increasing quality;
**trans-2-nonenal.

Laboratory B: 30° C. Storage Tolerance

Beer brewed from Line G malt had lower trans-2-nonenal levels following 6 and 12 weeks at the elevated storage temperature of 30° C., when compared to beer brewed from either of the reference malts (Table 5 and 6) and had a better flavor-stability as judged by a taste panel. The taste-threshold for trans-2-nonenal in these analysed beers lies close to 0.08 ppb.

TABLE 5

BREWING TRIAL 1

| Barley Malt | cv Nevada | Line G |
|---|---|---|
| trans-2-nonenal (ppb) - Fresh Beer | 0.050 | 0.044 |
| trans-2-nonenal (ppb) - 30° C./6 weeks | 0.072 | 0.037 |
| trans-2-nonenal (ppb) - 30° C./12 weeks | 0.095 | 0.046 |
| trans-2-nonenal flavor* - Fresh Beer | 0.6 | 0.3 |
| trans-2-nonenal flavor* - 30° C./6 weeks | 3.7 | 1.4 |
| trans-2-nonenal flavor* - 30° C./12 weeks | 2.5 | 0.6 |

*trans-2-nonenal flavor detection score on a scale of 1–10

TABLE 6

BREWING TRIAL 2

| Barley Malt | cv Vintage | Line G |
|---|---|---|
| trans-2-nonenal (ppb) - Fresh Beer | 0.070 | 0.062 |
| trans-2-nonenal (ppb) - 30° C./6 weeks | 0.093 | 0.070 |
| trans-2-nonenal (ppb) - 30° C./12 weeks | 0.133 | 0.080 |
| trans-2-nonenal flavor* - Fresh Beer | 0.3 | 0.9 |
| trans-2-nonenal flavor* - 30° C./6 weeks | 2.5 | 1.7 |
| trans-2-nonenal flavor* - 30° C./12 weeks | 2.2 | 1.3 |

*trans-2-nonenal flavor detection score on a scale of 1–10

The improved flavor-stability of beer brewed from Line G malt, as measured by the levels of trans-2-nonenal detected in the beer following storage at 30° C. from the combined brewing trial data, is shown to be statistically significant (Table 7).

TABLE 7

TRANS-2-NONENAL IN STORED BEER

| | Mean | Stdev | Difference | 2-tailed p | Significant (p < 0.05) |
|---|---|---|---|---|---|
| fresh | | | | | |
| reference | 0.060 | 0.012 | 0.007 | 0.34 | no |
| line-G | 0.053 | 0.011 | | | |
| 6 weeks, 30° C. | | | | | |
| reference | 0.083 | 0.013 | 0.029 | 0.031 | yes |
| line-G | 0.054 | 0.021 | | | |
| 12 weeks, 30° C. | | | | | |
| reference | 0.114 | 0.023 | 0.051 | 0.003 | yes |
| line-G | 0.063 | 0.020 | | | |

Since the natural sulfite levels were low in both brewing trials, the free trans-2-nonenal levels in the aged beer would closely reflect the trans-2-nonenal potential of the different beers, namely the level of trans-2-nonenal adducts present in the fresh beer. Addition of sulfite can temporarily delay the staling process, by complexing free-trans-2-nonenal, until sulfite levels are reduced by oxidation due to gaseous exchange through the packaging.

The described brewing trials with low-LOX-1 barley malt provide the first unequivocal evidence that LOX-1 activity in barley during the malting and brewing process is a key determinant of the appearance of the off-flavor compound trans-2-nonenal in aged beer.

The above specification includes citations to numerous publications. Each publication is hereby incorporated by reference for all purposes, as if fully set forth.

We claim:

1. A barley plant or portion thereof, comprising a mutated LOX-1 protein having the amino acid sequence of SEQ ID NO: 12, wherein Xaa is an acidic, basic, or polar amino acid, the plant or portion characterized by a reduction or absence of LOX-1 activity as compared with a non-mutated control.

2. The barley plant or portion of claim 1, wherein Xaa is glutamic acid or aspartic acid.

3. The barley plant or portion of claim 2, wherein Xaa is aspartic acid.

4. Grain or plant progeny produced from the barley plant or plant portion and comprising the mutated LOX-1 protein of claim 1.

5. A plant product produced from the barley plant or plant portion and comprising the mutated LOX-1 protein of claim 1.

6. A method for producing a beverage having stable organoleptic qualities, comprising brewing of the plant or plant portion of claim 1 comprising the mutated LOX-1 protein, wherein the beverage presents stable organoleptic qualities that remain stable over a measured period of time or at elevated storage temperatures as compared with a control beverage.

7. A method for producing beer comprising brewing beer from the barley plant or plant portion of claim 1 comprising the mutated LOX-1 protein.

8. A method for producing a beer having stabilized organoleptic properties, comprising brewing beer from the barley plant or plant portion of claim 1 comprising the mutated LOX-1 protein, wherein said brewed beer has reduced levels of trans-2-nonenal over a measured period of time or under conditions of elevated storage temperature, as compared with a control beer brewed with a non-mutated barley.

9. The plant product of claim 5, wherein the product is malt.

10. A method for producing a beverage having stable organoleptic qualities, comprising processing the plant or plant portion of claim 1 comprising the mutated LOX-1 protein into a beverage wherein the beverage presents stable organoleptic qualities that remain stable over a measured period of time or at elevated storage temperatures as compared with a control beverage.

11. Malt produced by malting the grain of claim 4.

* * * * *

```
                          SEQUENCE LISTING

<160> NUMBER OF SEQ ID NOS:   18

<210> SEQ ID NO 1
<211> LENGTH: 143
<212> TYPE: DNA
<213> ORGANISM: Hordeum vulgare

<400> SEQUENCE: 1
ctaagccatc ggcaaccatg gatgaataaa gggcgttcgc cacgtacgaa acttgtcgag         60
agattggtgt agtgtgtgtc tgtgacagta ctatgtcagc agttgctctt taagccgaat        120
aaataaagca gatttgcttc caa                                                143

<210> SEQ ID NO 2
<211> LENGTH: 24
<212> TYPE: DNA
<213> ORGANISM: Hordeum vulgare

<400> SEQUENCE: 2
gaaaagcttg gaggtagacg ctgc                                                24

<210> SEQ ID NO 3
<211> LENGTH: 33
<212> TYPE: DNA
<213> ORGANISM: Hordeum vulgare

<400> SEQUENCE: 3
tataggatcc ttgttcttgg cctcctctcc tcg                                      33

<210> SEQ ID NO 4
<211> LENGTH: 22
<212> TYPE: DNA
<213> ORGANISM: Hordeum vulgare

<400> SEQUENCE: 4
agtgaaaaac agtgtgctgg tg                                                  22
```

<210> SEQ ID NO 5
<211> LENGTH: 21
<212> TYPE: DNA
<213> ORGANISM: Hordeum vulgare

<400> SEQUENCE: 5
ggcttaaaga gcaactgctg a                                        21

<210> SEQ ID NO 6
<211> LENGTH: 23
<212> TYPE: DNA
<213> ORGANISM: Hordeum vulgare

<400> SEQUENCE: 6
caagatgcat atgctgctgg gag                                      23

<210> SEQ ID NO 7
<211> LENGTH: 29
<212> TYPE: DNA
<213> ORGANISM: Hordeum vulgare

<400> SEQUENCE: 7
cgatggttta aattagatgg agatgctgt                                29

<210> SEQ ID NO 8
<211> LENGTH: 4663
<212> TYPE: DNA
<213> ORGANISM: Hordeum vulgare

<400> SEQUENCE: 8

| | | | | | |
|---|---|---|---|---|---|
| cagccccatg | catgcacatg | cacatgcaca | tgcacatgca | gtgcagccaa | gcaccgctcg | 60 |
| atgggcgatc | acccgtcacg | ggaccggagc | gcgccatgcg | aagcacgagg | agggcacgtc | 120 |
| accgtccgcg | cgcagcacgt | ggagagcacg | tcgccgtccg | atccatctct | ccaaagccga | 180 |
| gcgccacacc | accgggaccg | gacccggacc | ggcctataaa | ttgcccggac | cgagctgcaa | 240 |
| gcagctcctc | acacacactc | acgcaacaca | catccatctt | cactgaaaag | tgaaaaacag | 300 |
| tgtgctggtg | ccattggttg | gagcagtgaa | agcgaggaga | ggaggccaag | aacaagatgc | 360 |
| tgctgggagg | gctgatcgac | accctcacgg | ggcgaacaa | gagcgcccgg | ctcaagggca | 420 |
| cggtggtgct | catgcgcaag | aacgtgctgg | acctcaacga | cttcggcgcc | accatcatcg | 480 |
| acggcatcgg | cgagttcctc | ggcaagggcg | tcacctgcca | gcttatcagc | tccaccgccg | 540 |
| tcgaccaagg | taatcactac | cctcctccgg | ccttctcctc | tgtttacaag | atatagtatt | 600 |
| tctttcgtgt | gggccggcgg | ccatggatgg | atggatgtgt | ctggatcggc | taagaagat | 660 |
| aggatagcta | gccctggccg | gtcgtcttta | cctgagcatg | gcatatgcc | atcgaaaaaa | 720 |
| gagacaacag | catgcatgca | tggtgcgcgc | accagaccac | gcagagcacc | ggatgctcga | 780 |
| gacaaagcaa | cacaacaagc | aaggacgaca | cgtcaaaagc | aacacaacaa | gcaaggacgg | 840 |
| cacgtcaaaa | gcaacacaaa | cctaaactaa | agcacaaaga | cgtaagagca | agcacacaat | 900 |
| cagcaggcta | taaacagttg | tcatcaaaaa | caacgctgga | agagagagag | aaggaaggaa | 960 |
| gtagtagcca | tgaaaaatta | aatcaccggg | cgttgctctt | tgcccaacaa | ttaatcaagc | 1020 |
| agggtacgtg | gcatgtatag | ttcttgtaag | taaactaagc | atgtgatatg | agaaggtacg | 1080 |
| tggtggtgca | gacaacggcg | gtcgcgggaa | ggtgggcgcg | gaggcggagc | tggagcagtg | 1140 |
| ggtgacgagc | ctgccgtcgc | tgacgacggg | ggagtccaag | ttcggcctca | ccttcgactg | 1200 |
| ggaggtggag | aagctcgggg | tgccgggcgc | catcgtcgtc | aacaactacc | acagctccga | 1260 |

-continued

```
gttcctgctt aaaaccatca ccctccacga cgtccccggc cgcagcggca acctcacctt    1320
cgtcgccaac tcatggatct accccgccgc caactaccga tacagccgcg tcttcttcgc    1380
caacgacgtg cgtggatttt cctctacttt cctctccttt cattttcacc gccttcgtca    1440
ttcatggtcg atcattaagt cttgccagga caatagatga tgagctagga gtggttacca    1500
cttagcagta cgtacattat ttattccgtg ttggtagaaa aggatatggt ttggtgcaga    1560
tcgacacaag attgaatgaa agttgcaccg tggcaccgtg gcagcgtggt aggtgaaaat    1620
aactgttgca cggatccacc cacatgattg ttttcatgaa taaactttt aaggatgtgt     1680 ctagccacat ctagatgcat gtcacataat tattgcatac caaaacgatt aaattaagca    1740 taaaagaaa aggaaaaaa tactcacata tctcgacgta agatcaatga tatagtattt      1800
agatatgcaa tatttatctt acatctaaac ctttcttcat tcttaaatat aagacatttg    1860
taagatttca ctatggacaa catacgaaac aaaatcagtg gatctctcta tgcattcatt    1920
atgtagtcta taataaaatc tttaaagat cgtatatttt gcaacggagg gagtaaaaca     1980 taactttta atagtaatgt tgcacggctc cacactcgca gacgtacctg ccgagccaga     2040
tgccggcggc gctgaagccg taccgcgacg acgagctccg gaacctgcgt ggcgacgacc    2100
agcagggccc gtaccaggag cacgaccgca tctaccgcta cgacgtctac aacgacctcg    2160
gcgagggccg ccccatcctc ggcggcaact ccgaccaccc ttacccgcgc cgcggccgca    2220
cggagcgcaa gcccaacgcc agcgacccga gcctggagag ccggctgtcg ctgctggagc    2280
agatctacgt gccgcgggac gagaagttcg gccacctcaa gacgtccgac ttcctgggct    2340
actccatcaa ggccatcacg cagggcatcc tgccggccgt cgcacctac gtggacacca     2400 cccccggcga gttcgactcc ttccaggaca tcatcaacct ctatgagggc ggcatcaagc    2460
tgcccaaggt ggccgccctg gaggagctcc gtaagcagtt cccgctccag ctcatcaagg    2520
acctcctccc cgtcggcggc gactccctgc ttaagctccc cgtgccccac atcatccagg    2580
agaacaagca ggcgtggagg accgacgagg agttcgcacg ggaggtgctc gccggcgtca    2640
acccggtcat gatcacgcgt ctcacggtga gtcagcgatt atttgttcat tgtgtgtgta    2700
tggtgtccat ggtgagaaag tgcagatctt gatttgcgtt gggtcgcatg cacgcatgct    2760
gcatgcatgc aggagttccc gccaaaaagt agtctggacc ctagcaagtt tggtgaccac    2820
accagcacca tcacggcgga gcacatagag aagaacctcg agggcctcac ggtgcagcag    2880
gtaattggtc caagccatcg acatcaacta tgatttacct aggagtaatt ggtagctgta    2940
gataatttgg cttcgttgca attaatttga tgctggccga tcaagtgatc gtattgggtt    3000
tgaaatttgc aggcgctgga agcaacagg ctgtacatcc ttgatcacca tgaccggttc     3060
atgccgttcc tgatcgacgt caacaacctg cccggcaact tcatctacgc cacgaggacc    3120
ctcttcttcc tgcgcggcga cggcaggctc acgccgctcg ccatcgagct gagcgagccc    3180
atcatccagg cggccttac acggccaag agcaaggttt acacgccggt gcccagcggc      3240
tccgtcgaag ctgggtgtg ggagctcgcc aaggcctacg tcgccgtcaa tgactccggg     3300
tggcaccagc tcgtcagcca ctggtacgtt ctccacggtc gatgtgattc agtcagtcga    3360
tgcacaacaa ctgatcgaaa tatgattgat tgaaacgcgc aggctgaaca ctcacgcggt    3420
gatggagccg ttcgtgatct cgacgaaccg gcaccttagc gtgacgcacc cggtgcacaa    3480
gctgctgagc ccgcactacc gcgacaccat gaccatcaac gcgctggcgc ggcagacgct    3540
catcaacgcc ggcggcatct cgagatgac ggtgttcccg ggcaagttcg cgttggggat     3600
```

```
gtcggccgtg gtgtacaagg actggaagtt caccgagcag ggactgccgg acgatctcat    3660
caagaggtac gtacctggta aatgttatga atgtgtaaaa caaattgggc gtctcgctca    3720
ctgacaggaa cgtggtaaaa aaaatgcagg ggcatggcgg tggaggaccc gtcgagcccg    3780
tacaaggtgc ggttgctggt gtcggactac ccgtacgcgg cggacgggct ggcgatctgg    3840
cacgccattg agcagtacgt gagcgagtac ctggccatct actacccgaa cgacggcgtg    3900
ctgcagggcg atacggaggt gcaggcgtgg tggaaggaga cgcgcgaggt cgggcacggc    3960
gacctcaagg acgccccatg gtggcccaag atgcaaagtg tgccggagct ggccaaggcg    4020
tgcaccacca tcatctggat cgggtcggcg ctgcatgcgg cagtcaactt cgggcagtac    4080
ccctacgcgg ggttcctccc gaaccggccg acggtgagcc ggcgccgcat gccggagccc    4140
ggcacggagg agtacgcgga gctggagcgc gacccggagc gggccttcat ccacaccatc    4200
acgagccaga tccagaccat catcggcgtg tcgctgctgg aggtgctgtc gaagcactcc    4260
tccgacgagc tgtacctcgg gcagcgggac acgccggagt ggacctcgga cccaaaggcc    4320
ctggaggtgt tcaagcggtt cagcgaccgg ctggtggaga tcgagagcaa ggtggtgggc    4380
atgaaccatg acccggagct caagaaccgc aacggcccgg ctaagtttcc ctacatgctg    4440
ctctacccca cacctccga ccacaagggc gccgctgccg ggcttaccgc caagggcatc    4500
cccaacagca tctccatcta atctaagcca tcggcaacca tggatgaata aagggcgttc    4560
gccacgtacg aaacttgtcg agagattggt gtagtgtgtg tctgtgacag tactatgtca    4620
gcagttgctc tttaagccga ataaataaag cagatttgct tcc                      4663
```

<210> SEQ ID NO 9
<211> LENGTH: 862
<212> TYPE: PRT
<213> ORGANISM: Hordeum vulgare

<400> SEQUENCE: 9

```
Met Leu Leu Gly Gly Leu Ile Asp Thr Leu Thr Gly Ala Asn Lys Ser
1               5                   10                  15

Ala Arg Leu Lys Gly Thr Val Val Leu Met Arg Lys Asn Val Leu Asp
            20                  25                  30

Leu Asn Asp Phe Gly Ala Thr Ile Ile Asp Gly Ile Gly Glu Phe Leu
        35                  40                  45

Gly Lys Gly Val Thr Cys Gln Leu Ile Ser Ser Thr Ala Val Asp Gln
    50                  55                  60

Asp Asn Gly Gly Arg Gly Lys Val Gly Ala Glu Ala Leu Glu Gln
65                  70                  75                  80

Trp Val Thr Ser Leu Pro Ser Leu Thr Thr Gly Glu Ser Lys Phe Gly
                85                  90                  95

Leu Thr Phe Asp Trp Glu Val Glu Lys Leu Gly Val Pro Gly Ala Ile
            100                 105                 110

Val Val Asn Asn Tyr His Ser Ser Glu Phe Leu Leu Lys Thr Ile Thr
        115                 120                 125

Leu His Asp Val Pro Gly Arg Ser Gly Asn Leu Thr Phe Val Ala Asn
    130                 135                 140

Ser Trp Ile Tyr Pro Ala Ala Asn Tyr Arg Tyr Ser Arg Val Phe Phe
145                 150                 155                 160

Ala Asn Asp Thr Tyr Leu Pro Ser Gln Met Pro Ala Ala Leu Lys Pro
                165                 170                 175

Tyr Arg Asp Asp Glu Leu Arg Asn Leu Arg Gly Asp Asp Gln Gln Gly
            180                 185                 190
```

-continued

```
Pro Tyr Gln Glu His Asp Arg Ile Tyr Arg Tyr Asp Val Tyr Asn Asp
            195                 200                 205

Leu Gly Glu Gly Arg Pro Ile Leu Gly Gly Asn Ser Asp His Pro Tyr
            210                 215                 220

Pro Arg Arg Gly Arg Thr Glu Arg Lys Pro Asn Ala Ser Asp Pro Ser
225                 230                 235                 240

Leu Glu Ser Arg Leu Ser Leu Glu Gln Ile Tyr Val Pro Arg Asp
                245                 250                 255

Glu Lys Phe Gly His Leu Lys Thr Ser Asp Phe Leu Gly Tyr Ser Ile
            260                 265                 270

Lys Ala Ile Thr Gln Gly Ile Leu Pro Ala Val Arg Thr Tyr Val Asp
            275                 280                 285

Thr Thr Pro Gly Glu Phe Asp Ser Phe Gln Asp Ile Ile Asn Leu Tyr
            290                 295                 300

Glu Gly Gly Ile Lys Leu Pro Lys Val Ala Leu Glu Glu Leu Arg
305                 310                 315                 320

Lys Gln Phe Pro Leu Gln Leu Ile Lys Asp Leu Leu Pro Val Gly Gly
                325                 330                 335

Asp Ser Leu Leu Lys Leu Pro Val Pro His Ile Ile Gln Glu Asn Lys
            340                 345                 350

Gln Ala Trp Arg Thr Asp Glu Glu Phe Ala Arg Glu Val Leu Ala Gly
            355                 360                 365

Val Asn Pro Val Met Ile Thr Arg Leu Thr Glu Phe Pro Pro Lys Ser
            370                 375                 380

Ser Leu Asp Pro Ser Lys Phe Gly Asp His Thr Ser Thr Ile Thr Ala
385                 390                 395                 400

Glu His Ile Glu Lys Asn Leu Glu Gly Leu Thr Val Gln Gln Ala Leu
                405                 410                 415

Glu Ser Asn Arg Leu Tyr Ile Leu Asp His His Asp Arg Phe Met Pro
            420                 425                 430

Phe Leu Ile Asp Val Asn Asn Leu Pro Gly Asn Phe Ile Tyr Ala Thr
            435                 440                 445

Arg Thr Leu Phe Phe Leu Arg Gly Asp Gly Arg Leu Thr Pro Leu Ala
            450                 455                 460

Ile Glu Leu Ser Glu Pro Ile Ile Gln Gly Gly Leu Thr Thr Ala Lys
465                 470                 475                 480

Ser Lys Val Tyr Thr Pro Val Pro Ser Gly Ser Val Glu Gly Trp Val
                485                 490                 495

Trp Glu Leu Ala Lys Ala Tyr Val Ala Val Asn Asp Ser Gly Trp His
            500                 505                 510

Gln Leu Val Ser His Trp Leu Asn Thr His Ala Val Met Glu Pro Phe
            515                 520                 525

Val Ile Ser Thr Asn Arg His Leu Ser Val Thr His Pro Val His Lys
            530                 535                 540

Leu Leu Ser Pro His Tyr Arg Asp Thr Met Thr Ile Asn Ala Leu Ala
545                 550                 555                 560

Arg Gln Thr Leu Ile Asn Ala Gly Gly Ile Phe Glu Met Thr Val Phe
                565                 570                 575

Pro Gly Lys Phe Ala Leu Gly Met Ser Ala Val Val Tyr Lys Asp Trp
            580                 585                 590

Lys Phe Thr Glu Gln Gly Leu Pro Asp Asp Leu Ile Lys Arg Gly Met
            595                 600                 605
```

-continued

```
Ala Val Glu Asp Pro Ser Ser Pro Tyr Lys Val Arg Leu Leu Val Ser
    610                 615                 620

Asp Tyr Pro Tyr Ala Ala Asp Gly Leu Ala Ile Trp His Ala Ile Glu
625                 630                 635                 640

Gln Tyr Val Ser Glu Tyr Leu Ala Ile Tyr Tyr Pro Asn Asp Gly Val
            645                 650                 655

Leu Gln Gly Asp Thr Glu Val Gln Ala Trp Trp Lys Glu Thr Arg Glu
        660                 665                 670

Val Gly His Gly Asp Leu Lys Asp Ala Pro Trp Trp Pro Lys Met Gln
    675                 680                 685

Ser Val Pro Glu Leu Ala Lys Ala Cys Thr Thr Ile Ile Trp Ile Gly
690                 695                 700

Ser Ala Leu His Ala Ala Val Asn Phe Gly Gln Tyr Pro Tyr Ala Gly
705                 710                 715                 720

Phe Leu Pro Asn Arg Pro Thr Val Ser Arg Arg Met Pro Glu Pro
            725                 730                 735

Gly Thr Glu Glu Tyr Ala Glu Leu Glu Arg Asp Pro Glu Arg Ala Phe
        740                 745                 750

Ile His Thr Ile Thr Ser Gln Ile Gln Thr Ile Ile Gly Val Ser Leu
    755                 760                 765

Leu Glu Val Leu Ser Lys His Ser Ser Asp Glu Leu Tyr Leu Gly Gln
770                 775                 780

Arg Asp Thr Pro Glu Trp Thr Ser Asp Pro Lys Ala Leu Glu Val Phe
785                 790                 795                 800

Lys Arg Phe Ser Asp Arg Leu Val Glu Ile Glu Ser Lys Val Val Gly
            805                 810                 815

Met Asn His Asp Pro Glu Leu Lys Asn Arg Asn Gly Pro Ala Lys Phe
        820                 825                 830

Pro Tyr Met Leu Leu Tyr Pro Asn Thr Ser Asp His Lys Gly Ala Ala
    835                 840                 845

Ala Gly Leu Thr Ala Lys Gly Ile Pro Asn Ser Ile Ser Ile
850                 855                 860
```

<210> SEQ ID NO 10
<211> LENGTH: 2818
<212> TYPE: DNA
<213> ORGANISM: Hordeum vulgare

<400> SEQUENCE: 10

| | | |
|---|---|---|
| agtgaaaaac agtgtgctgg tgccattggt tggagcagtg aaagcgagga gaggaggcca | 60 |
| agaacaagat gctgctggga gggctgatcg acaccctcac gggggcgaac aagagcgccc | 120 |
| ggctcaaggg cacggtggtg ctcatgcgca agaacgtgct ggacctcaac gacttcggcg | 180 |
| ccaccatcat cgacggcatc ggcgagttcc tcggcaaggg cgtcacctgc cagcttatca | 240 |
| gctccaccgc cgtcgaccaa gacaacggcg gtcgcgggaa ggtgggcgcg gaggcggagc | 300 |
| tggagcagtg ggtgacgagc ctgccgtcgc tgacgacggg ggagtccaag ttcggcctca | 360 |
| ccttcgactg ggaggtggag aagctcgggg tgccgggcgc catcgtcgtc aacaactacc | 420 |
| acagctccga gttcctgctt aaaaccatca ccctccacga cgtccccggc cgcagcggca | 480 |
| acctcacctt cgtcgccaac tcatggatct accccgccgc caactaccga tacagccgcg | 540 |
| tcttcttcgc caacgacacg tacctgccga gccagatgcc ggcggcgctg aagccgtacc | 600 |
| gcgacgacga gctccggaac ctgcgtggcg acgaccagca gggcccgtac caggagcacg | 660 |
| accgcatcta ccgctacgac gtctacaacg acctcggcga gggccgcccc atcctcggcg | 720 |

```
gcaactccga ccacccttac ccgcgccgcg gccgcacgga gcgcaagccc aacgccagcg    780
acccgagcct ggagagccgg ctgtcgctgc tggagcagat ctacgtgccg cgggacgaga    840
agttcggcca cctcaagacg tccgacttcc tgggctactc catcaaggcc atcacgcagg    900
gcatcctgcc ggccgtgcgc acctacgtgg acaccacccc cggcgagttc gactccttcc    960
aggacatcat caacctctat gagggcggca tcaagctgcc caaggtggcc gccctggagg   1020
agctccgtaa gcagttcccg ctccagctca tcaaggacct cctccccgtc ggcggcgact   1080
ccctgcttaa gctccccgtg ccccacatca tccaggagaa caagcaggcg tggaggaccg   1140
acgaggagtt cgcacgggag gtgctcgccg gcgtcaaccc ggtcatgatc acgcgtctca   1200
cggagttccc gccaaaaagt agtctggacc ctagcaagtt tggtgaccac accagcacca   1260
tcacggcgga gcacatagag aagaacctcg agggcctcac ggtgcagcag gcgctggaaa   1320
gcaacaggct gtacatcctt gatcaccatg accggttcat gccgttcctg atcgacgtca   1380
acaacctgcc cggcaacttc atctacgcca cgaggaccct cttcttcctg cgcggcgacg   1440
gcaggctcac gccgctcgcc atcgagctga gcgagcccat catccagggc ggccttacca   1500
cggccaagag caaggtttac acgccggtgc ccagcggctc cgtcgaaggc tgggtgtggg   1560
agctcgccaa ggcctacgtc gccgtcaatg actccgggtg gcaccagctc gtcagccact   1620
ggctgaacac tcacgcggtg atggagccgt tcgtgatctc gacgaaccgg caccttagcg   1680
tgacgcaccc ggtgcacaag ctgctgagcc cgcactaccg cgacaccatg accatcaacg   1740
cgctggcgcg gcagacgctc atcaacgccg gcggcatctt cgagatgacg gtgttcccgg   1800
gcaagttcgc gttggggatg tcggccgtgg tgtacaagga ctggaagttc accgagcagg   1860
gactgccgga cgatctcatc aagaggggca tggcggtgga ggacccgtcg agcccgtaca   1920
aggtgcggtt gctggtgtcg gactacccgt acgcggcgga cgggctggcg atctggcacg   1980
ccattgagca gtacgtgagc gagtacctgg ccatctacta cccgaacgac ggcgtgctgc   2040
agggcgatac ggaggtgcag gcgtggtgga aggagacgcg cgaggtcggg cacggcgacc   2100
tcaaggacgc cccatggtgg cccaagatgc aaagtgtgcc ggagctggcc aaggcgtgca   2160
ccaccatcat ctggatcggg tcggcgctgc atgcggcagt caacttcggg cagtacccct   2220
acgcggggtt cctcccgaac cggccgacgg tgagccggcg ccgcatgccg gagcccggca   2280
cggaggagta cgcggagctg gagcgcgacc cggagcgggc cttcatccac accatcacga   2340
gccagatcca gaccatcatc ggcgtgtcgc tgctggaggt gctgtcgaag cactcctccg   2400
acgagctgta cctcgggcag cgggacacgc cggagtggac ctcggaccca aaggccctgg   2460
aggtgttcaa gcggttcagc gaccggctgg tggagatcga gagcaaggtg gtgggcatga   2520
accatgaccc ggagctcaag aaccgcaacg gcccggctaa gtttccctac atgctgctct   2580
accccaacac ctccgaccac aagggcgccg ctgccgggct taccgccaag gcatccccca   2640
acagcatctc catctaatct aagccatcgg caaccatgga tgaataaagg gcgttcgcca   2700
cgtacgaaac ttgtcgagag attggtgtag tgtgtgtctg tgacagtact atgtcagcag   2760
ttgctctttt agccgaataa ataaagcaga tttgcttcca aaaaaaaaaa aaaaaaaa    2818
```

<210> SEQ ID NO 11
<211> LENGTH: 4663
<212> TYPE: DNA
<213> ORGANISM: Hordeum vulgare
<220> FEATURE:
<221> NAME/KEY: variation
<222> LOCATION: (2346)..(2348)

-continued

<223> OTHER INFORMATION: "n" is a, c, t, or g encoding an acidic, basic, or polar amino aci

<400> SEQUENCE: 11

| | | | | | |
|---|---|---|---|---|---|
| cagccccatg | catgcacatg | cacatgcaca | tgcacatgca | gtgcagccaa | gcaccgctcg | 60 |
| atgggcgatc | acccgtcacg | ggaccggagc | gcgccatgcg | aagcacgagg | agggcacgtc | 120 |
| accgtccgcg | cgcagcacgt | ggagagcacg | tcgccgtccg | atccatctct | ccaaagccga | 180 |
| gcgccacacc | accgggaccg | gacccggacc | ggcctataaa | ttgcccggac | cgagctgcaa | 240 |
| gcagctcctc | acacacactc | acgcaacaca | catccatctt | cactgaaaag | tgaaaaacag | 300 |
| tgtgctggtg | ccattggttg | gagcagtgaa | agcgaggaga | ggaggccaag | aacaagatgc | 360 |
| tgctgggagg | gctgatcgac | accctcacgg | gggcgaacaa | gagcgcccgg | ctcaagggca | 420 |
| cggtggtgct | catgcgcaag | aacgtgctgg | acctcaacga | cttcggcgcc | accatcatcg | 480 |
| acggcatcg | cgagttcctc | ggcaagggtg | tcacctgcca | gcttatcagc | tccaccgccg | 540 |
| tcgaccaagg | taatcactac | cctcctccgg | ccttctcctc | tgtttacaag | atatagtatt | 600 |
| tctttcgtgt | gggccggcgg | ccatggatgg | atggatgtgt | ctggatcggc | taagaagat | 660 |
| aggatagcta | gccctggccg | tcgtctttta | cctgagcatg | ggcatatgcc | atcgaaaaaa | 720 |
| gagacaacag | catgcatgca | tggtgcgcgc | accagaccac | gcagagcacc | ggatgctcga | 780 |
| gacaaagcaa | cacaacaagc | aaggacgaca | cgtcaaaagc | aacacaacaa | gcaaggacgg | 840 |
| cacgtcaaaa | gcaacacaaa | cctaaactaa | agcacaaaga | cgtaagagca | agcacacaat | 900 |
| cagcaggcta | taaacagttg | tcatcaaaaa | caacgctgga | agagagagag | aaggaaggaa | 960 |
| gtagtagcca | tgaaaaatta | aatcaccggg | cgttgctctt | tgcccaacaa | ttaatcaagc | 1020 |
| agggtacgtg | gcatgtatag | ttcttgtaag | taaactaagc | atgtgatatg | agaaggtacg | 1080 |
| tggtggtgca | gacaacggcg | gtcgcgggaa | ggtgggcgcg | gaggcggagc | tggagcagtg | 1140 |
| ggtgacgagc | ctgccgtcgc | tgacgacggg | ggagtccaag | ttcggcctca | ccttcgactg | 1200 |
| ggaggtggag | aagctcgggg | tgccgggcgc | catcgtcgtc | aacaactacc | acagctccga | 1260 |
| gttcctgctt | aaaaccatca | ccctccacga | cgtccccggc | cgcagcggca | acctcacctt | 1320 |
| cgtcgccaac | tcatggatct | accccgccgc | caactaccga | tacagccgcg | tcttcttcgc | 1380 |
| caacgacgtg | cgtggatttt | cctctacttt | cctctccttt | cattttcacc | gccttcgtca | 1440 |
| ttcatggtcg | atcattaagt | cttgccagga | caatagatga | tgagctagga | gtggttacca | 1500 |
| cttagcagta | cgtacattat | ttattccgtg | ttggtagaaa | aggatatggt | ttggtgcaga | 1560 |
| tcgacacaag | attgaatgaa | agttgcaccg | tggcaccgtg | gcagcgtggt | aggtgaaaat | 1620 |
| aactgttgca | cggatccacc | cacatgattg | ttttcatgaa | taaactttt | aaggatgtgt | 1680 |
| ctagccacat | ctagatgcat | gtcacataat | tattgcatac | caaaacgatt | aaattaagca | 1740 |
| taaaagaaa | aggaaaaaa | tactcacata | tctcgacgta | agatcaatga | tatagtattt | 1800 |
| agatatgcaa | tatttatctt | acatctaaac | ctttcttcat | tcttaaatat | aagacatttg | 1860 |
| taagatttca | ctatggacaa | catacgaaac | aaaatcagtg | gatctctcta | tgcattcatt | 1920 |
| atgtagtcta | taataaaatc | tttaaaagat | cgtatatttt | gcaacggagg | gagtaaaaca | 1980 |
| taactttttta | atagtaatgt | tgcacggctc | cacactcgca | gacgtacctg | ccagccaga | 2040 |
| tgccggcggc | gctgaagccg | taccgcgacg | acgagctccg | gaacctgcgt | ggcgacgacc | 2100 |
| agcagggccc | gtaccaggag | cacgaccgca | tctaccgcta | cgacgtctac | aacgacctcg | 2160 |
| gcgagggccg | ccccatcctc | ggcggcaact | ccgaccaccc | ttacccgcgc | cgcggccgca | 2220 |

```
cggagcgcaa gcccaacgcc agcgacccga gcctggagag ccggctgtcg ctgctggagc    2280
agatctacgt gccgcgggac gagaagttcg gccacctcaa gacgtccgac ttcctgggct    2340
actccatcaa ggccatcacg cagggcatcc tgccggccgt cgcacctac gtggacacca     2400 cccccggcga gttcgactcc ttccaggaca tcatcaacct ctatgagggc ggcatcaagc    2460
tgcccaaggt ggccgccctg gaggagctcc gtaagcagtt cccgctccag ctcatcaagg    2520
acctcctccc cgtcggcggc gactccctgc ttaagctccc cgtgcccac atcatccagg     2580 agaacaagca ggcgtggagg accgacgagg agttcgcacg ggaggtgctc gccnnngtca    2640
acccggtcat gatcacgcgt ctcacggtga gtcagcgatt atttgttcat tgtgtgtgta    2700
tggtgtccat ggtgagaaag tgcagatctt gatttgcgtt gggtcgcatg cacgcatgct    2760
gcatgcatgc aggagttccc gccaaaaagt agtctggacc ctagcaagtt tggtgaccac    2820
accagcacca tcacggcgga gcacatagag aagaacctcg agggcctcac ggtgcagcag    2880
gtaattggtc caagccatcg acatcaacta tgatttacct aggagtaatt ggtagctgta    2940
gataatttgg cttcgttgca attaatttga tgctggccga tcaagtgatc gtattgggtt    3000
tgaaatttgc aggcgctgga agcaacagg ctgtacatcc ttgatcacca tgaccggttc     3060
atgccgttcc tgatcgacgt caacaacctg cccggcaact tcatctacgc cacgaggacc    3120
ctcttcttcc tgcgcggcga cggcaggctc acgccgctcg ccatcgagct gagcgagccc    3180
atcatccagg gcggccttac cacggccaag agcaaggttt acacgccggt gcccagcggc    3240
tccgtcgaag gctgggtgtg ggagctcgcc aaggcctacg tcgccgtcaa tgactccggg    3300
tggcaccagc tcgtcagcca ctggtacgtt ctccacggtc gatgtgattc agtcagtcga    3360
tgcacaacaa ctgatcgaaa tatgattgat tgaaacgcgc aggctgaaca ctcacgcggt    3420
gatggagccg ttcgtgatct cgacgaaccg gcaccttagc gtgacgcacc cggtgcacaa    3480
gctgctgagc ccgcactacc gcgacaccat gaccatcaac gcgctggcgc ggcagacgct    3540
catcaacgcc ggcggcatct tcgagatgac ggtgttcccg ggcaagttcg cgttggggat    3600
gtcggccgtg tgtacaagg actggaagtt caccgagcag ggactgccgg acgatctcat     3660
caagaggtac gtacctggta aatgttatga atgtgtaaaa caaattgggc gtctcgctca    3720
ctgacaggaa cgtggtaaaa aaaatgcagg ggcatggcgg tggaggaccc gtcgagcccg    3780
tacaaggtgc ggttgctggt gtcggactac ccgtacgcgg cggacgggct ggcgatctgg    3840
cacgccattg agcagtacgt gagcgagtac ctggccatct actacccgaa cgacggcgtg    3900
ctgcagggcg atacggaggt gcaggcgtgg tggaaggaga cgcgcgaggt cgggcacggc    3960
gacctcaagg acgcccatg gtggcccaag atgcaaagtg tgccggagct ggccaaggcg    4020
tgcaccacca tcatctggat cgggtcggcg ctgcatgcgg cagtcaactt cgggcagtac    4080
ccctacgcgg ggttcctccc gaaccggccg acggtgagcc ggcgccgcat gccggagccc    4140
ggcacggagg agtacgcgga gctggagcgc gacccggagc gggccttcat ccacaccatc    4200
acgagccaga tccagaccat catcggcgtg tcgctgctgg aggtgctgtc gaagcactcc    4260
tccgacgagc tgtacctcgg gcagcgggac acgccggagt ggacctcgga cccaaaggcc    4320
ctggaggtgt tcaagcggtt cagcgaccgg ctggtggaga tcgagagcaa ggtggtgggc    4380
atgaaccatg acccggagct caagaaccgc aacggcccgg ctaagtttcc ctacatgctg    4440
ctctacccca cacctccga ccacaagggc ccgctgccg gcttaccgc caagggcatc       4500 cccaacagca tctccatcta atctaagcca tcggcaacca tggatgaata aagggcgttc    4560
gccacgtacg aaacttgtcg agagattggt gtagtgtgtg tctgtgacag tactatgtca    4620
```

```
gcagttgctc tttaagccga ataaataaag cagatttgct tcc                    4663
```

<210> SEQ ID NO 12
<211> LENGTH: 862
<212> TYPE: PRT
<213> ORGANISM: Hordeum vulgare
<220> FEATURE:
<221> NAME/KEY: variation
<222> LOCATION: (368)..(368)
<223> OTHER INFORMATION: "Xaa" is an acidic, basic, or polar amino acid

<400> SEQUENCE: 12

```
Met Leu Leu Gly Gly Leu Ile Asp Thr Leu Thr Gly Ala Asn Lys Ser
1               5                   10                  15

Ala Arg Leu Lys Gly Thr Val Val Leu Met Arg Lys Asn Val Leu Asp
            20                  25                  30

Leu Asn Asp Phe Gly Ala Thr Ile Ile Asp Gly Ile Gly Glu Phe Leu
        35                  40                  45

Gly Lys Gly Val Thr Cys Gln Leu Ile Ser Ser Thr Ala Val Asp Gln
    50                  55                  60

Asp Asn Gly Gly Arg Gly Lys Val Gly Ala Glu Ala Leu Glu Gln
65                  70                  75                  80

Trp Val Thr Ser Leu Pro Ser Leu Thr Thr Gly Glu Ser Lys Phe Gly
                85                  90                  95

Leu Thr Phe Asp Trp Glu Val Glu Lys Leu Gly Val Pro Gly Ala Ile
            100                 105                 110

Val Val Asn Asn Tyr His Ser Ser Glu Phe Leu Leu Lys Thr Ile Thr
        115                 120                 125

Leu His Asp Val Pro Gly Arg Ser Gly Asn Leu Thr Phe Val Ala Asn
    130                 135                 140

Ser Trp Ile Tyr Pro Ala Ala Asn Tyr Arg Tyr Ser Arg Val Phe Phe
145                 150                 155                 160

Ala Asn Asp Thr Tyr Leu Pro Ser Gln Met Pro Ala Ala Leu Lys Pro
                165                 170                 175

Tyr Arg Asp Asp Glu Leu Arg Asn Leu Arg Gly Asp Asp Gln Gln Gly
            180                 185                 190

Pro Tyr Gln Glu His Asp Arg Ile Tyr Arg Tyr Asp Val Tyr Asn Asp
        195                 200                 205

Leu Gly Glu Gly Arg Pro Ile Leu Gly Gly Asn Ser Asp His Pro Tyr
    210                 215                 220

Pro Arg Arg Gly Arg Thr Glu Arg Lys Pro Asn Ala Ser Asp Pro Ser
225                 230                 235                 240

Leu Glu Ser Arg Leu Ser Leu Glu Gln Ile Tyr Val Pro Arg Asp
                245                 250                 255

Glu Lys Phe Gly His Leu Lys Thr Ser Asp Phe Leu Gly Tyr Ser Ile
            260                 265                 270

Lys Ala Ile Thr Gln Gly Ile Leu Pro Ala Val Arg Thr Tyr Val Asp
        275                 280                 285

Thr Thr Pro Gly Glu Phe Asp Ser Phe Gln Asp Ile Ile Asn Leu Tyr
    290                 295                 300

Glu Gly Gly Ile Lys Leu Pro Lys Val Ala Ala Leu Glu Glu Leu Arg
305                 310                 315                 320

Lys Gln Phe Pro Leu Gln Leu Ile Lys Asp Leu Leu Pro Val Gly Gly
                325                 330                 335

Asp Ser Leu Leu Lys Leu Pro Val Pro His Ile Ile Gln Glu Asn Lys
```

-continued

```
                340                 345                 350
Gln Ala Trp Arg Thr Asp Glu Glu Phe Ala Arg Glu Val Leu Ala Xaa
            355                 360                 365
Val Asn Pro Val Met Ile Thr Arg Leu Thr Glu Phe Pro Pro Lys Ser
        370                 375                 380
Ser Leu Asp Pro Ser Lys Phe Gly Asp His Thr Ser Thr Ile Thr Ala
385                 390                 395                 400
Glu His Ile Glu Lys Asn Leu Glu Gly Leu Thr Val Gln Gln Ala Leu
                405                 410                 415
Glu Ser Asn Arg Leu Tyr Ile Leu Asp His His Asp Arg Phe Met Pro
            420                 425                 430
Phe Leu Ile Asp Val Asn Asn Leu Pro Gly Asn Phe Ile Tyr Ala Thr
        435                 440                 445
Arg Thr Leu Phe Phe Leu Arg Gly Asp Gly Arg Leu Thr Pro Leu Ala
    450                 455                 460
Ile Glu Leu Ser Glu Pro Ile Ile Gln Gly Gly Leu Thr Thr Ala Lys
465                 470                 475                 480
Ser Lys Val Tyr Thr Pro Val Pro Ser Gly Ser Val Glu Gly Trp Val
                485                 490                 495
Trp Glu Leu Ala Lys Ala Tyr Val Ala Val Asn Asp Ser Gly Trp His
            500                 505                 510
Gln Leu Val Ser His Trp Leu Asn Thr His Ala Val Met Glu Pro Phe
        515                 520                 525
Val Ile Ser Thr Asn Arg His Leu Ser Val Thr His Pro Val His Lys
    530                 535                 540
Leu Leu Ser Pro His Tyr Arg Asp Thr Met Thr Ile Asn Ala Leu Ala
545                 550                 555                 560
Arg Gln Thr Leu Ile Asn Ala Gly Gly Ile Phe Glu Met Thr Val Phe
                565                 570                 575
Pro Gly Lys Phe Ala Leu Gly Met Ser Ala Val Val Tyr Lys Asp Trp
            580                 585                 590
Lys Phe Thr Glu Gln Gly Leu Pro Asp Asp Leu Ile Lys Arg Gly Met
        595                 600                 605
Ala Val Glu Asp Pro Ser Ser Pro Tyr Lys Val Arg Leu Leu Val Ser
    610                 615                 620
Asp Tyr Pro Tyr Ala Ala Asp Gly Leu Ala Ile Trp His Ala Ile Glu
625                 630                 635                 640
Gln Tyr Val Ser Glu Tyr Leu Ala Ile Tyr Tyr Pro Asn Asp Gly Val
                645                 650                 655
Leu Gln Gly Asp Thr Glu Val Gln Ala Trp Trp Lys Glu Thr Arg Glu
            660                 665                 670
Val Gly His Gly Asp Leu Lys Asp Ala Pro Trp Trp Pro Lys Met Gln
        675                 680                 685
Ser Val Pro Glu Leu Ala Lys Ala Cys Thr Thr Ile Ile Trp Ile Gly
    690                 695                 700
Ser Ala Leu His Ala Ala Val Asn Phe Gly Gln Tyr Pro Tyr Ala Gly
705                 710                 715                 720
Phe Leu Pro Asn Arg Pro Thr Val Ser Arg Arg Met Pro Glu Pro
                725                 730                 735
Gly Thr Glu Glu Tyr Ala Glu Leu Glu Arg Asp Pro Glu Arg Ala Phe
            740                 745                 750
Ile His Thr Ile Thr Ser Gln Ile Gln Thr Ile Ile Gly Val Ser Leu
        755                 760                 765
```

```
Leu Glu Val Leu Ser Lys His Ser Ser Asp Glu Leu Tyr Leu Gly Gln
    770                 775                 780

Arg Asp Thr Pro Glu Trp Thr Ser Asp Pro Lys Ala Leu Glu Val Phe
785                 790                 795                 800

Lys Arg Phe Ser Asp Arg Leu Val Glu Ile Glu Ser Lys Val Val Gly
                805                 810                 815

Met Asn His Asp Pro Glu Leu Lys Asn Arg Asn Gly Pro Ala Lys Phe
            820                 825                 830

Pro Tyr Met Leu Leu Tyr Pro Asn Thr Ser Asp His Lys Gly Ala Ala
        835                 840                 845

Ala Gly Leu Thr Ala Lys Gly Ile Pro Asn Ser Ile Ser Ile
    850                 855                 860

<210> SEQ ID NO 13
<211> LENGTH: 20
<212> TYPE: DNA
<213> ORGANISM: Hordeum vulgare

<400> SEQUENCE: 13
cgctacgacg tctacaacga                                                      20

<210> SEQ ID NO 14
<211> LENGTH: 20
<212> TYPE: DNA
<213> ORGANISM: Hordeum vulgare

<400> SEQUENCE: 14
cagactactt tttggcggga                                                      20

<210> SEQ ID NO 15
<211> LENGTH: 839
<212> TYPE: PRT
<213> ORGANISM: Glycine max

<400> SEQUENCE: 15

Met Phe Ser Ala Gly His Lys Ile Lys Gly Thr Val Val Leu Met Pro
1               5                   10                  15

Lys Asn Glu Leu Glu Val Asn Pro Asp Gly Ser Ala Val Asp Asn Leu
            20                  25                  30

Asn Ala Phe Leu Gly Arg Ser Val Ser Leu Gln Leu Ile Ser Ala Thr
        35                  40                  45

Lys Ala Asp Ala His Gly Lys Gly Lys Val Gly Lys Asp Thr Phe Leu
    50                  55                  60

Glu Gly Ile Asn Thr Ser Leu Pro Thr Leu Gly Ala Gly Glu Ser Ala
65                  70                  75                  80

Phe Asn Ile His Phe Glu Trp Asp Gly Ser Met Gly Ile Pro Gly Ala
                85                  90                  95

Phe Tyr Ile Lys Asn Tyr Met Gln Val Glu Phe Phe Leu Lys Ser Leu
            100                 105                 110

Thr Leu Glu Ala Ile Ser Asn Gln Gly Thr Ile Arg Phe Val Cys Asn
        115                 120                 125

Ser Trp Val Tyr Asn Thr Lys Leu Tyr Lys Ser Val Arg Ile Phe Phe
    130                 135                 140

Ala Asn His Thr Tyr Val Pro Ser Glu Thr Pro Ala Pro Leu Val Ser
145                 150                 155                 160

Tyr Arg Glu Glu Glu Leu Lys Ser Leu Arg Gly Asn Gly Thr Gly Glu
                165                 170                 175
```

```
Arg Lys Glu Tyr Asp Arg Ile Tyr Asp Tyr Asp Val Tyr Asn Asp Leu
            180                 185                 190
Gly Asn Pro Asp Lys Ser Glu Lys Leu Ala Arg Pro Val Leu Gly Gly
            195                 200                 205
Ser Ser Thr Phe Pro Tyr Pro Arg Arg Gly Arg Thr Gly Arg Gly Pro
210                 215                 220
Thr Val Thr Asp Pro Asn Thr Glu Lys Gln Gly Glu Val Phe Tyr Val
225                 230                 235                 240
Pro Arg Asp Glu Asn Leu Gly His Leu Lys Ser Lys Asp Ala Leu Glu
            245                 250                 255
Ile Gly Thr Lys Ser Leu Ser Gln Ile Val Gln Pro Ala Phe Glu Ser
            260                 265                 270
Ala Phe Asp Leu Lys Ser Thr Pro Ile Glu Phe His Ser Phe Gln Asp
            275                 280                 285
Val His Asp Leu Tyr Glu Gly Gly Ile Lys Leu Pro Arg Asp Val Ile
            290                 295                 300
Ser Thr Ile Ile Pro Leu Pro Val Ile Lys Glu Leu Tyr Arg Thr Asp
305                 310                 315                 320
Gly Gln His Ile Leu Lys Phe Pro Gln Pro His Val Val Gln Val Ser
            325                 330                 335
Gln Ser Ala Trp Met Thr Asp Glu Glu Phe Ala Arg Glu Met Ile Ala
            340                 345                 350
Gly Val Asn Pro Cys Val Ile Arg Gly Leu Glu Phe Pro Pro Lys
            355                 360                 365
Ser Asn Leu Asp Pro Ala Ile Tyr Gly Asp Gln Ser Ser Lys Ile Thr
            370                 375                 380
Ala Asp Ser Leu Asp Leu Asp Gly Tyr Thr Met Asp Glu Ala Leu Gly
385                 390                 395                 400
Ser Arg Arg Leu Phe Met Leu Asp Tyr His Asp Ile Phe Met Pro Tyr
            405                 410                 415
Val Arg Gln Ile Asn Gln Leu Asn Ser Ala Lys Thr Tyr Ala Thr Arg
            420                 425                 430
Thr Ile Leu Phe Leu Arg Glu Asp Gly Thr Leu Lys Pro Val Ala Ile
            435                 440                 445
Glu Leu Ser Leu Pro His Ser Ala Gly Asp Leu Ser Ala Ala Val Ser
450                 455                 460
Gln Val Val Leu Pro Ala Lys Glu Gly Val Glu Ser Thr Ile Trp Leu
465                 470                 475                 480
Leu Ala Lys Ala Tyr Val Ile Val Asn Asp Ser Cys Tyr His Gln Leu
            485                 490                 495
Met Ser His Trp Leu Asn Thr His Ala Ala Met Glu Pro Phe Val Ile
            500                 505                 510
Ala Thr His Arg His Leu Ser Val Leu His Pro Ile Tyr Lys Leu Leu
            515                 520                 525
Thr Pro His Tyr Arg Asn Asn Met Asn Ile Asn Ala Leu Ala Arg Gln
            530                 535                 540
Ser Leu Ile Asn Ala Asn Gly Ile Ile Glu Thr Thr Phe Leu Pro Ser
545                 550                 555                 560
Lys Tyr Ser Val Glu Met Ser Ser Ala Val Tyr Lys Asn Trp Val Phe
            565                 570                 575
Thr Asp Gln Ala Leu Pro Ala Asp Leu Ile Lys Arg Gly Val Ala Ile
            580                 585                 590
```

-continued

Lys Asp Pro Ser Thr Pro His Gly Val Arg Leu Leu Ile Glu Asp Tyr
            595                 600                 605

Pro Tyr Ala Ala Asp Gly Leu Glu Ile Trp Ala Ala Ile Lys Thr Trp
        610                 615                 620

Val Gln Glu Tyr Val Pro Leu Tyr Tyr Ala Arg Asp Asp Val Lys
625                 630                 635                 640

Asn Asp Ser Glu Leu Gln His Trp Trp Lys Glu Ala Val Glu Lys Gly
            645                 650                 655

His Gly Asp Leu Lys Asp Lys Pro Trp Trp Pro Lys Leu Gln Thr Leu
            660                 665                 670

Glu Asp Leu Val Glu Val Cys Leu Ile Ile Ile Trp Ile Ala Ser Ala
        675                 680                 685

Leu His Ala Ala Val Asn Phe Gly Gln Tyr Pro Tyr Gly Gly Leu Ile
        690                 695                 700

Met Asn Arg Pro Thr Ala Ser Arg Arg Leu Leu Pro Glu Lys Gly Thr
705                 710                 715                 720

Pro Glu Tyr Glu Glu Met Ile Asn Asn His Glu Lys Ala Tyr Leu Arg
            725                 730                 735

Thr Ile Thr Ser Lys Leu Pro Thr Leu Ile Ser Leu Ser Val Ile Glu
        740                 745                 750

Ile Leu Ser Thr His Ala Ser Asp Glu Val Tyr Leu Gly Gln Arg Asp
        755                 760                 765

Asn Pro His Trp Thr Ser Asp Ser Lys Ala Leu Gln Ala Phe Gln Lys
770                 775                 780

Phe Gly Asn Lys Leu Lys Glu Ile Glu Glu Lys Leu Val Arg Arg Asn
785                 790                 795                 800

Asn Asp Pro Ser Leu Gln Gly Asn Arg Leu Gly Pro Val Gln Leu Pro
            805                 810                 815

Tyr Thr Leu Leu Tyr Pro Ser Ser Glu Glu Gly Leu Thr Phe Arg Gly
        820                 825                 830

Ile Pro Asn Ser Ile Ser Ile
        835

<210> SEQ ID NO 16
<211> LENGTH: 865
<212> TYPE: PRT
<213> ORGANISM: Glycine max

<400> SEQUENCE: 16

Met Phe Ser Val Pro Gly Val Ser Gly Ile Leu Asn Arg Gly Gly Gly
1               5                   10                  15

His Lys Ile Lys Gly Thr Val Val Leu Met Arg Lys Asn Val Leu Asp
            20                  25                  30

Phe Asn Ser Val Ala Asp Leu Thr Lys Gly Asn Val Gly Gly Leu Ile
        35                  40                  45

Gly Thr Gly Leu Asn Val Val Gly Ser Thr Leu Asp Asn Leu Thr Ala
    50                  55                  60

Phe Leu Gly Arg Ser Val Ala Leu Gln Leu Ile Ser Ala Thr Lys Pro
65                  70                  75                  80

Leu Ala Asn Gly Lys Gly Lys Val Gly Lys Asp Thr Phe Leu Glu Gly
            85                  90                  95

Ile Ile Val Ser Leu Pro Thr Leu Gly Ala Gly Glu Ser Ala Phe Asn
            100                 105                 110

Ile Gln Phe Glu Trp Asp Glu Ser Met Gly Ile Pro Gly Ala Phe Tyr
        115                 120                 125

-continued

```
Ile Lys Asn Tyr Met Gln Val Glu Phe Tyr Leu Lys Ser Leu Thr Leu
    130                 135                 140
Glu Asp Val Pro Asn Gln Gly Thr Ile Arg Phe Val Cys Asn Ser Trp
145                 150                 155                 160
Val Tyr Asn Thr Lys Leu Tyr Lys Ser Val Arg Ile Phe Phe Ala Asn
                165                 170                 175
His Thr Tyr Val Pro Ser Glu Thr Pro Ala Ala Leu Val Gly Tyr Arg
                180                 185                 190
Glu Glu Glu Leu Lys Asn Leu Arg Gly Asp Gly Lys Gly Glu Arg Lys
                195                 200                 205
Glu His Asp Arg Ile Tyr Asp Tyr Asp Val Tyr Asn Asp Leu Gly Asn
    210                 215                 220
Pro Asp His Gly Glu Asn Phe Ala Arg Pro Ile Leu Gly Gly Ser Ser
225                 230                 235                 240
Thr His Pro Tyr Pro Arg Arg Gly Arg Thr Gly Arg Tyr Pro Thr Arg
                245                 250                 255
Lys Asp Gln Asn Ser Glu Lys Pro Gly Glu Val Tyr Val Pro Arg Asp
                260                 265                 270
Glu Asn Phe Gly His Leu Lys Ser Ser Asp Phe Leu Ala Tyr Gly Ile
                275                 280                 285
Lys Ser Leu Ser Gln Tyr Val Leu Pro Ala Phe Glu Ser Val Phe Asp
    290                 295                 300
Leu Asn Phe Thr Pro Asn Glu Phe Asp Ser Phe Gln Asp Val Arg Asp
305                 310                 315                 320
Leu His Glu Gly Gly Ile Lys Leu Pro Thr Glu Val Ile Ser Thr Ile
                325                 330                 335
Met Pro Leu Pro Val Val Lys Glu Leu Phe Arg Thr Asp Gly Glu Gln
                340                 345                 350
Val Leu Lys Phe Pro Pro His Val Ile Gln Val Ser Lys Ser Ala
                355                 360                 365
Trp Met Thr Asp Glu Glu Phe Ala Arg Glu Met Val Ala Gly Val Asn
    370                 375                 380
Pro Cys Val Ile Arg Gly Leu Gln Glu Phe Pro Pro Lys Ser Asn Leu
385                 390                 395                 400
Asp Pro Thr Ile Tyr Gly Glu Gln Thr Ser Lys Ile Thr Ala Asp Ala
                405                 410                 415
Leu Asp Leu Asp Gly Tyr Thr Val Asp Glu Ala Leu Ala Ser Arg Arg
                420                 425                 430
Leu Phe Met Leu Asp Tyr His Asp Val Phe Met Pro Tyr Ile Arg Arg
                435                 440                 445
Ile Asn Gln Thr Tyr Ala Lys Ala Tyr Ala Thr Arg Thr Ile Leu Phe
    450                 455                 460
Leu Arg Glu Asn Gly Thr Leu Lys Pro Val Ala Ile Glu Leu Ser Leu
465                 470                 475                 480
Pro His Pro Ala Gly Asp Leu Ser Gly Ala Val Ser Gln Val Ile Leu
                485                 490                 495
Pro Ala Lys Glu Gly Val Glu Ser Thr Ile Trp Leu Leu Ala Lys Ala
                500                 505                 510
Tyr Val Val Asn Asp Ser Cys Tyr His Gln Leu Met Ser His Trp
                515                 520                 525
Leu Asn Thr His Ala Val Ile Glu Pro Phe Ile Ile Ala Thr Asn Arg
    530                 535                 540
```

-continued

```
His Leu Ser Ala Leu His Pro Ile Tyr Lys Leu Leu Thr Pro His Tyr
545                 550                 555                 560

Arg Asp Thr Met Asn Ile Asn Ala Leu Ala Arg Gln Ser Leu Ile Asn
                565                 570                 575

Ala Asp Gly Ile Ile Glu Lys Ser Phe Leu Pro Ser Lys His Ser Val
            580                 585                 590

Glu Met Ser Ser Ala Val Tyr Lys Asn Trp Val Phe Thr Asp Gln Ala
        595                 600                 605

Leu Pro Ala Asp Leu Ile Lys Arg Gly Val Ala Ile Lys Asp Pro Ser
    610                 615                 620

Ala Pro His Gly Leu Arg Leu Leu Ile Glu Asp Tyr Pro Tyr Ala Val
625                 630                 635                 640

Asp Gly Leu Glu Ile Trp Ala Ala Ile Lys Thr Trp Val Gln Glu Tyr
                645                 650                 655

Val Ser Leu Tyr Tyr Ala Arg Asp Asp Val Lys Pro Asp Ser Glu
                660                 665                 670

Leu Gln Gln Trp Trp Lys Glu Ala Val Glu Lys Gly His Gly Asp Leu
        675                 680                 685

Lys Asp Lys Pro Trp Trp Pro Lys Leu Gln Thr Ile Glu Glu Leu Val
    690                 695                 700

Glu Ile Cys Thr Ile Ile Trp Thr Ala Ser Ala Leu His Ala Ala
705                 710                 715                 720

Val Asn Phe Gly Gln Tyr Pro Tyr Gly Gly Phe Ile Leu Asn Arg Pro
                725                 730                 735

Thr Ser Ser Arg Arg Leu Leu Pro Glu Lys Gly Thr Pro Glu Tyr Glu
            740                 745                 750

Glu Met Val Lys Ser His Gln Lys Ala Tyr Leu Arg Thr Ile Thr Ser
        755                 760                 765

Lys Phe Gln Thr Leu Val Asp Leu Ser Val Ile Glu Ile Leu Ser Arg
    770                 775                 780

His Ala Ser Asp Glu Val Tyr Leu Gly Gln Arg Asp Asn Pro His Trp
785                 790                 795                 800

Thr Ser Asp Ser Lys Ala Leu Gln Ala Phe Gln Lys Phe Gly Asn Lys
                805                 810                 815

Leu Lys Glu Ile Glu Glu Lys Leu Ala Arg Lys Asn Asn Asp Gln Ser
            820                 825                 830

Leu Ser Asn Arg Leu Gly Pro Val Gln Leu Pro Tyr Thr Leu Leu His
        835                 840                 845

Pro Asn Ser Glu Gly Leu Thr Cys Arg Gly Ile Pro Asn Ser Ile Ser
    850                 855                 860

Ile
865

<210> SEQ ID NO 17
<211> LENGTH: 857
<212> TYPE: PRT
<213> ORGANISM: Glycine max

<400> SEQUENCE: 17

Met Leu Gly Gly Leu Leu His Arg Gly His Lys Ile Lys Gly Thr Val
1               5                   10                  15

Val Leu Met Arg Lys Asn Val Leu Asp Val Asn Ser Val Thr Ser Val
                20                  25                  30

Gly Gly Ile Ile Gly Gln Gly Leu Asp Leu Val Gly Ser Thr Leu Asp
            35                  40                  45
```

-continued

```
Thr Leu Thr Ala Phe Leu Gly Arg Ser Val Ser Leu Gln Leu Ile Ser
 50                  55                  60

Ala Thr Lys Ala Asp Ala Asn Gly Lys Gly Lys Leu Gly Lys Ala Thr
 65                  70                  75                  80

Phe Leu Glu Gly Ile Ile Thr Ser Leu Pro Thr Leu Gly Ala Gly Gln
                 85                  90                  95

Ser Ala Phe Lys Ile Asn Phe Glu Trp Asp Asp Gly Ser Gly Ile Pro
                100                 105                 110

Gly Ala Phe Tyr Ile Lys Asn Phe Met Gln Thr Glu Phe Phe Leu Val
                115                 120                 125

Ser Leu Thr Leu Glu Asp Ile Pro Asn His Gly Ser Ile His Phe Val
130                 135                 140

Cys Asn Ser Trp Ile Tyr Asn Ala Lys Leu Phe Lys Ser Asp Arg Ile
145                 150                 155                 160

Phe Phe Ala Asn Gln Thr Tyr Leu Pro Ser Glu Thr Pro Ala Pro Leu
                165                 170                 175

Val Lys Tyr Arg Glu Glu Glu Leu His Asn Leu Arg Gly Asp Gly Thr
                180                 185                 190

Gly Glu Arg Lys Glu Trp Glu Arg Ile Tyr Asp Tyr Asp Val Tyr Asn
                195                 200                 205

Asp Leu Gly Asp Pro Asp Lys Gly Glu Asn His Ala Arg Pro Val Leu
210                 215                 220

Gly Gly Asn Asp Thr Phe Pro Tyr Pro Arg Arg Gly Arg Thr Gly Arg
225                 230                 235                 240

Lys Pro Thr Arg Lys Asp Pro Asn Ser Glu Ser Arg Ser Asn Asp Val
                245                 250                 255

Tyr Leu Pro Arg Asp Glu Ala Phe Gly His Leu Lys Ser Ser Asp Phe
                260                 265                 270

Leu Thr Tyr Gly Leu Lys Ser Val Ser Gln Asn Val Leu Pro Leu Leu
                275                 280                 285

Gln Ser Ala Phe Asp Leu Asn Phe Thr Pro Arg Glu Phe Asp Ser Phe
290                 295                 300

Asp Glu Val His Gly Leu Tyr Ser Gly Gly Ile Lys Leu Pro Thr Asp
305                 310                 315                 320

Ile Ile Ser Lys Ile Ser Pro Leu Pro Val Leu Lys Glu Ile Phe Arg
                325                 330                 335

Thr Asp Gly Glu Gln Ala Leu Lys Phe Pro Pro Lys Val Ile Gln
                340                 345                 350

Val Ser Lys Ser Ala Trp Met Thr Asp Glu Glu Phe Ala Arg Glu Met
                355                 360                 365

Leu Ala Gly Val Asn Pro Asn Leu Ile Arg Cys Leu Lys Asp Phe Pro
370                 375                 380

Pro Arg Ser Lys Leu Asp Ser Gln Val Tyr Gly Asp His Thr Ser Gln
385                 390                 395                 400

Ile Thr Lys Glu His Leu Glu Pro Asn Leu Glu Gly Leu Thr Val Asp
                405                 410                 415

Glu Ala Ile Gln Asn Lys Arg Leu Phe Leu Leu Asp His His Asp Pro
                420                 425                 430

Ile Met Pro Tyr Leu Arg Arg Ile Asn Ala Thr Ser Thr Lys Ala Tyr
                435                 440                 445

Ala Thr Arg Thr Ile Leu Phe Leu Lys Asn Asp Gly Thr Leu Arg Pro
450                 455                 460
```

```
Leu Ala Ile Glu Leu Ser Leu Pro His Pro Gln Gly Asp Gln Ser Gly
465                 470                 475                 480

Ala Phe Ser Gln Val Phe Leu Pro Ala Asp Glu Gly Val Glu Ser Ser
            485                 490                 495

Ile Trp Leu Leu Ala Lys Ala Tyr Val Val Asn Asp Ser Cys Tyr
                500                 505                 510

His Gln Leu Val Ser His Trp Leu Asn Thr His Ala Val Val Glu Pro
            515                 520                 525

Phe Ile Ile Ala Thr Asn Arg His Leu Ser Val His Pro Ile Tyr
530                 535                 540

Lys Leu Leu His Pro His Tyr Arg Asp Thr Met Asn Ile Asn Gly Leu
545                 550                 555                 560

Ala Arg Leu Ser Leu Val Asn Asp Gly Gly Val Ile Glu Gln Thr Phe
                565                 570                 575

Leu Trp Gly Arg Tyr Ser Val Glu Met Ser Ala Val Val Tyr Lys Asp
            580                 585                 590

Trp Val Phe Thr Asp Gln Ala Leu Pro Ala Asp Leu Ile Lys Arg Gly
            595                 600                 605

Met Ala Ile Glu Asp Pro Ser Cys Pro His Gly Ile Arg Leu Val Ile
610                 615                 620

Glu Asp Tyr Pro Tyr Thr Val Asp Gly Leu Glu Ile Trp Asp Ala Ile
625                 630                 635                 640

Lys Thr Trp Val His Glu Tyr Val Phe Leu Tyr Tyr Lys Ser Asp Asp
                645                 650                 655

Thr Leu Arg Glu Asp Pro Glu Leu Gln Ala Cys Trp Lys Glu Leu Val
            660                 665                 670

Glu Val Gly His Gly Asp Lys Lys Asn Glu Pro Trp Trp Pro Lys Met
            675                 680                 685

Gln Thr Arg Glu Glu Leu Val Glu Ala Cys Ala Ile Ile Ile Trp Thr
            690                 695                 700

Ala Ser Ala Leu His Ala Ala Val Asn Phe Gly Gln Tyr Pro Tyr Gly
705                 710                 715                 720

Gly Leu Ile Leu Asn Arg Pro Thr Leu Ser Arg Arg Phe Met Pro Glu
                725                 730                 735

Lys Gly Ser Ala Glu Tyr Glu Glu Leu Arg Lys Asn Pro Gln Lys Ala
            740                 745                 750

Tyr Leu Lys Thr Ile Thr Pro Lys Phe Gln Thr Leu Ile Asp Leu Ser
            755                 760                 765

Val Ile Glu Ile Leu Ser Arg His Ala Ser Asp Glu Val Tyr Leu Gly
770                 775                 780

Glu Arg Asp Asn Pro Asn Trp Thr Ser Asp Thr Arg Ala Leu Glu Ala
785                 790                 795                 800

Phe Lys Arg Phe Gly Asn Lys Leu Ala Gln Ile Glu Asn Lys Leu Ser
                805                 810                 815

Glu Arg Asn Asn Asp Glu Lys Leu Arg Asn Arg Cys Gly Pro Val Gln
            820                 825                 830

Met Pro Tyr Thr Leu Leu Leu Pro Ser Ser Lys Glu Gly Leu Thr Phe
            835                 840                 845

Arg Gly Ile Pro Asn Ser Ile Ser Ile
            850                 855

<210> SEQ ID NO 18
<211> LENGTH: 864
<212> TYPE: PRT
```

<213> ORGANISM: Hordeum vulgare

<400> SEQUENCE: 18

Met Leu Gly Val Gly Gly Ile Val Ser Asp Leu Thr Gly Gly Ile Arg
1               5                   10                  15

Gly Ala His Leu Lys Gly Ser Val Val Leu Met Arg Lys Asn Ala Leu
            20                  25                  30

Asp Phe Asn Asp Phe Gly Ala His Val Met Asp Gly Val Thr Glu Leu
        35                  40                  45

Leu Gly Arg Gly Val Thr Cys Gln Leu Ile Ser Thr Asn Val Asp
    50                  55                  60

His Asn Asn Gly Gly Arg Gly Lys Val Gly Ala Glu Ala Asn Leu Glu
65                  70                  75                  80

Gln Trp Leu Leu Pro Thr Asn Leu Pro Phe Ile Thr Thr Gly Glu Asn
                85                  90                  95

Lys Phe Ala Val Thr Phe Asp Trp Ser Val Asp Lys Leu Gly Val Pro
            100                 105                 110

Gly Ala Ile Ile Val Lys Asn Asn His Ala Ser Glu Phe Phe Leu Lys
        115                 120                 125

Thr Ile Thr Leu Asp Asn Val Pro Gly Arg Gly Thr Ile Val Phe Val
    130                 135                 140

Ala Asn Ser Trp Val Tyr Pro Gln Ala Lys Tyr Arg Tyr Asn Arg Val
145                 150                 155                 160

Phe Phe Ala Asn Asp Thr Tyr Leu Pro His Gln Met Pro Ala Ala Leu
                165                 170                 175

Lys Pro Tyr Arg Asp Asp Glu Leu Arg Asn Leu Arg Gly Asp Asp Gln
            180                 185                 190

Gln Gly Pro Tyr Leu Asp His Asp Arg Val Tyr Arg Tyr Asp Val Tyr
        195                 200                 205

Asn Asp Leu Gly Asp Ser Arg Asp Val Leu Gly Gly Ser Lys Asp Leu
    210                 215                 220

Pro Tyr Pro Arg Arg Cys Arg Thr Gly Arg Lys Pro Ser Asp Ser Lys
225                 230                 235                 240

Pro Asp His Glu Ser Arg Leu Leu Leu Val Gln Asn Val Tyr Val
                245                 250                 255

Leu Arg Asp Glu Leu Phe Gly His Leu Lys Gln Ser Asp Leu Leu Gly
            260                 265                 270

Tyr Thr Leu Lys Gly Trp Leu Asp Gly Ile Ile Leu Ala Ile Arg Thr
        275                 280                 285

Tyr Val Asp Leu Ser Pro Gly Glu Phe Asp Ser Phe Ala Asp Ile Leu
    290                 295                 300

Lys Leu Tyr Glu Gly Gly Ile Lys Leu Pro Asn Ile Pro Ala Leu Glu
305                 310                 315                 320

Glu Val Arg Lys Arg Phe Pro Leu Gln Leu Val Lys Asp Leu Ile Pro
                325                 330                 335

Lys Gly Gly Asp Phe Leu Leu Leu Pro Lys Pro Glu Ile Ile Lys
            340                 345                 350

Val Asp Gln Lys Ala Trp Met Thr Asp Glu Glu Phe Ala Arg Glu Met
        355                 360                 365

Leu Ala Gly Val Asn Pro Met Met Ile Lys Arg Leu Thr Glu Phe Pro
    370                 375                 380

Pro Lys Ser Thr Leu Asp Pro Ser Lys Tyr Gly Asp His Thr Ser Thr
385                 390                 395                 400

-continued

Met Thr Glu Glu His Val Ala Lys Ser Leu Glu Gly Leu Thr Val Gln
            405                 410                 415

Gln Ala Leu Ala Gly Asn Arg Leu Tyr Ile Val Asp Gln His Asp Asn
        420                 425                 430

Leu Met Pro Phe Leu Ile Asp Ile Asn Asn Leu Asp Ala Ser Phe Val
            435                 440                 445

Tyr Ala Thr Arg Thr Leu Leu Phe Leu Arg Gly Asp Gly Thr Leu Ala
    450                 455                 460

Pro Val Ala Ile Glu Leu Ser Ser Pro Leu Ile Gln Gly Glu Leu Thr
465                 470                 475                 480

Thr Ala Lys Ser Ala Val Tyr Thr Pro Gln His Ala Gly Val Glu Gly
            485                 490                 495

Trp Ile Trp Gln Leu Ala Lys Ala Tyr Ala Ser Val Asn Asp Tyr Gly
            500                 505                 510

Trp His Gln Leu Ile Ser His Trp Leu Asn Thr His Ala Val Met Glu
        515                 520                 525

Pro Phe Val Ile Ala Thr Asn Arg Gln Leu Ser Val Thr His Pro Val
        530                 535                 540

Tyr Lys Leu Leu His Pro His Tyr Arg Asp Thr Met Asn Ile Asn Ala
545                 550                 555                 560

Arg Ala Arg Gly Leu Leu Ile Asn Ala Gly Val Ile Glu Met Thr
            565                 570                 575

Val Phe Pro His Lys His Ala Met Pro Met Ser Ser Met Val Tyr Lys
            580                 585                 590

His Trp Asn Phe Thr Glu Gln Ala Leu Pro Ala Asp Leu Ile Lys Arg
        595                 600                 605

Gly Met Ala Val Glu Asp Ala Ser Ser Pro His Lys Val Arg Leu Leu
        610                 615                 620

Ile Lys Asp Tyr Pro Tyr Ala Thr Asp Gly Leu Ala Val Trp Asp Ala
625                 630                 635                 640

Ile Glu Gln Trp Val Ser Asp Tyr Leu Thr Ile Tyr Tyr Pro Asn Asp
            645                 650                 655

Gly Val Leu Gln Gly Asp Val Glu Leu Gln Ala Trp Trp Lys Glu Val
            660                 665                 670

Arg Glu Val Gly His Gly Asp Leu Lys Asp Ala Ala Trp Trp Pro Lys
        675                 680                 685

Met Gln Thr Val Ala Glu Leu Ile Lys Ala Cys Ala Thr Ile Ile Trp
        690                 695                 700

Thr Gly Ser Ala Leu His Ala Ala Val Asn Phe Gly Gln Tyr Pro Tyr
705                 710                 715                 720

Ser Gly Tyr His Pro Asn Lys Pro Ser Ala Ser Arg Arg Pro Met Pro
            725                 730                 735

Val Gln Gly Ser Glu Glu Tyr Ala Glu Leu Glu Arg Asp Pro Glu Lys
        740                 745                 750

Ala Phe Ile Arg Thr Ile Thr Ser Gln Phe His Ala Leu Val Gly Ile
        755                 760                 765

Ser Leu Met Glu Ile Leu Ser Lys His Ser Ser Asp Glu Val Tyr Leu
        770                 775                 780

Gly Gln His Asp Thr Pro Ala Trp Thr Ser Asp Ala Lys Ala Leu Glu
785                 790                 795                 800

Ala Phe Lys Arg Phe Gly Ala Lys Leu Glu Gly Ile Glu Lys Gln Val
            805                 810                 815

```
Val Ala Met Asn Ser Asp Pro Gln Leu Lys Asn Arg Thr Gly Pro Ala
            820                 825                 830

Lys Phe Pro Tyr Met Leu Leu Tyr Pro Asn Thr Ser Asp His Thr Gly
        835                 840                 845

Gln Ala Glu Gly Leu Thr Ala Arg Gly Ile Pro Asn Ser Ile Ser Ile
    850                 855                 860
```